US007090844B2

(12) United States Patent
Bar-Eli et al.

(10) Patent No.: US 7,090,844 B2
(45) Date of Patent: *Aug. 15, 2006

(54) USE OF ANTIBODIES AGAINST THE MUC18 ANTIGEN

(75) Inventors: Menashe Bar-Eli, Houston, TX (US); Larry L. Green, San Francisco, CA (US)

(73) Assignee: Abgenix, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/660,357

(22) Filed: Sep. 10, 2003

(65) Prior Publication Data

US 2004/0115205 A1    Jun. 17, 2004

Related U.S. Application Data

(63) Continuation of application No. 10/330,580, filed on Dec. 26, 2002, now abandoned.

(60) Provisional application No. 60/346,460, filed on Dec. 28, 2001.

(51) Int. Cl.
| | |
|---|---|
| *A61K 39/395* | (2006.01) |
| *C07K 16/00* | (2006.01) |
| *C12P 21/00* | (2006.01) |
| *C12P 21/04* | (2006.01) |
| *C12P 21/08* | (2006.01) |

(52) U.S. Cl. ............................... 424/142.1; 424/130.1; 424/155.1; 424/156.1; 424/181.1; 530/387.1; 530/388.15; 530/388.85; 530/391.7; 435/69.6; 800/6

(58) Field of Classification Search ............. 424/130.1, 424/133.1, 141.1, 143.1, 155.1, 181.1, 183.1, 424/142.1; 530/387.1, 387.3, 388.1, 388.15, 530/388.8, 391.3, 391.7
See application file for complete search history.

(56) References Cited

U.S. PATENT DOCUMENTS

| | | | |
|---|---|---|---|
| 4,735,210 | A | 4/1988 | Goldenberg |
| 5,101,827 | A | 4/1992 | Goldenberg |
| 5,102,990 | A | 4/1992 | Rhodes |
| 5,466,468 | A | 11/1995 | Schneider et al. |
| 5,648,471 | A | 7/1997 | Buttram et al. |
| 5,697,901 | A | 12/1997 | Eriksson |
| 5,800,820 | A | 9/1998 | Maione |
| 6,024,956 | A | 2/2000 | Matsushima et al. |
| 6,133,426 | A | 10/2000 | Gonzalez et al. |
| 6,150,584 | A | 11/2000 | Kucherlapati et al. |
| 6,229,048 | B1 | 5/2001 | Mazur et al. |
| 6,342,221 | B1 | 1/2002 | Thorpe et al. |
| 2003/0068319 | A1 | 4/2003 | Bar-Eli |

FOREIGN PATENT DOCUMENTS

| | | | |
|---|---|---|---|
| EP | 0 710 719 A | 5/1996 | |
| WO | WO 98/24893 A2 | 6/1998 | |
| WO | WO 00/76310 A1 | 12/2000 | |
| WO | WO 02/077172 A2 | 10/2002 | |
| WO | WO 03/057006 A2 | 7/2003 | |

OTHER PUBLICATIONS

Jain R. K. Scientific American, 271(1):58-65, Jul. 1994.*
Dillman, Annals of Internal Medicine, 111:592-603, 1989.*
Weiner L. M. Seminars in Oncology, 26 (4 Suppl 12):41-50, Aug. 1999.*
Dillman, R. O. Clinical Onocology, 12(7):1497-1515, 1994.*
Anfosso et al., "Activation of Human Endothelial Cells via S-Endo-1 Antigen (CD146) Stimulates the Tyrosine Phosphorylation of Focal Adhesion Kinase p125$^{FAK}$," *J. Bio, Chem.*, 273(41):26852-26856 (1998).
Bani et al., "Multiple Features of Advanced Melanoma Recapitulated in Tumorigenic Variants of Early Stage (Radial Growth Phase) Human Melanoma Cell Lines Evidence for a Dominant Phenotype$^1$," *Cancer Res.*, 56:3075-3086 (1996).
Bar-Eli, M., "Role of AP-2 in tumor growth and metastasis of human melanoma," *Cancer and Metastasis Reviews*, 18:377-385 (1999).
Frankel et al., "Cell Surface Receptor-Targeted of Acute Myeloid Leukemia: A Review," *Cancer Biotherapy & Radiopharmaceuticals*, 15(5):459-476 (2000).
Hedrick et al., "The DCC gene product in cellular differentiation and colorectal tumorigenesis," *Genes & Development*, 8:1174-83 (1994).
Holzmann et al. "Tumor Progression in Human Malignant Melanoma: Five Stages Defined by Their Antigenic Phenotypes," *Int. J. Cancer*, 39:466-471 (1987).
Jean et al., "Regulation of tumor growth and metastasis of human melanoma by the CREB transcription factor family," *Molecular and Cellular Biochemistry*, 212:19-28 (2000).
Johnson, J.P., "Cell adhesion molecules in the development and progression of malignant melanoma," *Cancer and Metastasis Reviews*, 18:345-357 (1999).
Johnson, J.P. et al., "Melanoma Progression-Associated Glycoprotein MUC18/MCAM Mediates Homotypic Cell Adhesion Through Interaction with a Heterophilic Ligand," *Int. J. Cancer*, 73:769-774 (1997).

(Continued)

*Primary Examiner*—Larry R. Helms
*Assistant Examiner*—David J. Blanchard
(74) *Attorney, Agent, or Firm*—Knobbe Martens Olson & Bear LLP

(57) ABSTRACT

The present invention relates generally to the generation and characterization of anti-MUC18 monoclonal antibodies. The invention further relates to the use of such anti-MUC18 antibodies in the diagnosis and treatment of disorders associated with increased activity of MUC18, in particular, tumors, such as melanomas.

27 Claims, 36 Drawing Sheets

OTHER PUBLICATIONS

Junghans et al., *Cancer Chemotherapy and Biotherapy: Principals and Practice*, pp. 655-689 (2d ed., Chabner and Long eds., Lippincott Raven 1996).

Knoll et al., "Targeted Therapy of Experimental Renal Cell Carcinoma with a Novel Conjugate of Monoclonal Antibody 138H11 and Calicheamicin $\theta^1_1$," *Cancer Res.*, 60:6089-6094 (2000).

Lai et al., "Two forms of 1B236/myelin-associated glycoprotein, a cell adhesion molecule for postnatal neural development, are produced by alternative splicing," *Proc. Natl. Acad. Sci. USA*, 84:4337-4341 (1987).

Lehmann, J.M. et al., "Discrimination Between Benign and Malignant Cells of Melanocytic Lineage by Two Novel Antigens, a Glycoprotein with a Molecular Weight of 113,000 and a Protein with a Molecular Weight of 76,000[b]" *Cancer Res.*, 47:841-845 (1987).

Lehmann, J.M. et al. "MUC18, a marker of tumor progression in human melanoma, shows sequence similarity to the neutral cell adhesion molecules of the immunoglobulin superfamily," *Proc. Natl. Acad. Sci. USA*, 86:9891-9895 (1989).

Liu et al., "Eradicaton of large colon tumor xenografts by targeted delivery of maytansinoids," *Proc. Natl. Acad. Sci. USA*, 93:8618-8623 (1996).

Luca, M. "Direct correlation between MUC18 expression and metastatic potential of human melanoma cells," *Melanoma Res.*, 3:35-41 (1993).

Mandler et al., "Immunoconjugates of Geldanamycin and Anti-HER2 Monoclonal Antibodies: Antiproliferative Activity of Human Breast Carcinoma Cell Lines," *J. Natl. Cancer Inst.*, 92(19):1573-1581 (2000).

Ota et al., "Antitumor effect of monoclonal antibody-carboplatin conjugates in nude mice bearing human ovearian cancer cells," *Int. J. Clin. Oncol.*, 4:236-240 (1999).

Owens et al., "Organization of the neural cell adhesion molecule (N-CAM) gene: Alternative exon usage as the basis for different membrane-associated domains," *Proc. Natl., Acad. Sci. USA*, 84:294-298 (1987).

Pickl, W.F. et al., "MUC18/MCAM (CD146), An Activation Antigen of Human T-Lymphocytes," *J. Immunol.*, 158:2107-2115 (1997).

Pourquié et al., "BEN, a surface glycoprotein of the immunoglobulin superfamily, is expressed in a variety of developing systems," *Proc. Natl. Acad. Sci., USA*, 89:5261-5265 (1992).

Satyamoorthy, K. et al., "Mel-CAM-specific genetic suppressor elements inhibit melanoma growth and invasion through loss of gap junctional communication," *Oncogene*, 20:4676-4684 (2001).

Schlagbauer-Wadl, et al., "Influence of MUC18/MCAM/CD146 expression on human melanoma growth and metastasis in scid mice," *Int. J. Cancer*, 81:951-955 (1999).

Sers et al., Genomic organization of the melanoma-associated glycoprotein MUC18: Implications for the evolution of the immunoglobulin domains, *Proc. Natl. Acad. Sci. USA*, 90:8514-8518 (1993).

Sers et al., "MUC18, a Melanoma-Progression Associated Molecule, and Its Potential Role in Tumor Vascularization and Hematogenous Spread[1]" *Cancer Research*, 54:5689-5694 (1994).

Shih et al., "Expression of melanoma cell adhesion molecule in intermediate trophoblast," *Lab. Invest.*, 75(3):377-388 (1996).

Shih et al., "Isolation and Functional Characterization of the A32 Melanoma-associated Antigen[1]," *Cancer Res.*, 54:2514-2520 (1994).

Shih et al. "The Cell-Cell Adhesion Receptor Mel-CAM Acts As a Tumor Suppressor in Breat Carcinoma," *Am. J. Pathol.*, 151(3):745-751 (1997).

Shih et al., "Melanoma Cell-Cell Interactions Are Mediated Trough Heterophilic Mel-CAM/Ligand Adhesion[1]," *Cancer Res.*, 57:3835-3840 (1997).

Shih et al., "Diagnostic and Biological Implications of Mel-CAM Expression in Mesenchymal Neoplasms," *Clinical Cancer Res.*, 2:569-575 (1996).

Taira et al., "Molecular Cloning and Functional Expression of Gicerin, a Novel Cell Adhesion Molecule That Binds Neurite Outgrowth Factor," *Neuron*, 12:861-872 (1994).

Xie et al., "Expression of MCAM/MUC18 by Human Melanoma Cells Leads to Increased Tumor Growth and Metastasis[1]," *Cancer Res.*, 57:2295-2303 (1997).

Higuchi et al., Cyclic AMP Enhances the Expression of an Extravillous Trophoblast Marker, Melanoma Cell Adhesion Molecule, in Choriocarcinoma Cell JEG3 and Human Chorionic Villous Explant Cultures, *Molecular Human Reproduction*, 9: 359-366 (2003).

Arenberg et al. "Inhibition of Interleukin-8 Reduces Tumorigenesis of Human Non-Small Cell Lung Cancer in SCID Mice." *J. Clin. Invest.*, 97(12):2792-2802 (1996).

Davis, et al. "Transgenic mice as a source of fully human antibodies for the tratment of cancer." *Cancer and Metastasis Reviews*, 18:421-425 (1999).

Green et al. "Interleukin-8 (IL-8), Melanoma Growth-stimulatory Activity, and Neutrophil-activating Peptide Selectivity Mediate Priming of the Neutrophil NADPH Oxidase through the Type A or Type B IL-8 Receptor." *The Journal of Biological Chemistry*, 271(41):25400-25405 (1996).

Lehmann et al. "MUC18 a marker of tumor progression in human melanoma shows sequence similarity to the neural cell adhesion molecules of the immunoglobulin superfamily." *Proceedings of the National Academy of Sciences USA*, 86:9891-9895 (1989).

Luca et al. "Expression of Interleukin-8 by Human Melanoma Cells Up-Regulates MMP-2 Activity Increases Tumor Growth and Metastasis." *American Journal of Pathology*, 4:1105-1113 (1997).

Mendez et al. "Functional tranplant of megabase human immunoglobulin loci recapitulates human antibody response in mice." *Nature Genetics*, 15(2):146-156 (1997).

Michi et al. "Human oral squamous cell carcinoma cell lines promote angiogenesis via expression of vascular endothelial growth factor and upregulation of KDR/flk-1 expression in endothelial cells." *Oral Oncology*, 36:81-88 (2000).

Rofstad et al. "Vascular Endothelial Growth Factor, Interleukin-8, Platelet-derived Endothelial Cell Growth Factor, and Basic Fibroblast Growth Factor Promote Angiogenesis and Metastasis in Human Melanoma Xenografts." *Cancer Research*, 60:4932-4938 (2000).

Scott et al. "Atracurium: Clinical strategies for preventing histamine release and attenuating the haemodynamic response." *Br. J. Anaesth.*, 57:550-553 (1985).

Shih et al. "A new MEL-CAM (CD146)-specific monoclonal antibody, MN-4, on paraffin-embedded tissue." *Modern Pathology*, 11(11):1098-1106 (1998).

Shih, Le-Ming. "The role of CD146 (MEL-CAM) in biology and pathology." *Journal of Pathology*, 189(1):4-11 (1999).

Singh et al. " Ultraviolet B Irradiation Promotes Tumorigenic and Metastatic Properties in Primary Cutaneous Melanoma via Induction of Interleukin 8[1]. " *J. Cancer Research*, 55:3669-3674 (1995).

Yang et al. "Development of ABX-EGF, a fully human anti-EGF receptor monoclonal antibody for cancer therapy." *Critical Reviews in Oncology-Hematology*, 38(1):17-23 (2001).

Mills L, et al., *Cancer Research*, 62:5108-5114, Sep. 2002.

Pickl, W.F. et al. *Journal of Immunology*, 158:2107-2115, Mar. 1997.

Slvam, G et al. *Cancer Research*, 47(12):3169-3173, 1987.

Wimazal, F. et al. *Tissue Antigens*, 54:499-507, Nov. 1999.

Xie et al. *Cancer Research*, 57:2295-2303, Jun. 1997.

\* cited by examiner

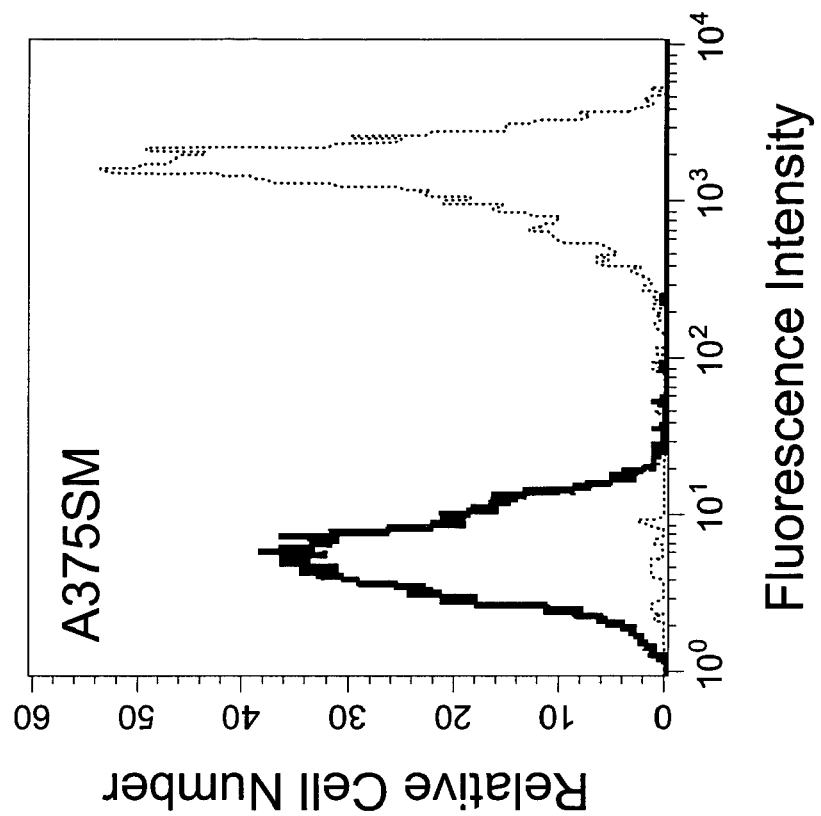
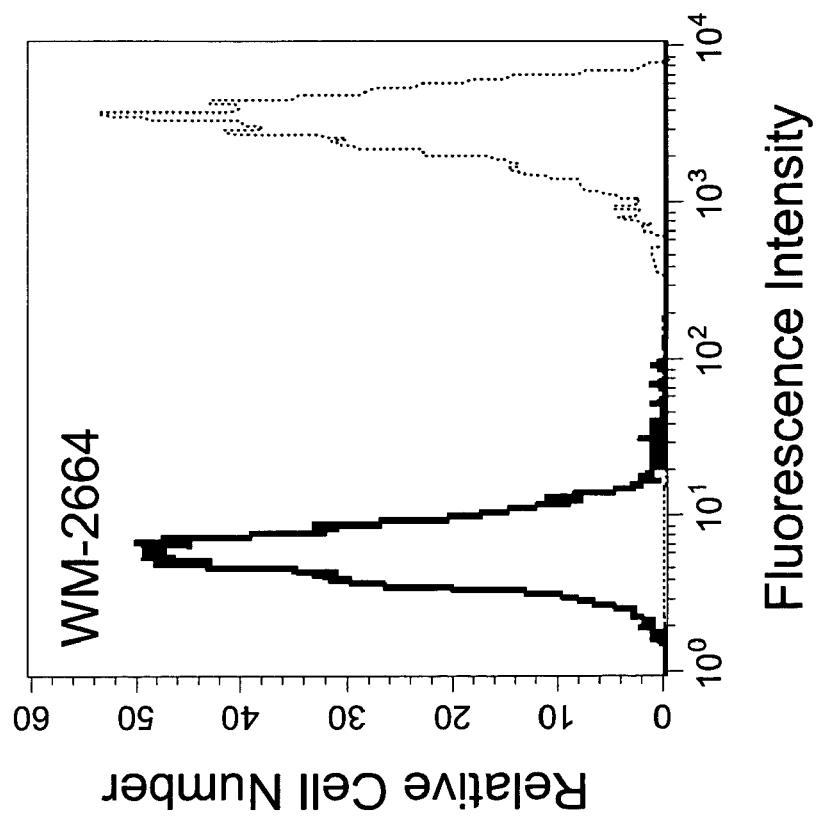
FIG. 3B
FIG. 3A

ANTI-MUC18 ANTIBODY C3.19.1

Nucleotide Sequence of Heavy Chain Variable Region

5'-
CAGGTGCAGCTGCAGGAGTCGGGCCCAGGACTGGTGAAGCCTTCGGAGACCCTGTCCCTCACCTGC
ACTGTCTCTGGTGGCTCCATCAGTAGTTACTACTGGAGCTGGATCCGGCAGCCCCCAGGGAAGGGA
CTGGAGTGGATTGGCTATATCTATTACACTTGGACCTCCAACTACAACCCCTCCCTCAAGAGTCGC
GTCACCATATCAGTGGACACGTCCAAAAACCAGTTCTCCCTGAGGCTGAGTTCTGTGACCGCTGCG
GACACGGCCGTTTATTACTGTGCGAGAGATCAGGGGCAGTGGTTACTACCCGATGCTTTTGATATC
TGGGGCCAAGGGACAATGGTCACCGTCTCTTCAG 3'   (SEQ ID NO: 3)

Amino Acid Sequence of Heavy Chain Variable Region

QVQLQESGPGLVKPSETLSLTCTVSGGSISSYYWSWIRQPPGKGLEWIGYIYYTWTSNYNPSLKSR
VTISVDTSKNQFSLRLSSVTAADTAVYYCARDQGQWLLPDAFDIWGQGTMVTVSS   (SEQ ID NO:1)

Nucleotide Sequence of Light Chain Variable Region

5'-
GATATTGTGATGACTCAGTCTCCACTCTCCCTGCCCGTCACCCCTGGAGAGCCGGCCTCCATCTCC
TGCAGGTCTAGTCAGAGCCTCCTGCGTAGTAATGGATACAACTATTTGGATTGGTACCTGCAGAAG
CCAGGACAGTCTCCACATCTCCTGATCTATTTGGGTTCTAATCGGGCCTCCGGGGTCCCTGACAGG
TTCAGTGGCAGTGGATCAGGCACAGATTTTACACTGAAAATCAGCAGAGTGGAGGCTGAGGATGTT
GGGGTTTATTACTGCATGCAAGCTCAACAAAGTCCGATCACCTTCGGCCAAGGGACACGACTGGAG
ATTAAAC 3'   (SEQ ID NO: 4)

Amino Acid Sequence of Light Chain Variable Region

DIVMTQSPLSLPVTPGEPASISCRSSQSLLRSNGYNYLDWYLQKPGQSPHLLIYLGSNRASGVPDR
FSGSGSGTDFTLKISRVEAEDVGVYYCMQAQQSPITFGQGTRLEIK   (SEQ ID NO: 2)

*FIG. 6*

ANTI-MUC18 ANTIBODY C6.11.13

Nucleotide Sequence of Heavy Chain Variable Region

5'-
CAGGTGCAGCTGCAGGAGTCGGGCCCAGGACTGGTGAAGCCTTCACAGACCCTGTCCCTCACCTGC
ACTGTCTCTGGTGGCTCCATCAGCAGTGGTACTTACCACTGGAGCTGGATCCGCCAGCACCCAGGG
AAGGGCCTGGAGTGGATTGGGTACATCTATTACAGTGGGAGCACCTACTACAACCCGTCCCTCAAG
AGTCGAGTTACCATATCAGTAGACACGTCTAAGAACCAGTTCTCCCTGAAGCTGAGCTCTGTGACT
GCCGCGGACACGGCCGTGTATTACTGTGCGAGAGGGGGAGATGGCTACAAGTACTGGGGCCAGGGA
ACCCTGGTCACCGTCTCCTCAG-3'  (SEQ ID NO: 7)

Amino Acid Sequence of Heavy Chain Variable Region

QVQLQESGPGLVKPSQTLSLTCTVSGGSISSGTYHWSWIRQHPGKGLEWIGYIYYSGSTYYNPSLK
SRVTISVDTSKNQFSLKLSSVTAADTAVYYCARGGDGYKYWGQGTLVTVSS   (SEQ ID NO: 5)

Nucleotide Sequence of Light Chain Variable Region

5'
GAAATAGTGATGACGCAGTCTCCAGCCACCCTGTCTGTGTCTCCAGGGGAAAGAGCCACCCTCTCC
TGCAGGGCCAGTCAGAGTGTTAGCAACAACTTAGCCTGGTATCAGCAGAAACCTGGCCAGGCTCCC
AGGCTCCTCATCTATGGTGCATCCACCAGGGCCACTGGTATCCCAGCCAGGTTCAGTGGCAGTGGG
TCTGGGACAGAGTTCACTCTCACCATCAGCAGCCTGCAGTCTGAAGATTTTGCAGTTTATTACTGT
CAGCAGTATAATAACTGGCCTCGGACGTTCGGCCAAGGGACCAAGGTGGAAATCAAAC 3'
(SEQ ID NO: 8)

Amino Acid Sequence of Light Chain Variable Region

EIVMTQSPATLSVSPGERATLSCRASQSVSNNLAWYQQKPGQAPRLLIYGASTRATGIPARFSGSG
SGTEFTLTISSLQSEDFAVYYCQQYNNWPRTFGQGTKVEIK   (SEQ ID NO: 6)

FIG. 7

ANTI-MUC18 ANTIBODY C3.10

Nucleotide Sequence of Heavy Chain Variable Region

```
  1 CAGGTGCAGC TGCAGGAGTC GGGCCCAGGA CTGGTGAAGC CTTCGGAGAC CCTGTCCCTC
 61 ACCTGCACTG TCTCTGGTGG CTCCATCAGT AGTTACTACT GGAGCTGGAT CCGGCAGCCC
121 CCAGGGAAGG GACTGGAGTG GATTGGCTAT ATCTATTACA CTTGGACCAC CAACTACAAC
181 CCCTCCCTCA AGAGTCGCGT CACCATATCA GTGGACACGT CCAAGAACCA GTTCTCCCTG
241 AGGCTGAGCT CTGTGACCGC TGCGGACACG GCCCTTTATT ACTGTGCGAG AGATCAGGGG
301 CAGTGGTTAC TACCCGATGC TTTTGATATC TGGGGCCAAG GGACAATGGT CACCGTCTCT
361 TCAG (SEQ ID NO: 11)
```

Amino Acid Sequence of Heavy Chain Variable Region

```
  1 QVQLQESGPG LVKPSETLSL TCTVSGGSIS SYYWSWIRQP PGKGLEWIGY IYYTWTTNYN
 61 PSLKSRVTIS VDTSKNQFSL RLSSVTAADT ALYYCARDQG QWLLPDAFDI WGQGTMVTVS
121 S (SEQ ID NO: 9)
```

Nucleotide Sequence of Light Chain Variable Region

```
  1 GACATCCAGA TGACCCAGTC TCCATCCTCC CTGTCTGCAT CTGTAGGAGA CAGAGTCACC
 61 ATCACTTGCC GGGCAAGTCA GAGCATTAGC AACTATTTAA ATTGGTATCA GCAGAAACCA
121 GGAAAAGCCC CTAAGCTCCT GATCTATGGT GCATCCAGTT TGCAAAGTGG GGTCCCATCA
181 AGGTTCAGTG GCAGTGGATC TGGGACAGAT TTCACTCTCA CCATCAGCAG TCTGCAACCT
241 GAAGATTTTG CAACCTACTA CTGTCGACAG AGTTACAGTA CCCCTCCGGA GTGCAGTTTT
301 GGCCAGGGGA CCAAGCTGGA GATCAAAC (SEQ ID NO: 12)
```

Amino Acid Sequence of Light Chain Variable Region

```
  1 DIQMTQSPSS LSASVGDRVT ITCRASQSIS NYLNWYQQKP GKAPKLLIYG ASSLQSGVPS
 61 RFSGSGSGTD FTLTISSLQP EDFATYYCRQ SYSTPPECSF GQGTKLEIK (SEQ ID NO:10)
```

FIG. 8

ANTI-MUC18 ANTIBODY C3.22

Nucleotide Sequence of Heavy Chain Variable Region

```
  1 CAGGTGCAGC TGCAGGAGTC GGGCCCAGGA CTGGTGAAGC CTTCACAGAC CCTGTCCCTC
 61 ACCTGCACTG TCTCTGGTGG CTCCATCAGC AGTGGTGGTT ACTACTGGAC TTGGATCCGC
121 CAGCACCCAG GGAAGGGCCT GGAGTGGATT GGGTTCATCT ATTACAGTGG GAGCACCTAC
181 TACAACCCGT CCCTCAAGAG TCGAGTTACC ATATCAGTAG ACACGTCTAA GAACCAGTTC
241 TCCCTGAAGC TGAGCTCTGT GACTGCCGCG GACACGGCCG TGTATTACTG TGCGAGAGAG
301 GGAGATGGCT TTGACTACTG GGGCCAGGGA ACCCTGGTCA CCGTCTCCTC AG
(SEQ ID NO: 15)
```

Amino Acid Sequence of Heavy Chain Variable Region

```
  1 QVQLQESGPG LVKPSQTLSL TCTVSGGSIS SGGYYWTWIR QHPGKGLEWI GFIYYSGSTY
 61 YNPSLKSRVT ISVDTSKNQF SLKLSSVTAA DTAVYYCARE GDGFDYWGQG TLVTVSS
(SEQ ID NO: 13)
```

Nucleotide Sequence of Light Chain Variable Region

```
  1 GACATCCAGA TGACCCAGTC TCCATCCTCC CTGTCTGCAT CTGTAGGAGA CAGAGTCACC
 61 ATCACTTGCC GGGCAAGTCA GGGCATTAGA AATGATTTAG CTGGTATCA GCAGAAACCA
121 GGGAAAGCCC CTAAGCGCCT GATCTATGCT GCATCCAGTT TGCAAAGTGG GGTCCCATCA
181 AGGTTCAGCG GCAGTGGATC TGGGACAGAA TTCACTCTCA CAATCAGCAG CCTGCAGCCT
241 GAAGATTTTG CAACTTATTA CTGTCTACAG CATAATAGTT ACCCGCTCAC TTTCGGCGGA
301 GGGACCAAGG TGGAGATCAA AC (SEQ ID NO: 16)
```

Amino Acid Sequence of Light Chain Variable Region

```
  1 DIQMTQSPSS LSASVGDRVT ITCRASQGIR NDLGWYQQKP GKAPKRLIYA ASSLQSGVPS
 61 RFSGSGSGTE FTLTISSLQP EDFATYYCLQ HNSYPLTFGG GTKVEIK (SEQ ID NO: 14)
```

*FIG. 9*

ANTI-MUC18 ANTIBODY C3.27

Nucleotide Sequence of Heavy Chain Variable Region

```
  1 CAGGTGCAGC TGCAGGAGTC GGGCCCAGGA CTGGTGAAGC CTTCGGAGAC CCTGTCCCTC
 61 ACCTGCACTG TCTCTGGTGG CTCCATCAGT AGTTACTACT GGAGCTGGAT CCGGCAGCCC
121 CCAGGGAAGG GACTGGAGTG GATTGGCTAT ATCTATTACA CTTGGACCTC CAACTACAAC
181 CCCTCCCTCA AGAGTCGCGT CACCATATCA GTGGACACGT CCAAGAACCA GTTCTCCCTG
241 AGGCTGAGTT CTGTGACCGC TGCGGACACG GCCGTTTACT ACTGTGCGAG AGATCAGGGG
301 CAGTGGTTAC TACCCGATGC TTTTGATATC TGGGGCCAAG GGACAATGGT CACCGTCTCT
361 TCAG (SEQ ID NO: 19)
```

Amino Acid Sequence of Heavy Chain Variable Region

```
  1 QVQLQESGPG LVKPSETLSL TCTVSGGSIS SYYWSWIRQP PGKGLEWIGY IYYTWTSNYN
 61 PSLKSRVTIS VDTSKNQFSL RLSSVTAADT AVYYCARDQG QWLLPDAFDI WGQGTMVTVS
121 S (SEQ ID NO: 17)
```

Nucleotide Sequence of Light Chain Variable Region

```
  1 GACATCCAGA TGACCCAGTC TCCATCCTCC CTGTCTGCAT CTGTAGGAGA CAGAGTCACC
 61 ATCACTTGCC GGGCAAGTCA GGGCATTAGA AATGATTTAG CTGGTATCA GCAGAAACCA
121 GGGAAAGCCC CTAAGCGCCT GATCTATGCT GCATCCAGTT TGCAAAGTGG GGTCCCATCA
181 AGGTTCAGCG GCAGTGGATC TGGGACAGAG TTCACTCTCA CAATCAGCAG CCTGCAGCCT
241 GAAGATTTTG CAACTTATTA CTGTCTACAG CATAATAGTT ACCCGTGGAC GTTCGGCCAA
301 GGGACCAAGG TGGAAATCAA AC (SEQ ID NO: 20)
```

Amino Acid Sequence of Light Chain Variable Region

```
  1 DIQMTQSPSS LSASVGDRVT ITCRASQGIR NDLGWYQQKP GKAPKRLIYA ASSLQSGVPS
 61 RFSGSGSGTE FTLTISSLQP EDFATYYCLQ HNSYPWTFGQ GTKVEIK
(SEQ ID NO: 18)
```

FIG. 10

ANTI-MUC18 ANTIBODY C3.45

Nucleotide Sequence of Heavy Chain Variable Region

```
  1 CAGGTTCAGC TGGTGCAGTC GGGAGCTGAG GTGAAGAAGC CTGGGGCCTC AGTGAAGGTC
 61 TCCTGCAAGG CTTCTGGTTA CACCTTTTTT AGCTATGGTT TCAGCTGGGT GCGACAGGCC
121 CCTGGACAAG GGCTTGAGTG GCTGGGATGG ATCAGCGCTT ACAATGGTAA CACAAACTAT
181 GCACAGAAGC TCCAGGGCAG AGTCACCATG ACCACAGACA CTTCCACGAG CACAGCCTAC
241 ATGGAGCTGA GGAGCCTGAG ATCTGACGAC ACGGCCGTGT ATTACTGTGC GAGAGAAACT
301 AAGGTTCGGG GAGTCCACTA CTACGGTATG GACGTCTGGG GCCAAGGGAC CACGGTCACC
361 GTCTCCTCAG (SEQ ID NO: 23)
```

Amino Acid Sequence of Heavy Chain Variable Region

```
  1 QVQLVQSGAE VKKPGASVKV SCKASGYTFF SYGFSWVRQA PGQGLEWLGW ISAYNGNTNY
 61 AQKLQGRVTM TTDTSTSTAY MELRSLRSDD TAVYYCARET KVRGVHYYGM DVWGQGTTVT
121 VSS (SEQ ID NO: 21)
```

Amino Acid Sequence of Light Chain Variable Region

```
  1 DIVMTQSPDS LAVSLGERAT IICKSSQSIL YSSNNKNYLG WYQQKPGQPP KLLIYWASTR
 61 ESGVPARFSG SGSGTDFTLT INSLQAEDVA VYYCQQYYST PRSFGQGTMV EIK (SEQ ID
NO: 22)
```

Nucleotide Sequence of Light Chain Variable Region

```
  1 GACATCGTGA TGACCCAGTC TCCAGACTCC CTGGCTGTGT CTCTGGGCGA GAGGGCCACC
 61 ATCATCTGCA AGTCCAGCCA GAGTATTTTA TACAGCTCCA ACAATAAGAA CTACTTAGGT
121 TGGTACCAGC AGAAACCAGG ACAGCCTCCT AAGCTGCTCA TTTACTGGGC ATCTACCCGG
181 GAATCCGGGG TCCCTGCCCG ATTCAGTGGC AGCGGGTCTG GGACAGATTT CACTCTCACC
241 ATCAACAGCC TGCAGGCTGA AGATGTGGCA GTTTATTACT GTCAGCAATA TTATAGTACT
301 CCTCGGTCGT TCGGCCAAGG GACCATGGTG GAAATCAAAC (SEQ ID NO 24)
```

FIG. 11

ANTI-MUC18 ANTIBODY C3.65

Nucleotide Sequence of Heavy Chain Variable Region

```
  1 CAGGTGCAGC TGCAGGAGTC GGGCCCAGGA CTGGTGAAGC CTTCACAGAC CCTGTCCCTC
 61 ACCTGCACTG TCTCTGGTGG CTCCATCAAC AGTGGTGGTT GCTACTGGAG CTGGATCCGC
121 CAGCACCCAG GGAAGGGCCT GGAGTGGATT GGGTACATCT ATTCCAGTGG GAGCACCTAC
181 TACAACCCGT CCCTCAAGAG TCGAATTACC TTATCAGTAG ACACGTCTAA GAACCAGTTC
241 TCCCTGAAGC TGAACTCTAT GACTGCCGCG GACACGGCCG TGTATTACTG CGAGAGAT
301 CGGGAAACAG CTGGTTTTGA CTACTGGGGC CAGGGAACCC TGGTCACCGT CTCCTCAG
(SEQ ID NO: 27)
```

Amino Acid Sequence of Heavy Chain Variable Region

```
 1 QVQLQESGPG LVKPSQTLSL TCTVSGGSIN SGGCYWSWIR QHPGKGLEWI GYIYSSGSTY
61 YNPSLKSRIT LSVDTSKNQF SLKLNSMTAA DTAVYYCARD RETAGFDYWG QGTLVTVSS
(SEQ ID NO: 25)
```

Nucleotide Sequence of Light Chain Variable Region

```
  1 GACATCCAGA TGACCCAGTC TCCATCCTCC CTGTCTGCAT CTGTAGGAGA CAGAGTCACC
 61 ATCACTTGCC AGGCGAGTCA GGACATTAAC AACTATTTAA ATTGGTATCA GCAGAAACCA
121 GGGAAAGCCC CTAAGCTCCT GATCTACGAT GCATCCAATT TGGAAACAGG GGTCCCATCA
181 AGGTTCAGTG GAAGTGGATC TGGGACAGAT TTTACTTTCA CCATCAGCGG CCTGCAGCCT
241 GAGGATATTG CAACATATTA CTGTCAACAG TATGATACTC TCCCTCTCAC TTTCGGCGGC
301 GGGACCAAGG TGGAGATCAA AC (SEQ ID NO: 28)
```

Amino Acid Sequence of Light Chain Variable Region

```
 1 DIQMTQSPSS LSASVGDRVT ITCQASQDIN NYLNWYQQKP GKAPKLLIYD ASNLETGVPS
61 RFSGSGSGTD FTFTISGLQP EDIATYYCQQ YDTLPLTFGG GTKVEIK (SEQ ID NO: 26)
```

FIG. 12

ANTI-MUC18 ANTIBODY C6.1

Nucleotide Sequence of Heavy Chain Variable Region

```
  1 CAGGTGCAGC TGGTGGAGTC GGGGGGAGGC GTGGTCCAGC CTGGGAGGTC CCTGAGACTC
 61 TCCTGTGCAG CCTCTGGATT CACCTTCAGT AGCTATGCCA TGCACTGGGT CCGCCAGGCT
121 CCAGGCAAGG GGCTGGAGTG GGTGGCAGTT ATATCATATG ATGGAAGTAA TAAATACTAT
181 GCAGACTCCG TGAAGGGCCG ATTCACCATC TCCAGAGACA ATTCCAAGAA CACGCTGTAT
241 CTGCAAATGA ACAGCCTGAG AGCTGAGGAC ACGGCTGTGT ATTACTGTGC GAGATCGATT
301 TTTGGAGTGG TTATCGACTA CGGTATGGAC GTCTGGGGCC AAGGGACCAC GGTCACCGTC
361 TCCTCAG (SEQ ID NO: 31)
```

Amino Acid Sequence of Heavy Chain Variable Region

```
  1 QVQLVESGGG VVQPGRSLRL SCAASGFTFS SYAMHWVRQA PGKGLEWVAV ISYDGSNKYY
 61 ADSVKGRFTI SRDNSKNTLY LQMNSLRAED TAVYYCARSI FGVVIDYGMD VWGQGTTVTV
121 SS (SEQ ID NO: 29)
```

Nucleotide Sequence of Light Chain Variable Region

```
  1 GACATCCAGA TGACCCAGTC TCCATCCTCC CTGTCTGCAT CTGTAGGAGA CAGAGTCACC
 61 ATCACTTGCC GGGCGAGTCA GGGCATTAGA AATTATTTAG CCTGGTATCA GCAGAATCCA
121 GGGAAAGTTC CTAAGCTCCT GATCTATGGT GCATCCACTT TGCAATCAGG GGTCCCATCT
181 CGGTTCAGTG GCAGTGGATC TGGGACAGAT TTCACTCTCA CCATCAGCAG CCTGCAGCCT
241 GAAGATGTTG CAACTTATTA CTGTCAAAAG TTTAGCAGTC CCCATTCAC TTTCGGCCCT
301 GGGACCAAAG TGGATATCAG TC (SEQ ID NO: 32)
```

Amino Acid Sequence of Light Chain Variable Region

```
  1 DIQMTQSPSS LSASVGDRVT ITCRASQGIR NYLAWYQQNP GKVPKLLIYG ASTLQSGVPS
 61 RFSGSGSGTD FTLTISSLQP EDVATYYCQK FSSPPFTFGP GTKVDIS (SEQ ID NO: 30)
```

FIG. 13

ANTI-MUC18 ANTIBODY C6.9

Nucleotide Sequence of Heavy Chain Variable Region

```
  1 CAGGTGCAGC TGGAGCAGTC GGGGCCAGGA CTGGTGAAGC CTTCAGAGAC CCTGTCCCTC
 61 ACCTGCACTG TCTCTGGTGG CTCCATCAGC AGTGGTACTT ACCACTGGAG CTGGATCCGC
121 CAGCACCCAG GGAGGGGCCT GGAGTGGATT GGATACATCT ATTACAGTGG GAGCACCTAC
181 CACAACCCGT CCCTCAAGAG TCGAATTACC ATATCAGTAG ACACGTCTAA GAACCAGTTC
241 TCCCTGAAGC TGAGCTCTGT GACGGCCGCG GACACGGCCG TGTATTACTG TGCGAGAGGG
301 GGAGATGGCT ACAGATACTG GGGCCAGGGA ACCCTGGTCA CCGTCTCCTC AG
(SEQ ID NO: 35)
```

Amino Acid Sequence of Heavy Chain Variable Region

```
 1 QVQLEQSGPG LVKPSETLSL TCTVSGGSIS SGTYHWSWIR QHPGRGLEWI GYIYYSGSTY
61 HNPSLKSRIT ISVDTSKNQF SLKLSSVTAA DTAVYYCARG GDGYRYWGQG TLVTVSS
(SEQ ID NO: 33)
```

Nucleotide Sequence of Light Chain Variable Region

```
  1 GAAATAGTGA TGACGCAGTC TCCAGCCACC CTGTCTGTGT CTCCAGGGGA AAGAGCCACC
 61 CTCTCCTGCA GGGCCAGTCA GAGTATTAGC AACAACTTCG CCTGGTACCA GCAGAAACCT
121 GGCCAGGCTC CCAGGCTCCT CATCTTTGGT GCATCCACCA GGGCCACTGG TATCCCAGCC
181 AGGTTCAGTG GCAGTGGGTC TGGGACAGAA TTCACTCTCA CCATCAGCAG CCTACAGTCT
241 GAAGATTTTG CAGTTTATTA CTGTCAGCAG TATAATAACT GGCCTCGGAC GTTCGGCCAA
301 GGGACCAAGG TGGAAATCAA AC (SEQ ID NO: 36)
```

Amino Acid Sequence of Light Chain Variable Region

```
 1 EIVMTQSPAT LSVSPGERAT LSCRASQSIS NNFAWYQQKP GQAPRLLIFG ASTRATGIPA
61 RFSGSGSGTE FTLTISSLQS EDFAVYYCQQ YNNWPRTFGQ GTKVEIK (SEQ ID NO: 34)
```

FIG. 14

ANTI-MUC18 ANTIBODY C6.2

Nucleotide Sequence of Heavy Chain Variable Region

```
  1 CAGGTGCAGC TGCAGGAGTC GGGCCCAGGA CTGGTGAAGC CCTCGGAGAC CCTGTCCCTC
 61 ACCTGCACTG TCTCTGGTGG CTCCATCAGT ACTTACTACT GGAGTTGGAT CCGGCAGCCC
121 CCAGGGAAGG GACTGGAGTG GATTGGATAC ATCTATTACA CTGGGAACAC CTACTACAAC
181 CCCTCCCTCA AGAGTCGAGT CACCGTTTCA GTTGACACGT CCAAGAACCA GTTCTCCCTG
241 AAGCTGAACT CTGTGACCGC TGCGGACACG GCCGTGTATT ACTGTGCGAG AGATCCAGGC
301 CAGTGGCTGG TCCCTGATGC TTTTGATATC TGGGGCCAAG GGACAATGGT CTCCGTCTCT
361 TCAG (SEQ ID NO: 39)
```

Amino Acid Sequence of Heavy Chain Variable Region

```
  1 QVQLQESGPG LVKPSETLSL TCTVSGGSIS TYYWSWIRQP PGKGLEWIGY IYYTGNTYYN
 61 PSLKSRVTVS VDTSKNQFSL KLNSVTAADT AVYYCARDPG QWLVPDAFDI WGQGTMVSVS
121 S (SEQ ID NO: 37)
```

Nucleotide Sequence of Light Chain Variable Region

```
  1 GATATTGTGA TGACTCAGTC TCCACTCTCC CTGCCCGTCA TTCCTGGAGA GCCGGCCTCC
 61 ATCTCCTGCA GGTCTAGTCA GAGCCTCCTG CAGAGTAATG GAAACAACTA TTTGGATTGG
121 TACCTGCAGA AGCCAGGGCA GTCTCCACAG CTCCTGATCT ATTTGGGTTC TAATCGGGCC
181 TCCGGGGTCC CTGACAGGTT CAGTGGCAGT GGATCAGGCA CAGATTTTAC ACTGAAAATC
241 AGCAGAGTGG AGGCTGACGA TGTTGGGATT TATTACTGCA TGCAAGCTCT CCAAATTCCT
301 CTCACTTTCG GCGGAGGGAC CAAGGTGGAG ATCAAAC (SEQ ID NO: 40)
```

Amino Acid Sequence of Light Chain Variable Region

```
  1 DIVMTQSPLS LPVIPGEPAS ISCRSSQSLL QSNGNNYLDW YLQKPGQSPQ LLIYLGSNRA
 61 SGVPDRFSGS GSGTDFTLKI SRVEADDVGI YYCMQALQIP LTFGGGTKVE IK
(SEQ ID NO: 38)
```

FIG. 15

```
                                    1                                             53
A15-3.10_LC  (1)  DIQMTQSPSSLSASVGDRVTITCRASQSISNYLNWYQQKPGKAPKLLIYGASS
         O2  (1)  DIQMTQSPSSLSASVGDRVTITCRASQSISYLNWYQQKPGKAPKLLIYAASS
  Consensus  (1)  DIQMTQSPSSLSASVGDRVTITCRASQSIS YLNWYQQKPGKAPKLLIYAASS
                                          Section 1

54                                            106
A15-3.10_LC  (54) LQSGVPSRFSGSGSGTDFTLTISSLQPEDEATYYCQRQSYSTPPECSFGQGTKL
         O2  (54) LQSGVPSRFSGSGSGTDFTLTISSLQPEDFATYYCQQSYSTP----------
  Consensus  (54) LQSGVPSRFSGSGSGTDFTLTISSLQPEDFATYYC QSYSTP
                                          Section 2

107
A15-3.10_LC  (107) EIK
         O2   (96) ---
  Consensus (107)
                                          Section 3
```

| positives: 85.3% | identity: 84.4% |

*FIG. 17*

```
                        1                   10                  20                  30                  40                  53
A15-3.22_HC   (1)                                                                                                              
VH4-31        (1)    QVQLQESGPGLVKPSQTLSLTCTVSGGSISSSGGYYWTWIRQHPGKGLEWIGYI
              (1)    QVQLQESGPGLVKPSQTLSLTCTVSGGSISSSGGYYWSWIRQHPGKGLEWIGYI
Consensus     (1)    QVQLQESGPGLVKPSQTLSLTCTVSGGSISSSGGYYWSWIRQHPGKGLEWIGFI
                                                                                        Section 1

54                  60                  70                  80                  90                  106
A15-3.22_HC   (54)   YYSGSTYYNPSLKSRVTISVDTSKNQFSLKLSSVTAADTAVYYCAREGDGFDY
VH4-31        (54)   YYSGSTYYNPSLKSRVTISVDTSKNQFSLKLSSVTAADTAVYYCAR------
              (54)   YYSGSTYYNPSLKSRVTISVDTSKNQFSLKLSSVTAADTAVYYCAR
Consensus     (54)   YYSGSTYYNPSLKSRVTISVDTSKNQFSLKLSSVTAADTAVYYCAR
                                                                         Section 2

107         117
A15-3.22_HC   (107)  WGQGTLVTVSS
VH4-31        (107)  -----------
              (100)
Consensus     (107)
                                                 Section 3
``` positives: 84.6% | identity: 82.9%

FIG. 18

```
                        1               10        20        30        40        50
                        |                |         |         |         |         |   53
A15-3.22_LC  (1)  DIQMTQSPSSLSASVGDRVTITCRASQGIRNDLGWYQQKPGKAPKRLIYAASS
         A30  (1)  DIQMTQSPSSLSASVGDRVTITCRASQGIRNDLGWYQQKPGKAPKRLIYAASS
   Consensus  (1)  DIQMTQSPSSLSASVGDRVTITCRASQGIRNDLGWYQQKPGKAPKRLIYAASS
                                                                      ─── Section 1

54        60        70        80        90       100
                        |         |         |         |         |         |    106
A15-3.22_LC  (54)  LQSGVPSRFSGSGSGTEFTLTISSLQPEDFATYYCLQHNSYPLTFGGGTKVEI
         A30  (54)  LQSGVPSRFSGSGSGTEFTLTISSLQPEDFATYYCLQHNSYP---------
   Consensus  (54)  LQSGVPSRFSGSGSGTEFTLTISSLQPEDFATYYCLQHNSYP
                                                                      ─── Section 2

107
A15-3.22_LC  (107)  K
         A30   (96)  -
   Consensus (107)
                                                                      ─── Section 3
``` positives: 88.8%  identity: 88.8%

*FIG. 19*

```
                            1                10             20              30              40                 53
A15-3.27_HC   (1)  QVQLQESGPGLVKPSETLSLTCTVSGGSISSYYWSWIRQPPGKGLEWIGYIYY
VH4-59        (1)  QVQLQESGPGLVKPSETLSLTCTVSGGSISSYYWSWIRQPPGKGLEWIGYIYY
Consensus     (1)  QVQLQESGPGLVKPSETLSLTCTVSGGSISSYYWSWIRQPPGKGLEWIGYIYY
                                                                         Section 1
                   54            60              70              80              90            106
A15-3.27_HC  (54)  TWTSNYNPSLKSRVTISVDTSKNQFSLRLSSVTAADTAVYYCARDQGWLLPD
VH4-59       (54)  SGSTNYNPSLKSRVTISVDTSKNQFSLKLSSVTAADTAVYYCAR--------
Consensus    (54)  S SSNYNPSLKSRVTISVDTSKNQFSLKLSSVTAADTAVYYCAR
                                                                              Section 2
                   107              121
A15-3.27_HC (107)  AFDIWGQGTMVTVSS
VH4-59       (98)  ---------------
Consensus   (107)
                                      Section 3
``` positives: 79.3%   identity: 76.0%

FIG. 20

```
                           1                    10              20              30              40              53
A15-3.27_LC  (1)  DIQMTQSPSSLSASVGDRVTITCRASQGIRNDLGWYQQKPGKAPKRLIYAASS
         A30 (1)  DIQMTQSPSSLSASVGDRVTITCRASQGIRNDLGWYQQKPGKAPKRLIYAASS
   Consensus (1)  DIQMTQSPSSLSASVGDRVTITCRASQGIRNDLGWYQQKPGKAPKRLIYAASS
                                                                   Section 1

54           60              70              80              90             106
A15-3.27_LC (54)  LQSGVPSRFSGSGSGTEFTLTISSLQPEDFATYYCLQHNSYPWTFGQGTKVEI
         A30 (54) LQSGVPSRFSGSGSGTEFTLTISSLQPEDFATYYCLQHNSYP----------
   Consensus (54) LQSGVPSRFSGSGSGTEFTLTISSLQPEDFATYYCLQHNSYP
                                                                   Section 2

107
A15-3.27_LC (107)   K
         A30 (96)   -
   Consensus (107)
                                                                   Section 3
``` positives: 88.8% | identity: 88.8%

FIG. 21

```
                              1              10              20              30              40              50
A15-3.45_HC    (1)  QVQLVQSGAEVKKPGASVKVSCKASGYTFTSYGFSWVRQAPGQGLEWIGWISA    53
VH1-18         (1)  QVQLVQSGAEVKKPGASVKVSCKASGYTFTSYGISWVRQAPGQGLEWMGWISA
Consensus      (1)  QVQLVQSGAEVKKPGASVKVSCKASGYTF SYG  SWVRQAPGQGLEWLGWISA
                    ─────────────────────────────────────────── Section 1

54             60             70             80             90             100
A15-3.45_HC   (54)  YNGNTNYAQKLQGRVTMTTDTSTSTAYMELRSLRSDDTAVYYCARETKVRGVH   106
VH1-18        (54)  YNGNTNYAQKLQGRVTMTTDTSTSTAYMELRSLRSDDTAVYYCAR
Consensus     (54)  YNGNTNYAQKLQGRVTMTTDTSTSTAYMELRSLRSDDTAVYYCAR
                    ─────────────────────────────────────────── Section 2

107              123
A15-3.45_HC  (107)  YYGMDVWGQGTTVTVSS             123
VH1-18       (107)  ─────────────────
Consensus     (99)  YYGMDVWGQGTTVTVSS
                    ─────────────────────────────────────────── Section 3
``` positives: 78.0%   identity: 77.2%

FIG. 22

|              |       | 1           10          20          30          40          50   |
|---|---|---|
| A15-3.65_HC  | (1)   | QVQLQESGPGLVKPSQTLSLTCTVSGGSINSGGCYWSWIRQHPGKGLEWIGYI |
| VH4-31       | (1)   | QVQLQESGPGLVKPSQTLSLTCTVSGGSISSGGYYWSWIRQHPGKGLEWIGYI |
| Consensus    | (1)   | QVQLQESGPGLVKPSQTLSLTCTVSGGSI SGG YWSWIRQHPGKGLEWIGYI |

——————— Section 1 ——— 53

|              |       | 54          60          70          80          90         106 |
|---|---|---|
| A15-3.65_HC  | (54)  | YISGSTYYNPSLKSRITISVDTSKNQFSLKINSMTAADTAVYYCARDRETAGF |
| VH4-31       | (54)  | YYSGSTYYNPSLKSRVTISVDTSKNQFSLKLSSVTAADTAVYYCAR------- |
| Consensus    | (54)  | Y SGSTYYNPSLKSRITISVDTSKNQFSLKL SMTAADTAVYYCAR        |

——————— Section 2 ——— 106

|              |       | 107       119 |
|---|---|---|
| A15-3.65_HC  | (107) | DYWGQGTLVTVSS |
| VH4-31       | (107) | ------------- |
| Consensus    | (100) | ------------- |

——————— Section 3 ——— positives: 79.8% | identity: 77.3%

FIG. 24

```
                                                                    Section 1
               1                  10         20         30         40         53
A15-3.65_LC  (1) DIQMTQSPSSLSASVGDRVTITCQASQDINNYLNWYQQKPGKAPKLLIYDASN
        O8   (1) DIQMTQSPSSLSASVGDRVTITCQASQDISNYLNWYQQKPGKAPKLLIYDASN
Consensus    (1) DIQMTQSPSSLSASVGDRVTITCQASQDI NYLNWYQQKPGKAPKLLIYDASN
                                                                    Section 2
              54                  60         70         80         90        106
A15-3.65_LC (54) LETGVPSRFSGSGSGTDFTETISGLQPEDIATYYCQQYDTLPLTFGGGTKVEI
        O8  (54) LETGVPSRFSGSGSGTDFTFTISSLQPEDIATYYCQQYDNLP---------
Consensus   (54) LETGVPSRFSGSGSGTDFT TIS LQPEDIATYYCQQYD LP
                                                                    Section 3
             107
A15-3.65_LC (107) K
        O8   (96) -
Consensus   (107)
``` positives: 86.0%  identity: 86.0%

FIG. 25

```
                        1               10        20        30        40        50  53
A15-6.1_HC   (1)  QVQLVESGGGVVQPGRSLRLSCAASGFTFSSYAMHWVRQAPGKGLEWVAVISY
VH3-30       (1)  QVQLVESGGGVVQPGRSLRLSCAASGFTFSSYGMHWVRQAPGKGLEWVAVISY
Consensus    (1)  QVQLVESGGGVVQPGRSLRLSCAASGFTFSSY MHWVRQAPGKGLEWVAVISY
                                                                        Section 1

54         60        70        80        90       100  106
A15-6.1_HC  (54)  DGSNKYYADSVKGRFTISRDNSKNTLYLQMNSLRAEDTAVYYCARSIFGVVID
VH3-30      (54)  DGSNKYYADSVKGRFTISRDNSKNTLYLQMNSLRAEDTAVYYCAR-------
Consensus   (54)  DGSNKYYADSVKGRFTISRDNSKNTLYLQMNSLRAEDTAVYYCAR
                                                                        Section 2

107         122
A15-6.1_HC (107)  YGMDVWGQGTTVTVSS
VH3-30     (99)   ----------------
Consensus  (107)
                                     Section 3
``` positives: 80.3%   identity: 79.5%

FIG. 26

```
           1         10         20        30         40          54
A15-6.1_LC (1) DIQMTQSPSSLSASVGDRVTITCRASQGIRNYLAWYQQNPGKVPKLLIYGASTL
A20        (1) DIQMTQSPSSLSASVGDRVTITCRASQGISNYLAWYQQKPGKVPKLLIYAASTL
Consensus  (1) DIQMTQSPSSLSASVGDRVTITCRASQGI NYLAWYQQ PGKVPKLLIYAASTL
                                    Section 1

55        60        70        80         90        107
A15-6.1_LC (55) QSGVPSRFSGSGSGTDFTLTISSLQPEDVATYYCQKFSSPPFTFGPGTKVDIS
A20        (55) QSGVPSRFSGSGSGTDFTLTISSLQPEDVATYYCQKYNSAP----------
Consensus  (55) QSGVPSRFSGSGSGTDFTLTISSLQPEDVATYYCQKF S P
                                    Section 2
``` positives: 85.0%  identity: 83.2%

FIG. 27

```
                         1                10         20         30         40         50
A15-6.12_HC  (1)  QVQLEQSGPGLVKPSETLSLTCTVSGGSISSGTYHWSWIRQHPGRGLEWIGYI
VH4-31       (1)  QVQLQESGPGLVKPSQTLSLTCTVSGGSISSGGYYWSWIRQHPGKGLEWIGYI
Consensus    (1)  QVQL  SGPGLVKPS TLSLTCTVSGGSISSG YHWSWIRQHPGKGLEWIGYI
                  ──────────────────────────────────────────────── Section 1

54              60         70         80         90        106
A15-6.12_HC  (54) YYSGSTYHNPSLKSRITISVDTSKNQFSLKLSSVTAADTAVYYCARGGDGYRY
VH4-31       (54) YYSGSTYYNPSLKSRVTISVDTSKNQFSLKLSSVTAADTAVYYCAR------
Consensus    (54) YYSGSTYHVPSLKSRITISVDTSKNQFSLKLSSVTAADTAVYYCAR
                  ──────────────────────────────────────────────── Section 2

107     117
A15-6.12_HC (107) WGQGTLVTVSS
VH4-31      (100) -----------
Consensus   (107)
                  ────────── Section 3
``` positives: 81.2%   identity: 77.8%

FIG. 28

```
                                  1               10              20              30              40              53
              L2         (1)  EIVMTQSPATLSVSPGERATLSCRASQSVSNLAWYQQKPGQAPRLLIYGAST
              A15-6.12_LC (1)  EIVMTQSPATLSVSPGERATLSCRASQSISNNFAWYQQKPGQAPRLLIFGAST
              Consensus   (1)  EIVMTQSPATLSVSPGERATLSCRASQSIS N AWYQQKPGQAPRLLIFGAST
                                                                                  Section 1

54              60              70              80              90              106
              L2         (54) RATGIPARFSGSGSGTEFTLTISSLQSEDFAVYYCQQYNNWP----
              A15-6.12_LC (54) RATGIPARFSGSGSGTEFTLTISSLQSEDFAVYYCQQYNNWPRTFGQGTKVEI
              Consensus   (54) RATGIPARFSGSGSGTEFTLTISSLQSEDFAVYYCQQYNNWP
                                                                                  Section 2

107
              L2         (107) -
              A15-6.12_LC (107) K
              Consensus   (107)
                                                                                  Section 3
``` positives: 86.9%  identity: 85.0%

FIG. 29

```
                                    1              10            20             30              40            50  53
A15-6.2_HC  (1)  QVQLQESGPGLVKPSETLSLTCTVSGGSISTYYYWSWIRQPPGKGLEWIGYIYY
VH4-59      (1)  QVQLQESGPGLVKPSETLSLTCTVSGGSISSYYWSWIRQPPGKGLEWIGYIYY
Consensus   (1)  QVQLQESGPGLVKPSETLSLTCTVSGGSISSYYWSWIRQPPGKGLEWIGYIYY
                                                                              Section 1

54           60            70             80             90           100  106
A15-6.2_HC (54)  TGNTYYNPSLKSRVTMSVDTSKNQFSLKLNSVTAADTAVYYCARDPGQWLVPD
VH4-59     (54)  SGSTNYNPSLKSRVTISVDTSKNQFSLKISSVTAADTAVYYCAR--------
Consensus  (54)  SG T YNPSLKSRVTISVDTSKNQFSLKL SVTAADTAVYYCAR
                                                                              Section 2

107         121
A15-6.2_HC (107) AFDIWGQGTMVSVSS
VH4-59     (107) ---------------
Consensus   (98)
                                 Section 3
``` positives: 77.7% identity: 75.2%

FIG. 30

```
                                          Section 1
                    1                              54
A15-6.2_LC  (1)  DIVMTQSPLSLPVIPGEPASISCRSSQSLLQSNGNNYLDWYLQKPGQSPQLLIY
A19         (1)  DIVMTQSPLSLPVTPGEPASISCRSSQSLLHSNGYNYLDWYLQKPGQSPQLLIY
Consensus   (1)  DIVMTQSPLSLPV PGEPASISCRSSQSLL SNG NYLDWYLQKPGQSPQLLIY
                                          Section 2
                   55                             108
A15-6.2_LC (55)  LGSNRASGVPDRFSGSGSGTDFTLKISRVEADDVGIYYCMQALQIPLTFGGGTK
A19        (55)  LGSNRASGVPDRFSGSGSGTDFTLKISRVEAEDVGVYYCMQALQTP-------
Consensus  (55)  LGSNRASGVPDRFSGSGSGTDFTLKISRVEADDVGIYYCMQALQ P
                                          Section 3
                  109 112
A15-6.2_LC (109)  VEIK
A19        (101)  ----
Consensus  (109)
``` positives: 85.7% | identity: 83.9%

*FIG. 31*

```
                        1                  10                  20                  30                  40                  50  53
                                                                                                                      ──Section 1
A15-6.9_HC  (1)  QVQLEQSGPGLVKPSETLSLTCTVSGGSISSGTYHWSWIRQHPGRGLEWIGYI
VH4-31      (1)  QVQLQESGPGLVKPSQTLSLTCTVSGGSISSGGYYWSWIRQHPGKGLEWIGYI
Consensus   (1)  QVQL SGPGLVKPS TLSLTCTVSGGSISSG YYWSWIRQHPGKGLEWIGYI 54                  60                  70                  80                  90                 106
                                                                                                                      ──Section 2
A15-6.9_HC  (54) YYSGSTYHNPSLKSRTTISVDTSKNQFSLKLSSVTAADTAVYYCARGGDGYRY
VH4-31      (54) YYSGSTYYNPSLKSRVTISVDTSKNQFSLKLSSVTAADTAVYYCAR──────
Consensus   (54) YYSGSTYHNPSLKSRITISVDTSKNQFSLKLSSVTAADTAVYYCAR 107      117
                                                                                                                      ──Section 3
A15-6.9_HC  (107) WGQGTLVTVSS
VH4-31      (107) ───────────
Consensus   (100) 
``` positives: 81.2%  identity: 77.8%

FIG. 32

|  | | Section 1 |
|---|---|---|
| A15-6.11_HC | (1) | QVQLQESGPGLVKPSQTLSLTCTVSGGSTSSGTYHWTWIRQHPGKGLEWIGFI |
| VH4-31 | (1) | QVQLQESGPGLVKPSQTLSLTCTVSGGSISSGGYXWSWIRQHPGKGLEWIGYI |
| Consensus | (1) | QVQLQESGPGLVKPSQTLSLTCTVSGGSISSG YHWSWIRQHPGKGLEWIGFI |

|  | | Section 2 |
|---|---|---|
| A15-6.11_HC | (54) | YYSGSTYYNPSLKSRVTISVDTSKNQFSLKLSSVTAADTAVYYCARGGDGYKY |
| VH4-31 | (54) | YYSGSTYYNPSLKSRVTISVDTSKNQFSLKLSSVTAADTAVYYCAR------ |
| Consensus | (54) | YYSGSTYYNPSLKSRVTISVDTSKNQFSLKLSSVTAADTAVYYCAR |

|  | | Section 3 |
|---|---|---|
| A15-6.11_HC | (107) | WGQGTLVTVSS |
| VH4-31 | (107) | ----------- |
| Consensus | (100) | |
| Consensus | (107) | | positives: 83.8% | identity: 82.9%

FIG. 34

```
                        1         10        20        30        40        50 53
                        |         |         |         |         |         |  |
A15-6.11_LC    (1)   EIVMTQSPATLSVSPGERATLSCRASQSVSNNLAWYQQKPGQAPRLLIYGAST
         L2    (1)   EIVMTQSPATLSVSPGERATLSCRASQSVS SNLAWYQQKPGQAPRLLIYGAST
  Consensus   (1)   EIVMTQSPATLSVSPGERATLSCRASQSVS  NLAWYQQKPGQAPRLLIYGAST
                                                          Section 1

54        60        70        80        90       100 106
                        |         |         |         |         |         |  |
A15-6.11_LC   (54)   RATGIPARFSGSGSGTEFTLTISSLQSEDFAVYYCQQYNNWPRTFGQGTKVEI
         L2   (54)   RATGIPARFSGSGSGTEFTLTISSLQSEDFAVYYCQQYNNWP----------
  Consensus  (54)   RATGIPARFSGSGSGTEFTLTISSLQSEDFAVYYCQQYNNWP
                                                          Section 2

107
A15-6.11_LC  (107)    K
         L2   (96)    -
  Consensus (107)
                     Section 3
``` positives: 87.9% | identity: 87.9%

FIG. 35

| Clone # | VH | #del | VH End | #N's | N Sequence | DH | Size of D | D Sequence | #N's | N Sequence | JH | #del | JH Segment |
|---|---|---|---|---|---|---|---|---|---|---|---|---|---|
| A15-3.10 | DP-71/4-59 | 0 | GAGAGA | 8 | TCAGGGGC | D21-9 | 8 | AGTGGTTA | 7 | CTACCCG | JH3B | 0 | ATGCTT |
| A15-3.22 | DP-65/4-31 | 0 | GAGAGA | 9 | GGGAGATGG | - | - | - | - | - | JH4B | -4 | CTTTGA |
| A15-3.27 | DP-71/4-59 | 0 | GAGAGA | 8 | TCAGGGGC | D21-9 | 8 | AGTGGTTA | 7 | CTACCCG | JH3B | 0 | ATGCTT |
| A15-3.45 | DP-14/1-18 | 0 | GAGAGA | 6 | AACTAA | D3-10 | 12 | GGTTCGGGGAGT | 2 | CC | JH6B | -9 | ACTACT |
| A15-3.65 | DP-65/4-31 | 0 | GAGAGA | 8 | TCGGGAAA | D6-13 | 8 | CAGCTGGT | 4 | TTTT | JH5A | -11 | GACTAC |
| A15-6.1 | DP-49/3-30 | 3 | GAGAGA | 1 | T | D3-3 | 18 | CGATTTTGGAGTGGTTA | 3 | TCG | JH6B | -12 | ACTACG |
| A15-6.2 | DP-71/4-59 | 0 | GAGAGA | 7 | TCCAGGC | D6-19 | 11 | CAGTGGCTGGT | 5 | CCTG | JH3B | 0 | ATGCTT |
| A15-6.9 | DP-65/4-31 | 1 | CGAGAG | 3 | GGG | D5-24 | 11 | GAGATGGCTAC | 4 | AGAT | JH1 | -16 | ACTGGG |
| A15-6.11 | DP-65/4-31 | 1 | CGAGAG | 3 | GGG | D5-24 | 13 | GAGATGGCTACAA | 2 | GT | JH1 | -16 | ACTGGG |
| A15-6.12 | DP-65/4-31 | 1 | CGAGAG | 3 | GGG | D5-24 | 11 | GAGATGGCTAC | 4 | AGAT | JH1 | -16 | ACTGGG |

| Clone # | VK | #del | VH End | #N's | N Sequence | JK | #del | JK end |
|---|---|---|---|---|---|---|---|---|
| A15-3.10 | 02/012/DPK | 0 | CCCTCC | 9 | GGAGTGCAG | JK2 | -7 | TTTTGG |
| A15-3.22 | A30 | 3 | TTACCC | 0 | 0 | JK4 | 0 | GCTCAC |
| A15-3.27 | A30 | 3 | TTACCC | 0 | 0 | JK1 | 0 | GTGGAC |
| A15-3.45 | B3/DPK24 | 1 | TCCCTC | 3 | GGT | JK1 | -5 | CGTTCG |
| A15-3.65 | 08/018/DPK | 1 | TCCCTC | 0 | 0 | JK4 | -2 | TCACTTTC |
| A15-6.1 | A20/DPK4 | 3 | GTCCCC | 0 | 0 | JK3 | 0 | ATTCAC |
| A15-6.2 | A3/A19/DPK | 1 | TTCCTC | 0 | 0 | JK4 | -2 | TCACTTTC |
| A15-6.9 | L2/DPK21 | 1 | GGCCTC | 0 | 0 | JK1 | -2 | GGACGTT |
| A15-6.11 | L2/DPK21 | 1 | GGCCTC | 0 | 0 | JK1 | -2 | GGACGTT |
| A15-6.12 | L2/DPK21 | 1 | GGCCTC | 0 | 0 | JK1 | -2 | GGACGTT |

FIG. 36

USE OF ANTIBODIES AGAINST THE MUC18 ANTIGEN

RELATED APPLICATIONS

This application is a continuation of U.S. patent application Ser. No. 10/330,580, filed on Dec. 26, 2002, now abandoned which claims priority under 35 U.S.C. § 119(e) to U.S. Provisional Application Ser. No. 60/346,460, filed Dec. 28, 2001, both of which are hereby expressly incorporated by reference.

BACKGROUND OF THE INVENTION

1. Field of the Invention

Embodiments of the present invention concern antibodies binding MUC18 antigen as well as methods and means for making and using such antibodies.

2. Description of the Related Art

MUC18 is a cell-surface glycoprotein originally identified as a melanoma antigen, melanoma cell adhesion molecule (MCAM), whose expression is associated with tumor progression and the development of metastatic potential. MUC18 is a 113 kDA cell surface integral membrane glycoprotein composed of a signal peptide, five immunoglobulin-like domains, a transmembrane region, and a short cytoplasmic tail (Lehmann et al., Proc Natl Acad Sci USA, 86(24):9891–5 (1989)).

MUC18 is a member of the immunoglobulin superfamily and has significant sequence homology to a number of cell adhesion molecules of the Ig superfamily (Lehmann et al., Proc. Natl. Acad. Sci. USA, 86:9891–9895 (1989)), including BEN (Pourquie et al., Proc. Natl. Acad. Sci. USA, 89:5261–5265 (1992)), neural-cell adhesion molecule (N-CAM) (Owens et al., Proc. Natl., Acad. Sci. USA, 84:294–298 (1987)), myelin-associated glycoprotein (MAG) (Lai et al., Proc. Natl. Acad. Sci. USA, 84:4337–4341 (1987)), deleted in colorectal cancer (DCC) (Hedrick et al., Genes Devel, 8(10):1174–83 (1994)), and gicerin (Taira et al., Neuron, 12: 861–872 (1994)). The expression of MUC18 has been detected in relatively limited spectrum of normal human tissues and in a variety of malignant neoplasms. In normal adult tissues, MUC 18 is expressed on endothelial cells, smooth muscle cells (Shih et al., Lab. Invest., 75:377–388 (1996);Sers et al., Cancer Res., 54(21):5689–94 (1994)), a subpopulation of activated T lymphocytes (Pickl et al., J. Immunol., 158:2107–2115 (1997)) and intermediate trophoblasts (Shih et al., Lab. Invest., 75:377–388 (1996)). MUC18 is also expressed on a variety of malignant neoplasms including smooth muscle neoplasms (Leiomyomas and leiomyosarcomas), tumors of vascular origin (angiosarcomas and Kaposi's sarcomas), placental site trophoblastic tumors, choriocarcinomas and melanomas (Shih et al., Clinical Cancer Res., 2:569–575 (1996); Holzmann et al., Int. J. Cancer, 39:466–471 (1987)). The expression of MUC18 correlates directly with the metastatic potential of human melanoma cells (Bar-Eli, M., Cancer Metastasis, 18(3):377–85 (1999)).

A number of studies have identified MUC18 as a marker of tumor progression and metastasis in melanomas. The expression of MUC18 is absent in normal melanocytes and benign nevi but prominent on many primary melanomas and in most metastatic lesions (Lehmann et al., Proc. Natl. Acad. Sci. USA, 86:9891–9895 (1989); Lehmann et al., Cancer Res., 47:841–845 (1987); Shih et al., Cancer Res., 54:2514–2520 (1994)). Importantly, MUC18 expression correlates well with tumor vertical thickness and metastasis formation, and greater than 80% of metastatic lesions express MUC18 (Lehmann et al., Proc. Natl. Acad. Sci. USA, 86:9891–9895 (1989); Xie et al., Cancer Res., 57:2295–2303 (1997); Sers et al., Proc. Natl. Acad. Sci. USA, 90:8514–8518 (1993); Lehmann et al., Cancer Res., 47:841–845 (1987); Shih et al., Cancer Res., 54:2514–2520 (1994). A diagram depicting the expression of MUC18 with respect to other known molecular lesions in human melanoma is presented in FIG. 1.

The expression of the transcription factors ATF-1 and CREB is upregulated in metastatic melanoma cells. However, how overexpression of ATF-1/CREB contributes to the acquisition of the metastasis is unclear. CREB/ATF-1 may play an essential role in invasion by regulating the CRE-dependent expression of the adhesion molecule MUC18 and metalloproteinase MMP-2 (Jean et al., Mol. Cell Biochem., 212(1–2):19–28 (2000)) which belongs to the MMP family known to contribute to cancers and to have a role in tumor invasion, angiogenesis, and metastasis. Tumor cells are believed to utilize the matrix degrading capability of MMPs to spread to distant sites, and once the tumor cells have metastasized, MMPs are thought to promote the growth of these tumor cells. The role of MUC18 in melanoma tumor progression is not completely understood, but may include a role in one or more steps in the metastatic process possibly by affecting MMP-2 activation or cell migration.

The analysis of human melanoma cell lines showed a positive correlation of MUC18 expression with the ability of cells to produce metastases in nude mice (Johnson et al., Cancer Metastasis Rev., 18:345–357 (1999)). The generation of tumorigenic variants from a non-tumorigenic melanoma cell line was reported to be accompanied by induction of MUC18 expression (Luca et al., Melanoma Res., 3:35–41 (1993)). Expression of MUC18 on MUC18-negative human melanoma cell lines increased their tumorigenicity and enhanced their metastatic capability in experimental tumor models (Xie et al., Cancer Res., 57:2295–2303 (1997); Bani et al., Cancer Res., 56:3075–3086 (1996)). Finally, inhibition of MUC18 expression in metastases using genetic suppressor elements of MUC18 cDNA led to a decrease of the tumorigenic phenotype in nude mice (Styamoorthy et al., Oncogene, 20:4676 (2001)).

Although the function of MUC18 is not fully understood, several studies have demonstrated a role for this protein in mediating cell-cell and cell-matrix interactions by binding to an unidentified ligand (Shih et al., Cancer Res., 57:3835–3840 (1997); Johnson et al., Int. J. cancer, 73:769–774 (1997)). The expression of cell adhesion molecules which mediate cell-to-cell or cell-to-matrix interactions is a tumor cell property that is essential for metastases. Accordingly, MUC18-transfected melanoma cells showed increased homotypic adhesion, increased attachment to human endothelial cells, and increased invasion through Matrigel-coated filters suggesting a role in tumor invasion and trans-endothelial migration (Xie et al., Cancer Res., 57:2295–2303 (1997)). Importantly, anti-MUC18 antibodies were able to inhibit these functions in the MUC-18-transfected cells (Xie et al., Cancer Res., 57:2295–2303 (1997)).

Accordingly, there is a great need for anti-MUC18 antibodies that are able to inhibit the biological function of MUC18, most importantly cell proliferation and growth which may be essential to tumor progression and metastasis. Such antibodies would likely interfere with the inherent ability of MUC18 to mediate cell-cell and cell-matrix interactions. The inhibition of such activity may be possible with a monoclonal antibody targeted to MUC18. The ability to affect the progression of tumor cells expressing MUC18 on the cell surface may prove to be a treatment for patients with tumors or of use for prevention of metastatic disease in patients with such tumors.

SUMMARY OF THE INVENTION

The present invention is based on the development of monoclonal antibodies that were found to bind MUC18 and affect MUC18 function. This application describes human anti-MUC18 antibodies and anti-MUC18 antibody preparations with desirable properties from a therapeutic perspective, including strong binding affinity for MUC18, the ability to inhibit tumor growth and metastasis in vivo, the ability to promote cell survival, and the ability to inhibit tumor invasion in vitro.

In one aspect, the invention provides an anti-human MUC18 monoclonal antibody which binds to and neutralizes a biological activity of at least human MUC18 or stimulates the internalization and down-regulation of the protein. The antibody can significantly reduce or eliminate a biological activity of the human MUC18 in question.

One embodiment of the invention is a method of inhibiting tumor growth in an animal that includes: selecting an animal in need of treatment for a tumor; providing a monoclonal antibody comprising a heavy chain amino acid, wherein the antibody has an amino acid sequence selected from the group consisting of SEQ ID NOs: 1, 5, 9, 13, 17, 21, 25, 29, 33 and 37, and wherein the monoclonal antibody binds MUC18; and contacting the tumor with an effective amount of said antibody, wherein the contacting results in inhibited proliferation of said cells.

Another embodiment of the invention is a method of inhibiting cell invasion associated with melanoma by: selecting an animal in need of treatment for melanoma; providing a monoclonal antibody having a heavy chain amino acid, wherein the antibody has an amino acid sequence selected from the group consisting of SEQ ID NOs: 1, 5, 9, 13, 17, 21, 25, 29, 33 and 37, and wherein the monoclonal antibody binds MUC 18; and contacting the melanoma with an effective amount of the antibody, wherein the contacting results in inhibited cell invasion.

Yet another embodiment of the invention is a method of increasing survival of an animal having a metastatic tumor. This method includes: selecting an animal in need of treatment for a metastatic tumor; providing a monoclonal antibody comprising a heavy chain amino acid, wherein the antibody has an amino acid sequence selected from the group consisting of SEQ ID NOs: 1, 5, 9, 13, 17, 21, 25, 29, 33 and 37, and wherein the monoclonal antibody binds MUC18; and contacting said animal with an effective amount of the antibody, wherein the contacting results in inhibited metastasis of the tumor resulting in increased survival of the animal.

The biological activity of the subject human MUC18 may be cell proliferation. Further, the biological activity may include angiogenesis and cell proliferation important for primary tumor growth and metastasis, cell invasion and/or migration, and activation of metalloproteinase MMP-2. Even further, the biological activity may include growth and metastasis of tumor cells in patients with tumors, for example, melanoma.

Also provided is an isolated nucleic acid molecule encoding any of the antibodies described herein, a vector comprising the isolated nucleic acid molecule, a host cell transformed with the nucleic acid molecule, and a method of producing the antibody comprising culturing the host cell under conditions wherein the nucleic acid molecule is expressed to produce the antibody and optionally recovering the antibody from the host cell. The antibody may be of the IgG class. The isolated nucleic acid molecule preferably comprises a nucleotide sequence encoding a heavy chain variable domain of a monoclonal antibody, wherein said nucleotide sequence is selected from the group consisting of the nucleotide sequence of the heavy chain variable domain of c3.19.1 (SEQ ID NO: 3), c6.11.3 (SEQ ID NO: 7), C3.10 (SEQ ID NO: 11), C3.22 (SEQ ID NO: 15), C3.27 (SEQ ID NO: 19), C3.45 (SEQ ID NO: 23), C3.65 (SEQ ID NO: 27), C6.1 (SEQ ID NO: 31), C6.9 (SEQ ID NO: 35) or C6.2 (SEQ ID NO: 39), or a nucleotide sequence encoding a light chain variable domain of a monoclonal antibody, wherein said nucleotide sequence is selected from the group consisting of the nucleotide sequence of the light chain variable domain of 3.19.1 (SEQ ID NO: 4), 6.11.3 (SEQ ID NO: 8), C3.10 (SEQ ID NO:12), C3.22 (SEQ ID NO: 16), C3.27 (SEQ ID NO: 20), C3.45 (SEQ ID NO: 24), C3.65 (SEQ ID NO: 28), C6.1 (SEQ ID NO: 32), C6.9 (SEQ ID NO: 36), or C6.2 (SEQ ID NO: 40).

In a different aspect, the invention provides a method for the treatment of a disease or condition associated with the expression of MUC18 in a patient, comprising administering to the patient an effective amount of an anti-MUC18 antibody. The patient is a mammalian patient, preferably a human patient. The disease is a tumor, such as melanoma.

BRIEF DESCRIPTION OF THE DRAWINGS

FIGS. 3A and 3B are line graphs illustrating that neither the A375-SM (FIG. 3A) nor the WM-2664 cells (FIG. 3B) demonstrated a fluorescent shift when incubated in the presence of the control IgG2 Ab (bold line). However, when incubated in the presence of anti-MUC18 (dotted line), a strong shift in fluorescence intensity indicative of cell surface expression of the antigen was observed.

FIG. 6 shows the amino acid sequence of the variable region of the heavy (SEQ ID NO: 1) and light chain (SEQ ID NO: 2) and the nucleotide sequence encoding the variable region of the heavy (SEQ ID NO: 3) and light (SEQ ID NO: 4) chain of anti-MUC18 antibody, c3.19.1.

FIG. 7 shows the amino acid sequence of the variable region of the heavy (SEQ ID NO: 5) and light chain (SEQ ID NO: 6) and the nucleotide sequence encoding the variable region of the heavy (SEQ ID NO: 7) and light (SEQ ID NO: 8) chain of anti-MUC18 antibody, c6.11.3.

FIG. 8 shows the amino acid sequence of the variable region of the heavy (SEQ ID NO: 9) and light chain (SEQ ID NO: 10) and the nucleotide sequence encoding the variable region of the heavy (SEQ ID NO: 11) and light (SEQ ID NO: 12) chain of anti-MUC18 antibody, c3.10.

FIG. 9 shows the amino acid sequence of the variable region of the heavy (SEQ ID NO: 13) and light chain (SEQ ID NO: 14) and the nucleotide sequence encoding the variable region of the heavy (SEQ ID NO: 15) and light (SEQ ID NO: 16) chain of anti-MUC18 antibody, c3.22.

FIG. 10 shows the amino acid sequence of the variable region of the heavy (SEQ ID NO: 17) and light chain (SEQ ID NO: 18) and the nucleotide sequence encoding the variable region of the heavy (SEQ ID NO: 19) and light (SEQ ID NO: 20) chain of anti-MUC18 antibody, c3.27.

FIG. 11 shows the amino acid sequence of the variable region of the heavy (SEQ ID NO: 21) and light chain (SEQ ID NO: 22) and the nucleotide sequence encoding the variable region of the heavy (SEQ ID NO: 23) and light (SEQ ID NO: 24) chain of anti-MUC18 antibody, c3.45.

FIG. 12 shows the amino acid sequence of the variable region of the heavy (SEQ ID NO: 25) and light chain (SEQ ID NO: 26) and the nucleotide sequence encoding the variable region of the heavy (SEQ ID NO: 27) and light (SEQ ID NO: 28) chain of anti-MUC18 antibody, c3.65.

FIG. 13 shows the amino acid sequence of the variable region of the heavy (SEQ ID NO: 29) and light chain (SEQ ID NO: 30) and the nucleotide sequence encoding the variable region of the heavy (SEQ ID NO: 31) and light (SEQ ID NO: 32) chain of anti-MUC18 antibody, c6.1.

FIG. 14 shows the amino acid sequence of the variable region of the heavy (SEQ ID NO: 33) and light chain (SEQ ID NO: 34) and the nucleotide sequence encoding the variable region of the heavy (SEQ ID NO: 35) and light (SEQ ID NO: 36) chain of anti-MUC18 antibody, c6.9 (also independently cloned as c6.12).

FIG. 15 shows the amino acid sequence of the variable region of the heavy (SEQ ID NO: 37) and light chain (SEQ ID NO: 38) and the nucleotide sequence encoding the variable region of the heavy (SEQ ID NO: 39) and light (SEQ ID NO: 40) chain of anti-MUC18 antibody, c6.2.

FIG. 17 represents an alignment between the amino acid sequence of the variable region of the light chain of anti-MUC18 antibody, c3.10 (SEQ ID NO: 10), and the amino acid sequence encoding the O2 region (SEQ ID NO: 43) of the germline $V_k$ gene used. The consensus sequence (SEQ ID NO: 44) is represented below the alignment.

FIG. 18 represents an alignment between the amino acid sequence of the variable region of the heavy chain of anti-MUC18 antibody, c3.22 (SEQ ID NO: 13), and the amino acid sequence encoding the V4–31 region (SEQ ID NO: 45) of the germline $V_H$ gene used. The consensus sequence (SEQ ID NO: 46) is represented below the alignment.

FIG. 19 represents an alignment between the amino acid sequence of the variable region of the light chain of anti-MUC18 antibody, c3.22 (SEQ ID NO: 14), and the amino acid sequence encoding the A30 region (SEQ ID NO: 47) of the germline $V_k$ gene used. The consensus sequence (SEQ ID NO: 48) is represented below the alignment.

FIG. 20 represents an alignment between the amino acid sequence of the variable region of the heavy chain of anti-MUC18 antibody, c3.27 (SEQ ID NO: 17), and the amino acid sequence encoding the V4–59 region (SEQ ID NO: 49) of the germline $V_H$ gene used. The consensus sequence (SEQ ID NO: 50) is represented below the alignment.

FIG. 21 represents an alignment between the amino acid sequence of the variable region of the light chain of anti-MUC18 antibody, c3.27 (SEQ ID NO: 18), and the amino acid sequence encoding the A30 region (SEQ ID NO: 51) of the germline $V_k$ gene used. The consensus sequence (SEQ ID NO: 52) is represented below the alignment.

FIG. 22 represents an alignment between the amino acid sequence of the variable region of the heavy chain of anti-MUC18 antibody, c3.45 (SEQ ID NO: 21), and the amino acid sequence encoding the V1–18 region (SEQ ID NO: 53) of the germline $V_H$ gene used. The consensus sequence (SEQ ID NO: 54) is represented below the alignment.

FIG. 24 represents an alignment between the amino acid sequence of the variable region of the heavy chain of anti-MUC18 antibody, c3.65 (SEQ ID NO: 25), and the amino acid sequence encoding the 4–31 region (SEQ ID NO: 57) of the germline $V_H$ gene used. The consensus sequence (SEQ ID NO: 58) is represented below the alignment.

FIG. 25 represents an alignment between the amino acid sequence of the variable region of the light chain of anti-MUC18 antibody, c3.65 (SEQ ID NO: 26), and the amino acid sequence encoding the O8 region (SEQ ID NO: 59) of the germline $V_k$ gene used. The consensus sequence (SEQ ID NO: 60) is represented below the alignment.

FIG. 26 represents an alignment between the amino acid sequence of the variable region of the heavy chain of anti-MUC18 antibody, c6.1 (SEQ ID NO: 29), and the amino acid sequence encoding the V3–30 region (SEQ ID NO: 61) of the germline $V_H$ gene used. The consensus sequence (SEQ ID NO: 62) is represented below the alignment.

FIG. 27 represents an alignment between the amino acid sequence of the variable region of the light chain of anti-MUC18 antibody, c6.1 (SEQ ID NO: 30), and the amino acid sequence encoding the A20 region (SEQ ID NO: 63) of the germline $V_k$ gene used. The consensus sequence (SEQ ID NO: 64) is represented below the alignment.

FIG. 28 represents an alignment between the amino acid sequence of the variable region of the heavy chain of anti-MUC18 antibody, c6.12 (SEQ ID NO: 81), and the amino acid sequence encoding the V4–31 region (SEQ ID NO: 65) of the germline $V_H$ gene used. The consensus sequence (SEQ ID NO: 66) is represented below the alignment.

FIG. 29 represents an alignment between the amino acid sequence of the variable region of the light chain of anti-MUC18 antibody, c6.12 (SEQ ID NO: 82), and the amino acid sequence encoding the L2 region (SEQ ID NO: 67) of the germline $V_k$ gene used. The consensus sequence (SEQ ID NO: 68) is represented below the alignment.

FIG. 30 represents an alignment between the amino acid sequence of the variable region of the heavy chain of anti-MUC18 antibody, c6.2 (SEQ ID NO: 37), and the amino acid sequence encoding the V4–59 region (SEQ ID NO: 69) of the germline $V_H$ gene used. The consensus sequence (SEQ ID NO: 70) is represented below the alignment.

FIG. 31 represents an alignment between the amino acid sequence of the variable region of the light chain of anti-MUC18 antibody, c6.2 (SEQ ID NO: 38), and the amino acid sequence encoding the A19 region (SEQ ID NO: 71) of the germline $V_k$ gene used. The consensus sequence (SEQ ID NO: 72) is represented below the alignment.

FIG. 32 represents an alignment between the amino acid sequence of the variable region of the heavy chain of anti-MUC18 antibody, c6.9 (SEQ ID NO: 33), and the amino acid sequence encoding the V4–31 region (SEQ ID NO: 73) of the germline $V_H$ gene used. The consensus sequence (SEQ ID NO: 74) is represented below the alignment.

FIG. 34 represents an alignment between the amino acid sequence of the variable region of the heavy chain of anti-MUC18 antibody, c6.11.3 (SEQ ID NO: 5), and the amino acid sequence encoding the V4–31 region (SEQ ID NO: 77) of the germline $V_H$ gene used. The consensus sequence (SEQ ID NO: 78) is represented below the alignment.

FIG. 35 represents an alignment between the amino acid sequence of the variable region of the light chain of anti-MUC18 antibody, c6.11.3 (SEQ ID NO: 6), and the amino acid sequence encoding the L2 region (SEQ ID NO: 79) of the germline $V_k$ gene used. The consensus sequence (SEQ ID NO: 80) is represented below the alignment.

FIG. 36 represents a summary of the sequences comprising the V, D, J and resulting N recombination regions of the MUC18 antibody clones identified in the present invention. The D region sequences for MUC18 antibody clones A15–3.45 (SEQ ID NO: 85). A15–6.1 (SEQ ID NO: 86), A15–6.2 (SEQ ID NO: 87), A15–6.9 (SEQ ID NO: 88), A15–6.11 (SEQ ID NO: 89), and A15–6.12 (SEQ ID NO: 90) are shown.

DETAILED DESCRIPTION

A. Definitions

Figure 1:
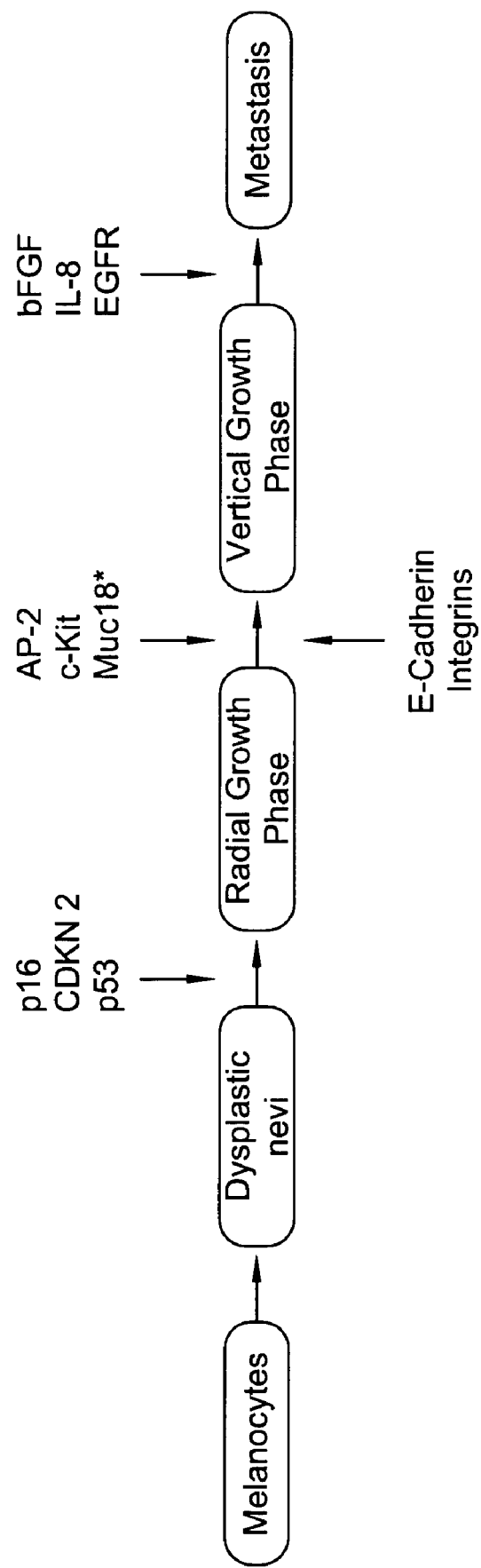
FIG. 1 is a diagram depicting the expression pattern of MUC18 and other known oncogenes and growth factors involved in melanoma tumor progression.

Unless defined otherwise, technical and scientific terms used herein have the same meaning as commonly understood by one of ordinary skill in the art to which this invention belongs. See, e.g. Singleton et al., *Dictionary of microbiology and Molecular Biology* $2^{nd}$ ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

As used herein, the term "MUC18" refers to the cell surface polypeptide that is a member of the immunoglobulin superfamily with sequence similarity to a number of cell adhesion molecules. MUC18 is also known in the art as "MCAM", "Mel-CAM", or "CD146". For purposes of this invention, from here on, "MUC18" is used to represent "MCAM", "Mel-CAM", and "CD 146".

The term "c3.19.1" as used herein refers to a fully human $IgG_2$ monoclonal antibody directed against the MUC18 antigen. The antibody was generated using XenoMouse® technology (Abgenix, Inc. Fremont, Calif.) and consists of human gamma 2 heavy and kappa light chains with a molecular weight of approximately 150 kDa. C3.19.1 is also herein referred to as ABX-MA1 and binds specifically to human MUC18 with high affinity (Kd=$6 \times 10^{-10}$ M).

The terms "biological activity" and "biologically active" with regard to MUC18 refer to the ability of a molecule to specifically affect tumor progression. Preferred biological activities include the ability to induce growth and metastasis of tumor cells. The effect of MUC18 on metastasis of tumor cells may include the ability to induce MMP-2 activation and/or cell migration. A further preferred biological activity is the ability to induce animal death due to tumor burden.

The terms "biological activity" and "biologically active" with regard to anti-MUC 18 antibodies refer to the ability of a molecule to inhibit the growth and metastasis of tumor cells often associated with MUC18 expression. Further, another metahcnism of action or activity for anti-MUC18 antibodies include the ability to stimulate MUC18 internalization and a consequent loss of cell surface expression. Specifically, the tumor cells include tumor cells in patients with tumors.

"Polymerase chain reaction" or "PCR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Pres, N.Y., 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, melanoma, carcinoma, lymphomma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Antibodies" (Abs) and "immunoglobulins" (Igs) are glycoproteeins having the same structural characteristics.

While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol* 186:651 (1985; Novotny and Haber, *Proc. Natl. Acad. Sci. U.S.A.* 82:4592 (1985); Chothia et al. *Nature* 342: 877–883 (1989)).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The "light chains" of antibodies (immunoglobulins) from any vertebrate species can be assigned to one of two clearly distinct types, called κ and λ, based on the amino acid sequences of their constant domains.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subuniit structures and three-dimensional configurations of different classes of immunoglobulins are well known.

The term "antibody" includes all classes and subclasses of intact immunoglobulins. The term "antibody" also covers antibody fragments. The term "antibody" specifically covers monoclonal antibodies, including antibody fragment clones.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody id directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al, *Nature*, 352:624–628 (1991) and Marks et al., *J. Mol. Biol.,* 222:581–597 (1991), for example.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other pertinacious or nonproteinaceous solutes. In preferred embodiments, the antibody will be purified (1) to greater than 95% by weight of antibody as determined by the Lowry method, and terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

By "neutralizing antibody" is meant an antibody molecule which is able to eliminate or significantly reduce an effector function of a target antigen to which is binds. Accordingly, a "neutralizing" anti-MUC18 antibody is capable of eliminating or significantly reducing an effector function which may include MUC18 dependent regulation of cell adhesion, migration or MMP activation. The antibody can affect the funtion of MUC18 by stimulating the internalization and degradation of the molecule thus effectively removing cell surface expression of the antigen.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991). The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24–34 (L1), 50–62 (L2), and 89–97 (L3) in the light chain variable domain and 31–55 (H1), 50–65 (H2) and 95–102 (H3) in the heavy chain variable domain; Kabat et al., *Sequences of Proteins of Immunological Interest*, 5$^{th}$ Ed. Public Health Service, National Institutes of Health, Bethesda, Md. (1991)) and/or those residues from a "hypervariable loop" (e.g. residues 26–32 (L1), 50–52 (L2) and 91–96 (L3) in the light chain variable domain and 26–32 ((H1), 53–55 (H2) and 96–101 (H3) in the heavy chain variable domain; Chothia and Lesk *J. Mol. Biol* 196:901–917 (1987)). "Framework Region" or "FR" residues are those variable domain residues other than the hypervariable region residues as herein defined.

The term "complementarity determining regions" or "CDRs" when used herein refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for (monoclonal or polyclonal) antibodies on protein antigens.

The term amino acid or amino acid residue, as used herein, refers to naturally occurring L amino acids or to D amino acids as described further below with respect to variants. The commonly used on- and three-letter abbreviations for amino acids are used herein (Bruce Alberts et al., *Molecular Biology of the Cell*, Garland Publishing, Inc., New York (3d ed. 1994)).

The term "disease state" refers to a physiological state of a cell or of a whole mammal in which an interruption, cessation, or disorder of cellular or body functions, systems, or organs has occurred.

The term "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from treatment of the present invention. This includes chronic and acute disorders or disease including those pathological conditions which predispose the mammal to the disorder in question. Non-limiting examples of disorders to be treated herein include benign and malignant tumors, leukemias and lymphoid malignancies, in particular prostate, renal, ovarian, stomach, endometrial, salivary gland, kidney, colon, thyroid, pancreatic, prostate or bladder cancer, and malignant tumors, such as cervical carcinomas and cervical intraepithelial squamous and glandular neoplasia, renal cell carcinoma (RCC), esophageal tumors, and carcinoma-derived cell lines. A preferred disorder to be treated in accordance with the present invention is renal and prostate cancer. An even further preferred disorder to be treated is melanoma.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Lipofection" refers to a practical nonviral method for introduction of genetic information into target tissues. Nonviral methods include chemical or physical methods. Lipofection uses an electrostatically bonded complex of positively charged lipids and negatively charged DNA as a vector which fuses with the cell membrane and delivers DNA into the cytoplasm. Lipofection differs from viral methods in that the efficiency of transfer of genetic information by lipofection is lower than by viral vectors and that the expression of the gene is transient. Alternatively, the complex of lipid and DNA is more stable and easier to handle when compared to viral vectors.

B. Methods for Carryying out One Embodiment of the Invention

1. Generation of anti-MUC18 Antibodies

A description follows as to exemplary techniques for the production of the antibodies used in accordance with the present invention.

(a) Monoclonal Antibodies

Monoclonal Antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as herein above described to elicit lymphocytes that produce or are capable of producing antibodies that will specifically bind to the protein used for immunization. Alternatively, cells expressing the antigen of interest may be used for immunization. Further alternatively, lymphocytes may be immunized in vitro. Animals are immunized against the immunogenic conjugates or derivatives by combing 1 mg or 1 μg of conjugate (for rabbits or mice, respectively) with 3 volumes of Freud's complete adjuvant and injecting the solution intradermally at multiple sites. One month later, the animals are boosted with 1/5 to 1/0 the original amount of conjugate in Freud's complete adjuvant by subcutaneous injection at multiple sites. 7 to 14 days later the animals are bled and the serum is assayed for anti-MUC18 antibody titer. Antibodies are boosted until the titer plateaus. Preferably, the animal is boosted with the conjugate of the same MUC18 antigen, but conjugated to a different protein and/or through a different cross-linking agent. Conjugates also can be made in recombinant cell culture as protein fusions. Also, aggregating agents such as alum are used to enhance the immune response.

Lymphocytes or more preferably, lymphocytes enriched for B cells isolated from such immunized animals are then fused with myeloma cells by an electrocell fusion process or by using a suitable fusing agent, such as polyethylene glycol, to form a hybridoma cell (Goding, *Monoclonal Antibodies: Principles and Practice*, pp. 59–109, [Academic Press, 1996]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC11 mouse tumors available from the Salk Institute Cell Distribution Center, San Diego, Calif. USA, and SP-2 or X63-Ag8–653 cells available from the American Type Culture Collection, Rockville, Md. USA. Human myeloma and mouse-human heteromyeloma cell lines also have been described for the production of human monoclonal antibodies (Kozbor, *J. Immunol.* 133: 3001 (1984); Brodeur et al., *Monoclonal Antibody Production Techniques and Applications*, pp. 51–63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp.59–103, Academic Press, 1996). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatiite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by covalently joining to the immunoglobulin coding sequence all or part of the coding sequence for a non-immunoglobulin polypeptide. In that manner, "chimeric" or "hybrid" antibodies are prepared that have the binding specificity of an anti-MUC18 monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an MUC18 and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

(b) Human Antibodies

Attempts to use the same technology for generating human mAbs have been hampered by the lack of a suitable human myeloma cell line. The best results were obtained using heteromyelomas (mouse×human hybrid myelomas) as fusion partners (Kozbor, *J. Immunol.* 133: 3001 (1984); Brodeur, et al., *Monoclonal Antibody Production Techniques and Applications*, pp.51–63, Marcel Dekker, Inc., New York, 1987). Alternatively, human antibody-secreting cells can be immortalized by infection with the Epstein-Barr virus (EBV). However, EBV-infected cells are difficult to clone and usually produce only relatively low yields of immunoglobulin (James and Bell, *J. Immunol. Methods* 100: 5–40 [1987]). In the future, the immortalization of human B cells might possibly be achieved by introducing a defined combination of transforming genes. Such a possibility is highlighted by a recent demonstration that the expression of the telomerase catalytic subunit together with the SV40 large T oncoproteiin and an oncogenic allele of H-ras resulted in the tumorigenic conversion of normal human epithelial and fibroblast cells (Hahn et al., *Nature* 400: 464–468 [1999]).

It is now possible to produce transgenic animals (e.g. mice) that are capable, upon immunization, of producing a repertoire of human antibodies in the absence of endogenous immunoglobulin production (Jakobovits et al., *Nature* 362: 255–258 [1993]; Lonberg and Huszar, *Int. Rev. Immunol.* 13: 65–93 [1995]; Fishwild et al., *Nat. Biotechnol.* 14: 845–851 [1996]; Mendez et al., *Nat. Genet.* 15: 146–156 [1997]; Green, *J. Immunol. Methods* 231: 11–23 [1999]; Tomizuka et al., *Proc. Natl. Acad. Sci. USA* 97: 722–727 [2000]; reviewed in Little et al., *Immunol. Today* 21: 364–370 [2000]). For example, it has been described that the homozygous deletion of the antibody heavy chain joining region ($J_H$) gene in chimeric and germ-line mutant mice results in complete inhibition of endogenous antibody production (Jakobovits et al., *Proc. Natl. Acad. Sci. USA* 90: 2551–2555 [1993]). Transfer of the human germ-line immunoglobulin gene array in such germ-line mutant mice results in the production of human antibodies upon antigen challenge (Jakobovits et al., *Nature* 362: 255–258 [1993]).

Mendez et al. (*Nature Genetics* 15: 146–156 [1997]) have generated a line of transgenic mice designated as "XenoMouse® II" that, when challenged with an antigen, generates high affinity fully human antibodies. This was achieved by germ-line integration of megabase human heavy chain and light chain loci into mice with deletion into endogenous $J_H$ segment as described above. The XenoMouse® II harbors 1,020 kb of human heavy chain locus containing approximately 66 $V_H$ genes, complete $D_H$ and $J_H$ regions and three different constant regions (μ, δ and γ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Techniques for generating antibodies using Abgenix's XenoMouse® technology include injection of a particular antigen of interest into such mice. Sera from such immunized animals may be screened for antibody-reactivity against the initial antigen. Lymphocytes may be isolated from lymph nodes or spleen cells and may further be selected for B cells by selecting for CD138-negative and CD19+ cells. The B cell cultures (BCCs) may be either fused to myeloma cells to generate hybridomas as detailed above or screened further for reactivity against the initial antigen. Such screening includes ELISA.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

In a preferred embodiment, the antibodies of the present invention comprise an anti-human MUC18 monoclonal antibody heavy chain or a fragment thereof, comprising the following CDR's (as defined by Kabat et al, *Sequences of Proteins of Immunological Interest*, Fifth Edition, NIH Publication 91–3242, Bethesda Md. (1991), vols 1–3): (a) CDR1, (b) CDR2 and (c) CDR3. The heavy chain of the antibodies in one embodiment of the present invention comprise of the following sequences: SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 29, SEQ ID NO: 33 or SEQ ID NO: 37.

In yet another embodiment, the invention provides an anti-human MUC18 monoclonal antibody light chain or a fragment thereof, comprising the following CDRs: (a) CDR1, (b) CDR2 and (c) CDR3. The light chain of the antibodies in one embodiment of the present invention comprise of the following sequences: SEQ ID NO: 2, SEQ ID NO: 6, SEQ ID NO: 10; SEQ ID NO: 14, SEQ ID NO: 18; SEQ ID NO: 22; SEQ ID NO: 26; SEQ ID NO: 30; SEQ ID NO: 34; or SEQ ID NO: 38.

In one aspect, the present invention includes anti-MUC18 antibodies such as c3.19.1 and c6.11.3. The heavy chain amino acid and nucleotide sequences of c3.19.1 are encoded by SEQ ID NO: 1 and 3, respectively, and the heavy chain amino acid and nucleotide sequence of c6.11.3 are encoded by 5 and 7, respectively. The light chain amino acid and nucleotide sequences of c3.1.9.1. are encoded by SEQ ID NO: 2 and 4, respectively, and the light chain amino acid and nucleotide sequences of c6.11.3 are encoded by 6 and 8, respectively.

2. Screening for Antibodies with the Desired Properties

Techniques for generating antibodies have been described above. One may further select antibodies with certain biological characteristics, as desired.

In one embodiment of the invention, melanoma cells were used for analysis of anti-MUC18 antibody function. The melanoma cells were derived from a number of sources and possessed a variety of characteristics that could potentially contribute to the metastatic phenotype. Their phenotypes are presented in Table 1.

TABLE 1

Properties of Melanoma Cells Used for Studies

| Cell Line | Origin | Metastatic Capacity | MUC18 Expression |
| --- | --- | --- | --- |
| A375-SM | Selection from animal model of metastasis | High | High |
| SB-2 | Cutaneous melanoma | Non-metastatic | Negative |
| TXM-13 | Brain metastasis | High | High |
| WM-2664 | Metastasis from cutaneous melanoma | High | Medium |

(a) Binding to MUC18 Antigen

For example, to identify anti-MUC18 antibodies with high affinity for human MUC18, kinetic measurements and binding affinity of the anti-MUC18 antibodies were obtained from Biacore experiments. The Biacore experiments measured the affinity of MUC18 antibodies captured on a protein A surface for labeled MUC18 antigen and are further described in the examples below. Anti-MUC18 antibodies with a Kd of $6 \times 10^{-10}$M were considered high affinity anti-MUC18 antibodies.

In a further example, to determine whether anti-MUC18 antibodies of the present invention were able to recognize denatured MUC18 in human melanoma cells, the antibodies were used for immunoblots of metastatic melanoma cells and non-metastatic melanoma cells (control). Those antibodies which were able to detect MUC18 in metastatic melanoma cells were selected as anti-MUC18 antibodies of interest.

Further, to identify anti-MUC18 antibodies that recognized the native form of the MUC18 protein on the surface of cells, flow cytometry analysis wasperformed. According to this assay, cells expressing the antigen of interest were detached from cell culture plates, incubated with either an isotype-matched control human antibody or the anti-MUC18 antibody for 20 minutes at 4° C. After washing, all samples were incubated with phycoerythrin-conjugated F(ab')$_2$ fragments of Goat Anti-Human IgG (H+L) (Jackson) for 20 minutes at 4° C. in the dark. After several washings, the cells were resuspended in FACS buffer and analyzed by cytofluorometry. Those antibodies which shift the fluorescence intensity when compared to control antibodies were selected as anti-MUC18 antibodies of interest.

(b) Inhibition of tumor growth

Further, to select tumor growth inhibitory anti-MUC18 antibodies, antibodies were screened for their ability to inhibit tumor growth in animal models. In one embodiment, the growth inhibitory antibody of choice was able to inhibit the growth of WM-2664 tumor cells when grown subcutaneously. To evaluate the effect of anti-MUC18 antibody treatment on the growth of a subcutaneous tumor, exponentially growing WM-2664 cells were harvested, resuspended, and injected into the flanks of male BALB/c nude mice. Beginning on Day 3 after implantation, animals were treated with either 0.1 mg or 1 mg anti-MUC18 antibody or 0.1 mg control human antibody once a week. Tumor growth was monitored weekly. Those antibodies which inhibited the growth of WM-2664 tumor cells in vivo were selected as tumor growth inhibitory antibodies.

To select tumor growth inhibitory anti-MUC18 antibodies, antibodies were screened for the ability to inhibit the proliferation of tumor cells in culture. To screen for such antibodies, cells expressing various levels of MUC18 were incubated in the presence of anti-MUC18 for a 4–5 day period. On each day of the experiment, the number of cells in triplicate wells were determined using a dimethylthiazole diphenyl tetrazolium bromide (MTT) assay. Following incubation in MTT, cell were lysed. The conversion of MTT to formazan by metabolically viable cells was monitored at 570 nm. The ability of anti-MUC18 antibodies to affect the cell growth or viability in this assay was determined.

It is well known in the art that inhibition of MUC18 activity is important for the three-dimensional growth of melanoma tumor cells in vivo, but not in cell culture (Satyamoorthy et al., *Oncogene*, 20:4676 (2001)). The anti-MUC18 antibodies of the present invention were tested to determine whether they had an effect on melanoma cell proliferation in vitro. Cells expressing various levels of MUC18 were incubated in the presence of anti-MUC18 antibody for 1 4–5 day period. On each day of the experiment, the number of cells in triplicate wells was determined using a dimethylthiazole diphenyl tetrazolium bromide (MTT) assay. Following incubation for two hours in medium containing MTT, the medium was removed, and the cells lysed. The conversion of MTT to formazan by metabolically viable cells was monitored. The anti-MUC18 antibodies (c3.19.1) did not affect cell growth or viability, a characteristic supported by the art.

(c) Inhibition of Metastasis

To select for metastasis inhibitory anti-MUC18 antibodies, antibodies were screened for the ability to inhibit metastasis in animal models. In one embodiment, the metastasis inhibitory antibody of choice was able to inhibit the formation of lung metastases of melanoma A375-SM and WM-2664 cells in vivo. To evaluate the effect of anti-MUC18 antibody treatment on the metastasis of melanoma cells that were injected into nude mice, exponentially growing A375-SM and WM-2664 melanoma cells were harvested, resuspended, and injected into the lateral tail vein of mice. Mice were treated with anti-MUC18 antibody beginning on Day 3 and once weekly thereafter. The mice were sacrificed 6–8 weeks later. After fixing and staining with Bouin's solution, lung nodules were counted with the aid of a dissecting microscope. Those antibodies which inhibited lung metastases in animals injected with tumor cells were selected as metastasis inhibitory antibodies.

In a more extensive experiment, exponentially growing A375SM cells were harvested on Day 0, resuspended and injected into the lateral tail veins of female nude mice. The animals were treated one day prior to tumor cell injection and once a week thereafter with a specific dose of anti-MUC18 antibody. All animals were sacrificed after 6 weeks at which time the lungs were removed and the tumor nodules were counted with the aid of a dissecting microscope. Those antibodies which inhibited melanoma metastasis into the lung in a dose-dependent manner were selected as metastasis inhibitory antibodies.

(d) Promotion of Animal Survival

To select for antibodies which increase the survival of animals bearing metastatic melanoma tumors, antibodies were screened for the ability to increase the survival of mice bearing tumors. WM-2664 human melanoma tumor cells in their exponential phase were harvested, resuspended in suitable buffer, and injected into the lateral tail vein of male BALB/c nude mice. After administration of anti-MUC18 antibody or control antibody intraperitoneally at 1 mg or 0.2 mg per mouse on a weekly basis, mice were monitored daily for survival. Those antibodies which demonstrated a dose dependent increase in survival of the mice were selected as survival prolonging antibodies.

(e) Inhibition of Melanoma Cell Invasion

Melanoma metastasis is closely associated with MUC18 expression. One of the phenotypic changes often associated with metastasis is the ability of cells to migrate and invade through the extracellular matrix.

To select for antibodies that influence the ability of MUC18 expressing cells to invade and migrate through the extracellular matrix, antibodies were screened for their ability to inhibit the ability of cells to migrate and invade through Matrigel coated membranes. To identify such antibodies, cells expressing MUC18 were seeded into plates and allowed to attach. The growth medium were then removed and replaced with fresh growth medium containing either control antibody or anti-MUC18 antibody. After a period of 5 days, the cells were detached from the plates and placed in the upper chamber of a Matrigel coated membrane in serum-free medium containing either control or anti-MUC18 antibody. Following an incubation period, the cells remaining in the upper chamber were removed by scraping and the bottom filter subjected to staining. The matrices were then mounted on slides and the cells that had migrated across the membrane were counted. Those antibodies which demonstrated an inhibitory effect on the ability of melanoma cells to digest the extracellular matrix and migrate toward the chemoattractant on the opposite side were selected as invasion inhibitory antibodies.

3. Therapeutic Compositions and Mode of Administration of Anti-MUC18 antibodies

Therapeutic formulations of the anti-MUC18 antibodies of the invention are prepared for storage by mixing antibody having the desired degree of purity with optional physiologically acceptable carriers, excipients, or stabilizers (*Remington: The Science and Practice of Pharmacy*, 19th Edition, Alfonso, R., ed, Mack Publishing Co. (Easton, Pa.: 1995)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The anti-MUC18 antibody to be used for in vivo administration must be sterile. This is readily accomplished by filtration through sterile filtration membranes, prior to or following lyophilization and reconstitution. The anti-MUC18 antibody ordinarily will be stored in lyophilized form or in solution.

Therapeutic anti-MUC18 antibody compositions generally are placed into a container having a sterile access port, for example, an intravenous solution bag or vial having a stopper pierceable by a hypodermic injection needle.

The route of anti-MUC18 antibody administration is in accord with known methods, e.g. injection or infusion by intravenous, intraperitoneal, intracerebral, subcutaneous, intramuscular, intraocular, intraarterial, intracerebrospinal, or intralesional routes, or by sustained release systems as noted below. Preferably the antibody is given systemically.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547–556 (1983)), poly (2-hydroxyethyl-methacrylate) (Langer et al., *J. Biomed. Mater. Res.,* 15: 167–277 (1981) and Langer, *Chem. Tech.,* 12: 98–105 (1982)), ethylene vinyl acetate (Langer et al., supra) or poly-D-(−)-3-hydroxybutyric acid (EP 133,988). Sustained-release anti-MUC18 antibody compositions may also include liposomally entrapped antibody. Liposomes containing antibody are prepared by methods known per se: DE 3,218,121; Epstein et al., *Proc. Natl. Acad. Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese patent application 83–118008; U.S. Pat. No. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal antibody therapy.

Anti-MUC18 antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-MUC18 antibody can be aerosolized using a fluorocarbon formulation and a metered dose inhaler, or inhaled as a lyophilized and milled powder.

An "effective amount" of anti-MUC18 antibody to be employed therapeutically will depend, for example, upon the therapeutic objectives, the route of administration, the type of anti-MUC18 antibody employed, and the condition of the patient. Accordingly, it will be necessary for the therapist to titer the dosage and modify the route of administration as required to obtain the optimal therapeutic effect. Typically, the clinician will administer the anti-MUC18 antibody until a dosage is reached that achieves the desired effect. The progress of this therapy is easily monitored by conventional assays.

Antibodies specific to tumor antigens such as anti-MUC18 are useful in targeting of tumor cells for destruction. For example, ricin, a cellular toxin derived from plants, is finding unique applications, especially in the fight against tumors and cancer. Implications are being discovered as to the use of ricin in the treatment of tumors. Ricin has been suggested to have a greater affinity for cancerous cells than normal cells (Montfort et al. 1987) and has been often termed as a "magic bullet" for targeting malignant tumors. Toxins such as ricin remain active even if the B chain of the toxin is removed. Accordingly, if the solitary A chain is coupled to a tumor-specific antibody, such as anti-MUC18 antibody, the toxin has a specific affinity for cancerous cells over normal cells (Taylorson 1996). For example, ricin immunotoxin has been developed to target the CD5 T-cell antigen often found in T-cell and B-cell malignancies (Kreitman et al. 1998). Further, the linking of such anti-MUC18 antibodies to radioisotopes provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. With this "magic bullet," the patient can be treated with much smaller quantities of radioisotopes than other forms of treatment available today. Most commonly antibodies are conjugated with potent chemotherapeutic agents such as maytansine, geldanamycin or calichaemycin for delivery to tumors (Frankel et al., *Cancer Biotherapy and Radiopharmaceuticals,* 15:459–476 (2000); Knoll et al., *Cancer Res.,* 60:6089–6094 (2000); Liu et al., *Proc. Natl. Acad. Sci. USA,* 93:8618–8623 (1996); Mandler et al., *J. Natl. Cancer Inst.,* 92:1573–1581 (2000); and Ota et al., *Int. J. Clin. Oncol.,* 4:236–240 (1999). These drugs are too toxic to be administered on their own. When conjugated to a therapeutic antibody such as MUC18, their biological activity can be directed specifically to the tumor cells. Accordingly, antibodies, such as MUC18 antibodies, can be modified to act as immunotoxins utilizing techniques that are well known in the art. See e.g., Vitetta et al., *Immunol. Today,* 14:252 (1993) and U.S. Pat. No. 5,194,594. In connection with the preparation of radiolabeled antibodies, such modified antibodies can also be readily prepared utilizing techniques that are well known in the art. See e.g., Junghans et al., *Cancer Chemotherapy and Biotherapy,* pgs. 655–686 (second edition, Chafner and Longo, eds., Lippincott Raven (1996)) and U.S. Pat. Nos. 4,681,581, 4,735,210, 5,101,827, 5,102,990, 5,648,471, and 5,697,901. The immunotoxins and radiolabeled molecules would be likely to kill cells expressing MUC18, and particularly those cells in which the antibodies of the invention are effective.

The patients to be treated with the anti-MUC18 antibody of the invention include patients with tumors, preferably melanoma and/or prostate or renal cancer. Other tumors include esophageal, pancreatic, colorectal tumors, carcinomas, such as renal cell carcinoma (RCC), cervical carcinomas and cervical intraepithelial squamous and glandular neoplasia, and cancers, such as colorectal cancer, breast cancer, lung cancer, and other malignancies. Patients are candidates for therapy in accord with this invention until such point as no healthy tissue remains to be protected from tumor progression. It is desirable to administer an anti-MUC18 antibody as early as possible in the development of the tumor, and to continue treatment for as long as is necessary.

In the treatment and prevention of tumor-associated disorder by an anti-MUC18 antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the disorder, including treating chronic autoimmune conditions and immunosuppression maintenance in transplant recipients. Such amount is preferably below the amount that is toxic to the host or renders the host significantly more susceptible to infections.

As a general proposition, the initial pharmaceutically effective amount of the antibody administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of antibody, depending on the pattern of pharmacokinetic decay that the practitioner wishes to achieve.

As noted above, however, these suggested amounts of antibody are subject to a great deal of therapeutic discretion. The key factor in selecting an appropriate dose and scheduling is the result obtained, as indicated above. For example, the antibody may be optionally formulated with one or more agents currently used to prevent or treat tumors such as standard- or high-dose chemotherapy and hematopoietic stem-cell transplantation. The effective amount of such other agents depends on the amount of anti-MUC18 antibody present in the formulation, the type of disorder or treatment, and other factors discussed above. These are generally used in the same dosages and with administration routes as used hereinbefore or about from 1 to 99% of the heretofore employed dosages.

Further details of the invention can be found in the following example, which further defines the scope of the invention. All references cited throughout the specification, and the references cited therein, are hereby expressly incorporated by reference in their entirety.

EXAMPLE 1

Preparation of MUC18 Antigens

In the present study, recombinant MUC18 proteins were prepared. The extracellular domain (ECD) (aa#1–559) of human MUC18 was cloned from SK-MEL-28 cells (ATCC HTB-72) by Reverse Transcriptase-PCR (RT-PCR) with primers that incorporate an EcoRI site in the forward primer and an NheI site in the reverse primer based on the published NCBI sequence (Accession # NM_006500).

The primers used for the amplification of the ECD of MUC18 were as follows:
Forward primer: 5'-ATATTACGAATTCACTTGCGTCTCGCCCTCCGG-3'(SEQ ID NO :83) Reverse primer: 5'-CAGCTTAGAGCTAGCCGGCTCTCCGGCTCCGGCA-3'(SEQ ID NO:-14 84)

EXAMPLE 2

Anti-MUC18 Antibodies

A. Antibody Generation
1. Immunization and Selection of Animals for Harvesting by ELISA Monoclonal antibody against MUC18 was developed by sequentially immunizing XenoMouse mice (XenoMouse G2, Abgenix, Inc. Fremont, Calif.). The initial immunization was with $5 \times 10^6$ SK-MEL-28 cells admixed 1:1 v/v with Complete Freund's Adjuvant (CFA). Subsequent boosts were made first with $5 \times 10^6$ SK-MEL-28 cells admixed 1:1 v/v with Incomplete Freund's Adjuvant (IFA), followed by four injections with 5 μg soluble MUC18-human IgG$_2$ Fc fusion protein admixed 1:1 v/v with IFA, and then a final boost of 10 μg soluble MUC18-human IgG$_2$ Fc fusion protein without adjuvant. In particular, each mouse was immunized either at the base of the tail by intraperitoneal injection or via hind footpad injection with MUC18 recombinant antigen followed by the generation of a large number of candidate mAbs, and the screening of antibodies for binding and activity.

The mice were initially injected with MUC18 antigen at a concentration of 1–5 μg/mouse. Each mouse was further immunized into each hind footpad 6 additional times (at 3–4 day intervals) with soluble antigen, specifically 5 μg of soluble MUC18-human IgG2 Fc fusion protein in DPBS admixed 1:1 v/v with IFA then a final boost of 10 μg soluble MUC18-human IgG2 Fc fusion protein in DPBS without adjuvant. The animals were immunized on days 0, 4, 7, 10, 14, 17 and 20 and four days later on day 4, fusions were performed. For the fusions, the mice were euthanized, and inguinal and popliteal lymph nodes were recovered.

Lymphocytes from the immunized XenoMouse mice were released by mechanical disruption of the lymph nodes using a tissue grinder and then depleted of T cells by CD90 negative selection. The fusion was performed by mixing washed enriched B cells and non-secretory myeloma P2X63Ag8.653 cells purchased from ATCC (Cat. #CRL 1580) (Kearney et al., *J. Immunol.*, 123:1548–1550 (1979)) at a ratio of 1:1. The cell mixture was gently subjected to

```
Forward primer: 5'-ATATTACGAATTCACTTGCGTCTCGCCCTCCGG-3'      (SEQ ID NO: 83)

Reverse primer: 5'-CAGCTTAGAGCTAGCCGGCTCTCCGGCTCCGGCA-3'    (SEQ ID NO: 84)
```

MUC18 cDNA was amplified (Gene Amp XL PCR kit, Perkin Elmer) from RNA (RNAzol,Tel Test, INC) prepared from SK-MEL-28 cells (ATCC HTB-72). For construction of a V5-HIS or HuIgG2 fusion protein, the 1700 bp PCR product encoding amino acids 1–559 was digested with EcoRI and NheI and ligated into CD147HuIgG2DHFR vector (ABGX) digested with EcoRI and NheI or pcDNA3.1V5HISB vector (Invitrogen) digested with EcoRI and XbaI. The resulting plasmids were transfected in 293 cells by CaPO$_4$ method, and then, the fusion protein was purified from harvested conditioned media via ProteinA chromatography (MUC18-HuIgG2) or Ni-NTA chromatography (MUC18-V5HIS).

The MUC18 ECD contained 4 amino acid differences from the published NCBI sequence: #383 D>G,#390 P>L, #424 K>N, and #425 L>V.

centrifugation at 800 g. After complete removal of the supernatant, the cells were treated with 2–4 mL of Pronase solution (CalBiochem, Cat. #53702; 0.5 mg/mL in PBS) for no more than 2 minutes. Then 3–5 ml of FBS was added to stop the enzyme activity, and the suspension was adjusted to 40 mL total volume using electro cell fusion solution, ECFS (0.3M Sucrose, Sigma, Cat# S7903; 0.1 mM Magnesium Acetate, Sigma, Cat. #M2545; 0.1 mM Calcium Acetate, Sigma, Cat# C4705). The supernatant was removed after centrifugation and the cells were resuspended in 40 mL ECFS. This wash step was repeated, and the cells again were resuspended in ECFS to a concentration of 2×106 cells/mL. Electro-cell fusion was performed using a fusion generator, model ECM2001, Genetronic, Inc., San Diego, Calif.

After fusion, the cells were resuspended in DMEM (JRH Biosciences), 15% FCS (Hyclone), containing HAT, and supplemented with L-glutamine, pen/strep, OPI (oxaloacetate, pyruvate, bovine insulin) (all from Sigma) and IL-6 (Boehringer Mannheim) for culture at 37° C. and 10% $CO_2$ in air. Cells were plated in flat-bottomed 96-well tissue culture plates at $4\times10^4$ cells per well. Cultures were maintained in HAT (hypoxanthine, aminopterin and thymidine) supplemented media for 2 weeks before transfer to HT (hypoxanthine and thymidine) supplemented media. Hybridomas were selected for by survival in HAT medium and supernatants from those wells containing hybridomas were screened for antigen reactivity by ELISA. The ELISA format entailed incubating supernatants on antigen coated plates and detecting human anti-MUC18 binding using horseradish peroxidase (HRP) labeled mouse anti-human IgG2.

Cloning was performed on selected antigen-positive wells using limited dilution plating. Plates were visually inspected for the presence of single colony growth and supernatants from single colony wells then screened by antigen-specific ELISA as described above. Highly reactive clones were assayed to verify purity of human gamma and kappa chain by multiplex ELISA using a Luminex instrument.

Figure 16:
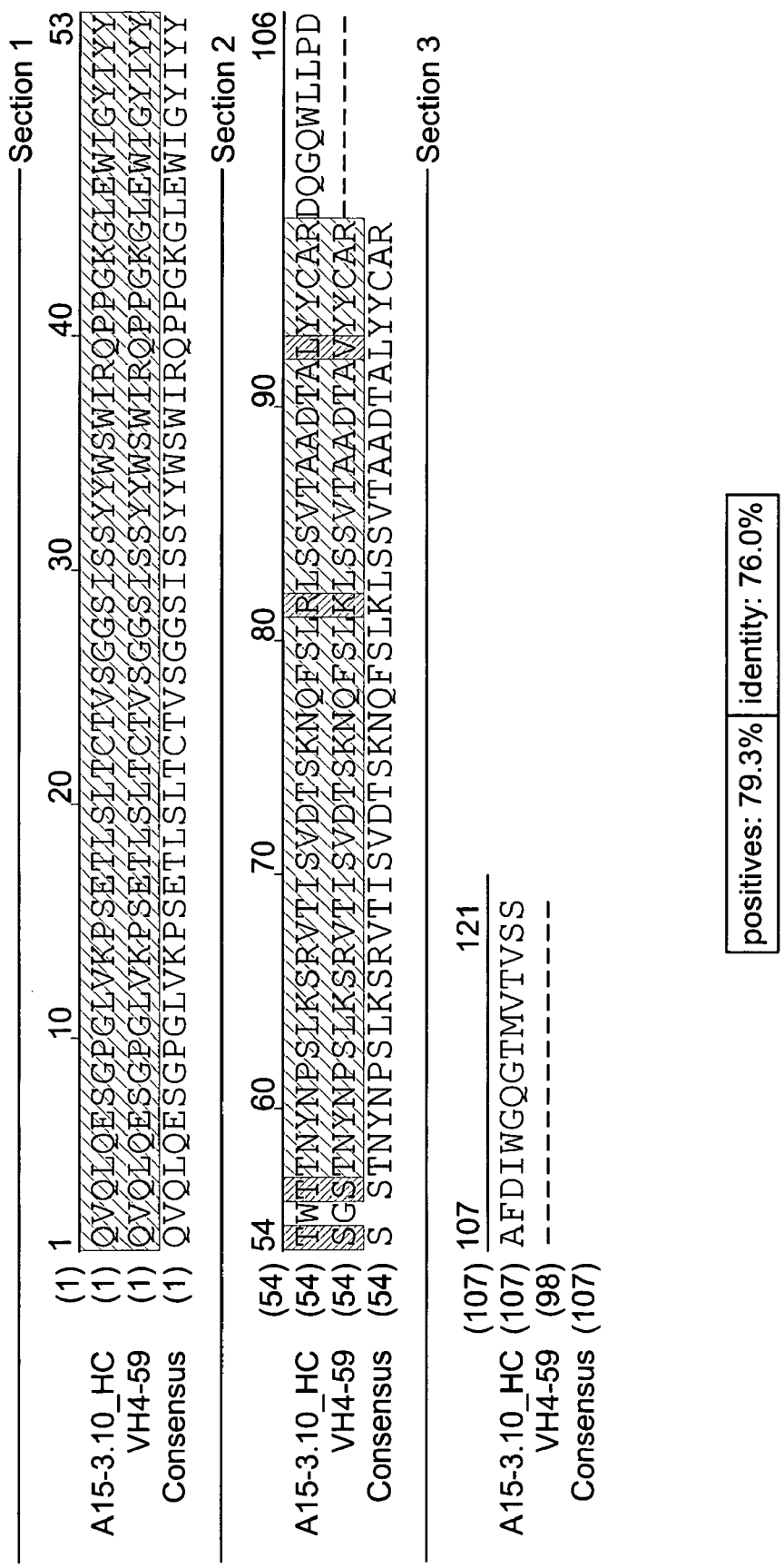
FIG. 16 represents an alignment between the amino acid sequence of the variable region of the heavy chain of anti-MUC18 antibody, c3.10 (SEQ ID NO: 9), and the amino acid sequence encoding the V4–59 region (SEQ ID NO: 41) of the germline $V_H$ gene used. The consensus sequence (SEQ ID NO: 42) is represented below the alignment.
Figure 23:
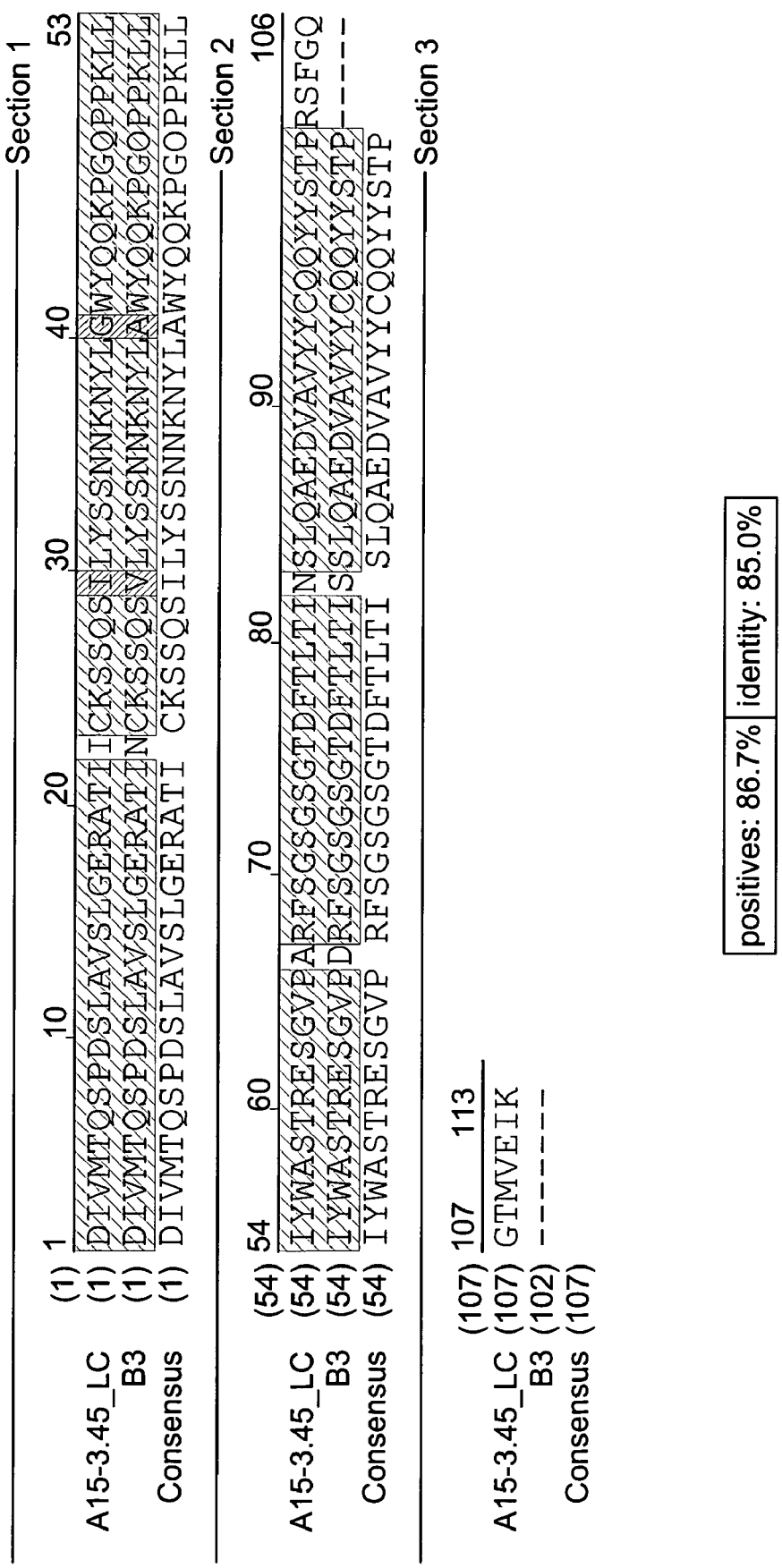
FIG. 23 represents an alignment between the amino acid sequence of the variable region of the light chain of anti-MUC18 antibody, c3.45 (SEQ ID NO: 22), and the amino acid sequence encoding the B3 region (SEQ ID NO: 55) of the germline $V_k$ gene used. The consensus sequence (SEQ ID NO: 56) is represented below the alignment.
Figure 33:
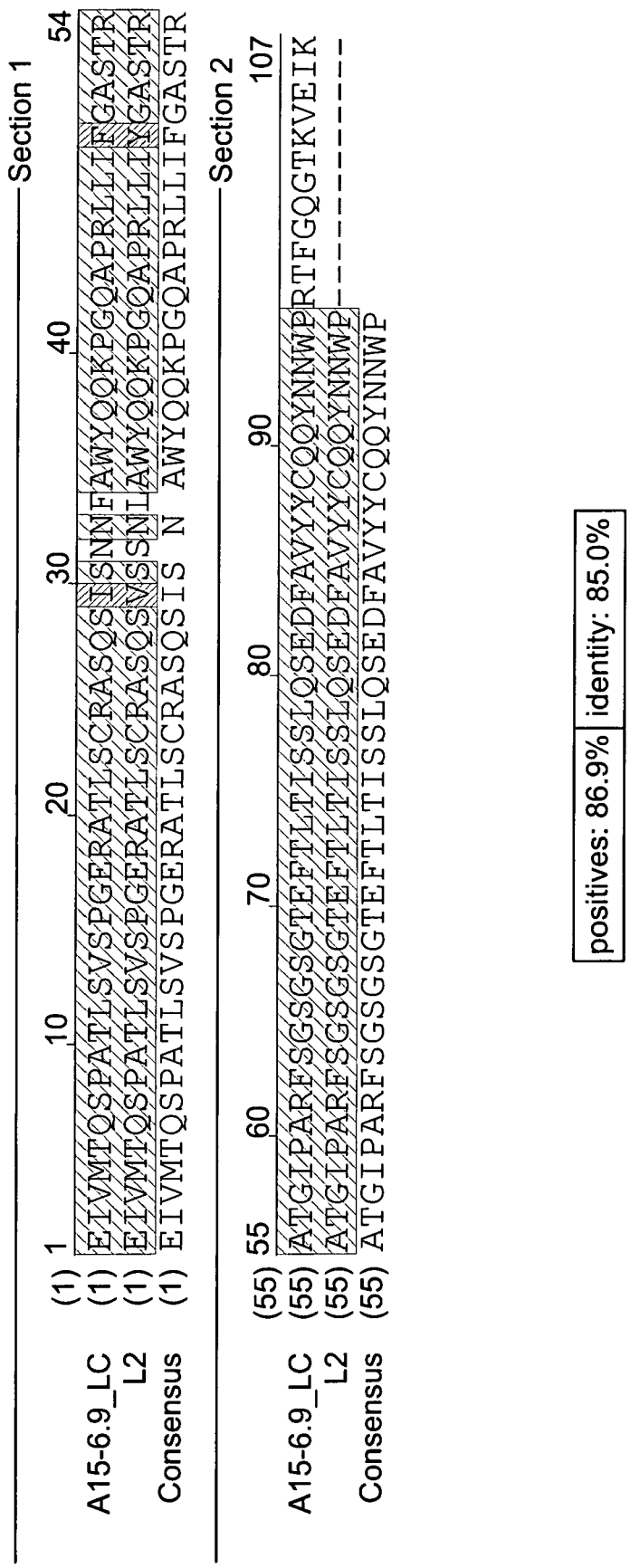
FIG. 33 represents an alignment between the amino acid sequence of the variable region of the light chain of anti-MUC18 antibody, c6.9 (SEQ ID NO: 34), and the amino acid sequence encoding the L2 region (SEQ ID NO: 75) of the germline $V_k$ gene used. The consensus sequence (SEQ ID NO: 76) is represented below the alignment.

Based on the assay results, the following clones were identified as anti-MUC18 antibodies: c3.19.1, c6.11.3, c3.10, c3.22, c3.27, c3.45, c3.65, c6.1, c6.9, c6.2, and c6.12, c6.9 and c6.12 were identical individually identified clones. The antibodies of the present invention were analyzed for sequence similarity to germline $V_H$ and $V_K$ genes. Such analysis is summarized in Table 2 and FIG. 36. The amino acid sequences of the heavy and light chain variable regions of the MUC18 antibodies of the present invention were further aligned with germline $V_H$ and $V_K$ sequences, respectively. These alignments are shown in FIGS. 16–17 (c3.10), FIGS. 18–19 (C3.22), FIGS. 20–21 (C3.27), FIGS. 22–23 (c3.45), FIGS. 24–25 (c3.65), FIGS. 26–27 (c6.1), FIGS. 28–29 (c6.12), FIGS. 30–31 (c6.2), FIGS. 32–33 (c6.9), and FIGS. 34–35 (c6.11), c3.19.1 was selected for further characterization.

B. Characterization of MUC18 Antibodies

1. Binding of Anti-MUC18 Antibodies to MUC18 Antigen (a) Immunoblot Analysis of Binding of Anti-MUC18 Antibody to MUC18

To determine whether anti-MUC18 antibody recognized MUC18 expressed on melanoma cell lines, melanoma cell lines A375SM, SB2, TXM-13, WM-2664 and nude mouse endothelial cells (NME) were seeded ($1\times10^6$) in 100 mm tissue culture plates (Falcon) in 10 mL complete growth medium. After overnight incubation, the plates were washed two times in PBS, and scraped in 400 µl Triton lysis buffer containing a cocktail of protease inhibitors plus DTT. Following centrifugation, the protein concentration was determined using a kit from BioRad. 40 µg of protein was loaded onto a 10% SDS-PAGE and electrophoretically transferred to a 0.45-micron nitrocellulose membrane (Millipore). The membrane was incubated in buffer containing anti-MUC18 antibody overnight, reacted with a conjugated secondary antibody (Anti-human IgG) for one hour and the proteins were subsequently detected by the ECL (Amersham Corp) method according to the manufactures protocol.

Figure 2:
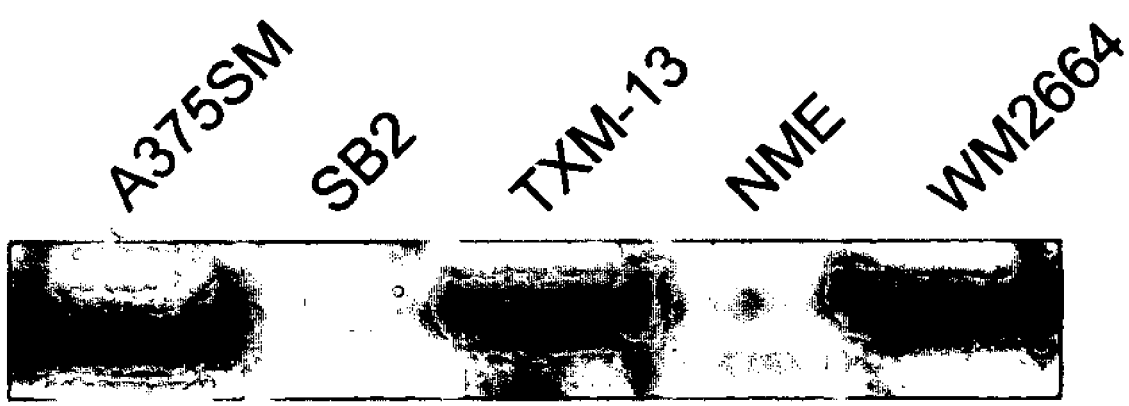
FIG. 2 shows immunoblot analysis with anti-MUC18 antibodies and demonstrates a positive correlation between MUC18 expression with the metastatic capacity of human melanoma cells. The expression of MUC18 in human metastatic melanoma cell lines (A375SM, TXM-13, and WM2664), nonmetastatic cell line SB-2, and normal mouse endothelial (NMEs) cells are shown.

Anti-MUC18 antibodies detected high levels of MUC18 in the metastatic A375SM, TXM-13 and WM-2664 cells and no signal in the nonrmetastatic cell line SB-2 and normal mouse endothelial (NME2) cells were MUC18 (FIG. 2). The reason for the lack of a signal in the NME2 in this experiment was due most likely to the failure of anti-MUC18 antibody to cross-react with mouse MUC18 protein.

Further, these results corroborate the findings of others with respect to a positive correlation between MUC18 expression and the metastatic capacity of melanoma cells (Shih et al., *Clinical Cancer Res.*, 2:569–575 (1996); Johnson et al., *Cancer Metastasis Rev.*, 18:345–357 (1999);

TABLE 2

Comparison of CDR regions in MUC18 antibody clones with CDR regions in germline $V_H$ and $V_K$ genes

| Clone | | Germline genes used | | | No. of Nucleotide/Amino acid changes | | | | | | |
|---|---|---|---|---|---|---|---|---|---|---|---|
| | | | | | FR1 | CDR1 | FR2 | CDR2 | FR3 | CDR3 | FR4 |
| MUC18 | | V | D | J | | | V | | | D & J | |
| A15-3.10 | VH | V4-59 | D21-9 | JH3B | 0/0 | 0/0 | 1/0 | 3/3 | 5/2 | 0/0 | 0/0 |
| | VK | 02 | | JK2 | 0/0 | 1/1 | 1/0 | 1/1 | 1/0 | 1/1 | 0/0 |
| A15-3.22 | VH | V4-31 | — | JH4B | 0/0 | 2/1 | 0/0 | 1/1 | 0/0 | 0/0 | 0/0 |
| | VK | A30 | | JK4 | 0/0 | 0/0 | 0/0 | 0/0 | 0/0 | 0/0 | 0/0 |
| A15-3.27 | VH | V4-59 | D21-9 | JH3B | 0/0 | 0/0 | 1/0 | 4/4 | 6/1 | 0/0 | 0/0 |
| | VK | A30 | | JK1 | 0/0 | 0/0 | 0/0 | 0/0 | 1/0 | 0/0 | 0/0 |
| A15-3.45 | VH | V1-18 | D3-10 | JH6B | 1/0 | 4/2 | 1/1 | 0/0 | 1/0 | 0/0 | 0/0 |
| | VK | B3 | | JK1 | 2/1 | 2/2 | 0/0 | 0/0 | 2/2 | 0/0 | 0/0 |
| A15-3.65 | VH | 4-31 | D6-13 | JH5A | 0/0 | 2/2 | 0/0 | 1/1 | 4/4 | 0/0 | 0/0 |
| | VK | 08 | | JK4 | 0/0 | 1/1 | 0/0 | 0/0 | 2/1 | 1/1 | 0/0 |
| A15-6.1 | VH | V3-30 | D3-3 | JH6B | 1/0 | 1/1 | 0/0 | 0/0 | 0/0 | 0/0 | 0/0 |
| | VK | A20 | | JK3 | 0/0 | 1/1 | 1/1 | 1/1 | 0/0 | 3/3 | 2/1 |
| A15-6.2 | VH | V4-59 | D6-19 | JH3B | 1/0 | 2/1 | 1/0 | 4/3 | 4/2 | 0/0 | 0/0 |
| | VK | A19 | | JK4 | 2/1 | 2/2 | 0/0 | 0/0 | 2/2 | 2/1 | 0/0 |
| A15-6.9 | VH | V4-31 | D5-24 | JH1 | 4/3 | 3/2 | 2/1 | 1/1 | 2/1 | 0/0 | 0/0 |
| | VK | L2 | | JK1 | 0/0 | 3/3 | 1/1 | 0/0 | 2/0 | 0/0 | 0/0 |
| A15-6.11 | VH | V4-31 | D5-24 | JH1 | 0/0 | 3/2 | 0/0 | 0/0 | 0/0 | 0/0 | 0/0 |
| | VK | L2 | | JK1 | 0/0 | 2/1 | 0/0 | 0/0 | 0/0 | 0/0 | 0/0 |
| A15-6.12 | VH | V4-31 | D5-24 | JH1 | 4/3 | 3/2 | 2/1 | 1/1 | 2/1 | 0/0 | 0/0 |
| | VK | L2 | | JK1 | 0/0 | 3/3 | 1/1 | 0/0 | 2/0 | 0/0 | 0/0 |

Xie et al., *Oncogene*, 15(17):2069–75 (1997); Xie et al., *Cancer Res.*, 57(11):2295–303 (1997); Schlagbauer-Wadl et al., *Int J Cancer*, 81(6):951–5 (1999)).

(b) Flow Cytometric Analysis of Binding of Anti-MUC18 Antibody to MUC18 triplicate for 2.5 minutes at 100 μL/min., and the dissociation phase was followed for 10 mins. The data were processed by "Scrubber", version 1.10, and the processed sensorgrams were non-linearly fit by "Clamp", version 3.40, employing a simple bimolecular 1:1 kinetic model (Table 3).

TABLE 3

Binding Kinetics and Affinity of anti-MUC18 antibody (c3.19.1) for MUC18 Antigen

| Date of Measurement | Chip Designation* | c3.19.1Lot# | $k_a$ $(M^{-1}s^{-1})$ | $k_d$ $(s^{-1})$ | $K_d$ (nM) |
|---|---|---|---|---|---|
| May 2001 | I | 385020A | $4.531 \times 10^5$ | $3.021 \times 10^{-4}$ | 0.67 |
| October 2001 | II | 360–67 | $7.090 \times 10^5$ | $4.019 \times 10^{-4}$ | 0.57 |
| October 2001 | II | 360–67 | $5.746 \times 10^5$ | $3.961 \times 10^{-4}$ | 0.69 |
| November 2001 | III | 360–67 | $7.494 \times 10^5$ | $3.466 \times 10^{-4}$ | 0.46 |
| November 2001 | III | 360–67 | $6.251 \times 10^5$ | $3.852 \times 10^{-4}$ | 0.62 |
| November 2001 | III | RD#1 | $6.146 \times 10^5$ | $4.021 \times 10^{-4}$ | 0.65 |
| November 2001 | III | RD#2 | $6.608 \times 10^5$ | $3.894 \times 10^{-4}$ | 0.59 |

*Legend for chip designation: I, B1 Chip made May 2001; II, B1 Chip made October 2001; III, B1 chip made November 2001. All chips had approximately 1500–3500 RU of protein A immobilized/flowcell.

| | Average | Standard Deviation | 95% Confidence Interval |
|---|---|---|---|
| $k_a$ $(M^{-1}s^{-1})$ | $6.27 \times 10^5$ | $\pm 9.66 \times 10^4$ | $\pm 8.94 \times 10^4$ (14%) |
| $k_d$ $(s^{-1})$ | $3.75 \times 10^{-4}$ | $\pm 3.73 \times 10^{-5}$ | $\pm 3.45 \times 10^{-5}$ (9.2%) |
| $K_d$ (nM) | 0.61 | $\pm 0.078$ | $\pm 0.072$ (12%) |

To determine whether anti-MUC18 antibody recognized the native form of the MUC18 protein on the surface of cells, flow cytometry analysis was performed.

A375-SM and WM-2664 cells (4×10⁵) were detached with PBS-EDTA and incubated in FACS buffer (PBS, 2% FBS and 0.02% sodium azide) with either an isotype-matched control human IgG2 antibody or anti-MUC18 antibody for 20 minutes at 4° C. After washing with FACS buffer, all samples were incubated with phycoerythrin-conjugated F(ab')$_2$ fragments of Goat Anti-Human IgG (H+L) (Jackson) for 20 minutes at 4° C. in the dark. After several washings, the cells were resuspended in FACS buffer and analyzed by cytofluorometry.

As shown in FIG. 3, neither the A375-SM nor the WM-2664 cells demonstrated a fluorescent shift when incubated in the presence of the control IgG2 Ab (bold line). However, when incubated in the presence of anti-MUC18 (dotted line), a strong shift in fluorescence intensity indicative of cell surface expression of the antigen was observed. These results show that anti-MUC18 antibody can recognize the native MUC18 antigen expressed on the surface of human melanoma cells.

(c). Binding Kinetics and Affinity of MUC18 to anti-MUC18 Antibody

A Biacore 3000 instrument was used for all kinetic measurements with HBS-P (Hepes-buffered saline, 0.005% polysorbate 20) buffer. The measurements were made utilizing three B1 sensor chips (carboxymethyldextran matrix with a low amount of carboxylation). The experiments were performed by covalently immobilizing protein A by standard amine coupling at a level of 1500–3000 RU (resonance units) on the surface of the four flow cells of a B1 chip. MAb 3.19.1 was captured by flowing a 1 μg/ml solution of 3.19.1 at a flow rate of 60 μL/min. for 20–30 sec. across the protein A surface, giving a captured level of 110–250 RU. The control protein A surface did not have any MAb captured on it. Various concentrations of MUC18-V5-His antigen, ranging from 0.5 nM-100 nM, were flowed across the surface in 2. Effect of Anti-MUC18 Antibody on Growth of a Melanoma Tumor Xenograft To evaluate the effect of anti-MUC18 antibody (c3.19.1) treatment on the growth of a subcutaneous tumor, exponentially growing WM-2664 cells were harvested and resuspended in 0.2 mL of Hank's Balanced Salt solution (HBSS). Tumors were produced following the injection of 2.5×10⁵ cells into the flanks of male BALB/c nude mice. Beginning on Day 3 after implantation, animals were treated with 0.1 mg (n=5) or 1.0 mg (n=5) of c3.19.1 or 0.1 mg 9n=5) control human IgG2 (Jackson Laboratories) once a week. Tumor growth was monitored weekly and the results presented as mean±SD (FIG. 4).

Figure 4:
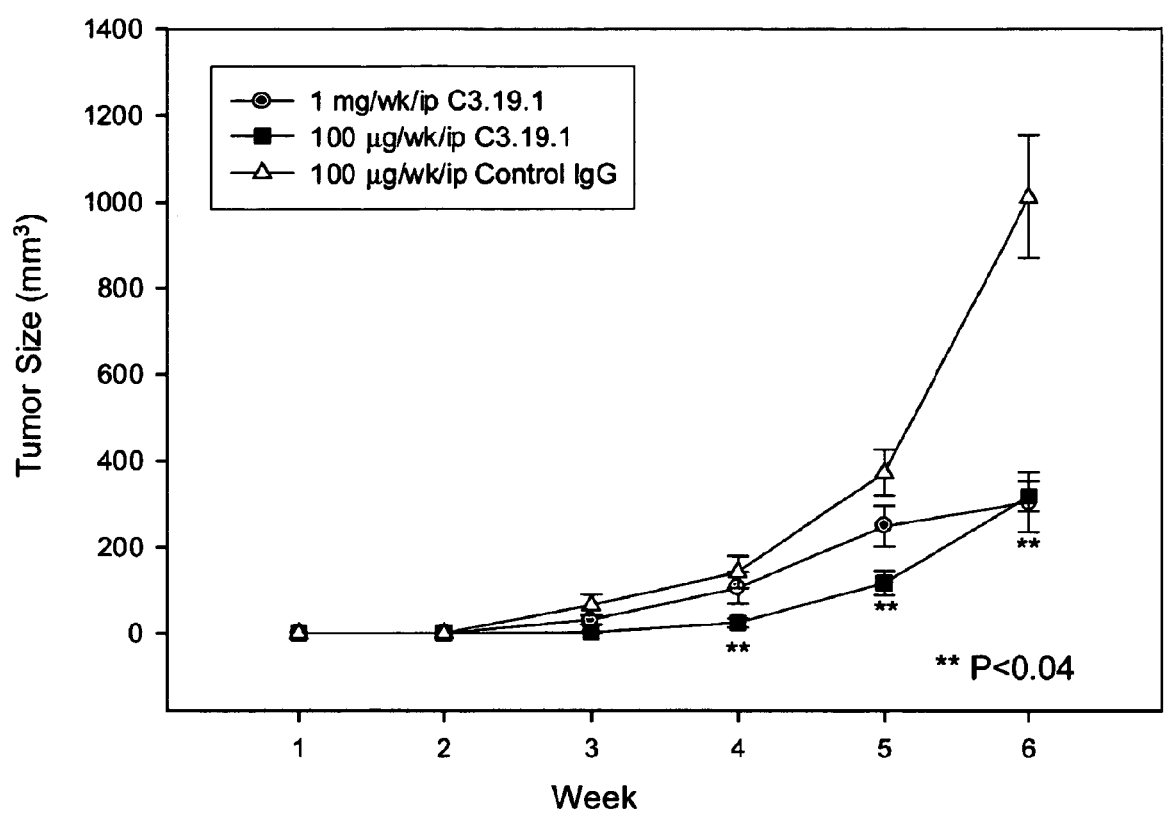
FIG. 4 shows that anti-MUC18 antibody, c3.19.1, inhibits the subcutaneous growth of WM-2264 tumor cells in vivo.

The results presented in FIG. 4 demonstrates that anti-MUC18 antibodies can inhibit the subcutaneous growth of WM-2664 cells in vivo. Concentrations as low as 0.1 mg of anti-MUC18 antibody per week were effective in this tumor model.

3. Effect of Anti-MUC18 Antibody on Metastasis of Melanoma Cells in Vivo

Because MUC18 expression is most closely associated with the metastatic phenotype in melanoma patients, the ability of anti-MUC18 antibody (c3.19.1) to inhibit the formation of lung metastases when injected intravenously into the tail veins of nude mice was examined. A375-SM and WM-2664 melanoma cells were harvested in their exponential growth pnase, resuspended in Hanks' balanced salt solution (HBSS) and 2.5×10⁵ viable tumor cells were injected into the lateral tail vein. Mice were treated with the indicated concentration of anti-MUC18 antibody (c3.19.1) beginning on Day 3 and once weekly thereafter. The mice were sacrificed 6–8 weeks later. After fixing and staining with Bouin's solution, lung nodules were counted with the aid of a dissecting microscope.

TABLE 4

Anti-MUC18 Antibody (c3.19.1) Inhibits Melanoma
Metastasis Formation in the Lung

| Cell Line | Treatment | Median No. Metastases | Range of Metastases | Incidence of Metastases |
|---|---|---|---|---|
| A375SM | IgG Control | 18 | 5–34 | 5/5 |
| A375SM | c3.19.1 (100 μg/mL) | 1 | 0–6 | 3/5 |
| A375SM | c3.19.1 (1 mg/mL) | 0 | 0–1 | 2/5 |
| WM-2664 | IgG | 11 | 4–21 | 5/5 |
| WM-2664 | c3.19.1 (100 μg/mL) | 1 | 0–4 | 3/5 |
| WM-2664 | c3.19.1 (1 mg/mL) | 2 | 0–8 | 4/5 |

As shown in Table 4, anti-MUC18 antibody (c3.19.1) treatment resulted in a significant decrease in the number and incidence of lung metastases in animals injected with A375-SM tumor cells. Inhibition of lung metastases was observed at both the high and low dose treatment groups. A trend towards a decrease in the number of metastases was also observed in the WM-2664 cells.

To further corroborate these data a more extensive experiment was performed. Exponentially growing A375-SM cells were harvested on Day 0, resuspended in Hanks' balanced salt solution (HBSS) and $4 \times 10^5$ viable tumor cells were injected into the lateral tail veins of female nude mice from Harlan Laboratories. The animals were treated one day prior to tumor cell injection and once a week thereafter with the indicated dose of anti-MUC18 antibody. All animals were sacrificed after six weeks at which time the lungs were removed and the tumor nodules counted with the aid of a dissecting microscope. The results of this experiment are presented in Table 5 and demonstrate that anti-MUC18 antibody inhibits lung tumor formation in a dose-dependent manner. The total number of lung metastases was decreased in all treated animals. In mice receiving the 1.0 mg per mouse dose of anti-MUC18 (c3.19.1), the tumor burden was very low and no animals had more than 50 nodules in their lungs.

TABLE 5

A375-SM Melanoma Metastasis Formation in Mouse Lungs

| Treatment | Incidence of Tumors | Animals with ≦10 Tumors | Animals with 11–50 Tumors | Animals with >50 Tumors | Median No. Tumors/Animal |
|---|---|---|---|---|---|
| Control Antibody | 13/14 | 7/14 | 3/14 | 4/14 | 10 |
| c3.19.1 0.1 mg/dose | 10/14 | 6/14 | 5/14 | 3/14 | 12 |
| c3.19.1 1.0 mg/dose | 14/14 | 12/14 | 2/14 | 0/14 | 5 |

One additional study was performed in vivo to evaluate the ability of anti-MUC 18 antibody (c3.19.1) to increase the survival of mice bearing metastatic melanoma tumors. The WM-2664 human melanoma tumor cells in their exponential growth phase were harvested and resuspended in PBS. Viable tumor cells ($10^6$ in 0.2 mL PBS) were injected into the lateral tail vein of male BALB/c nude mice on Day 0. On the same day, the animals were administered PBS (n=21), c3.19.1 (n=12) or isotype-matched control IgG2 antibody (n=12) intraperitoneally at 1 mg or 0.2 mg per mouse, and once weekly thereafter. The mice were monitored everyday for survival. Autopsies were performed on dead mice from the different groups to confirm the presence of tumor metastases. The data were expressed as percent survival calculated as follows: 100–[100×(Number of dead mice/Total number of mice)].

Figure 5:
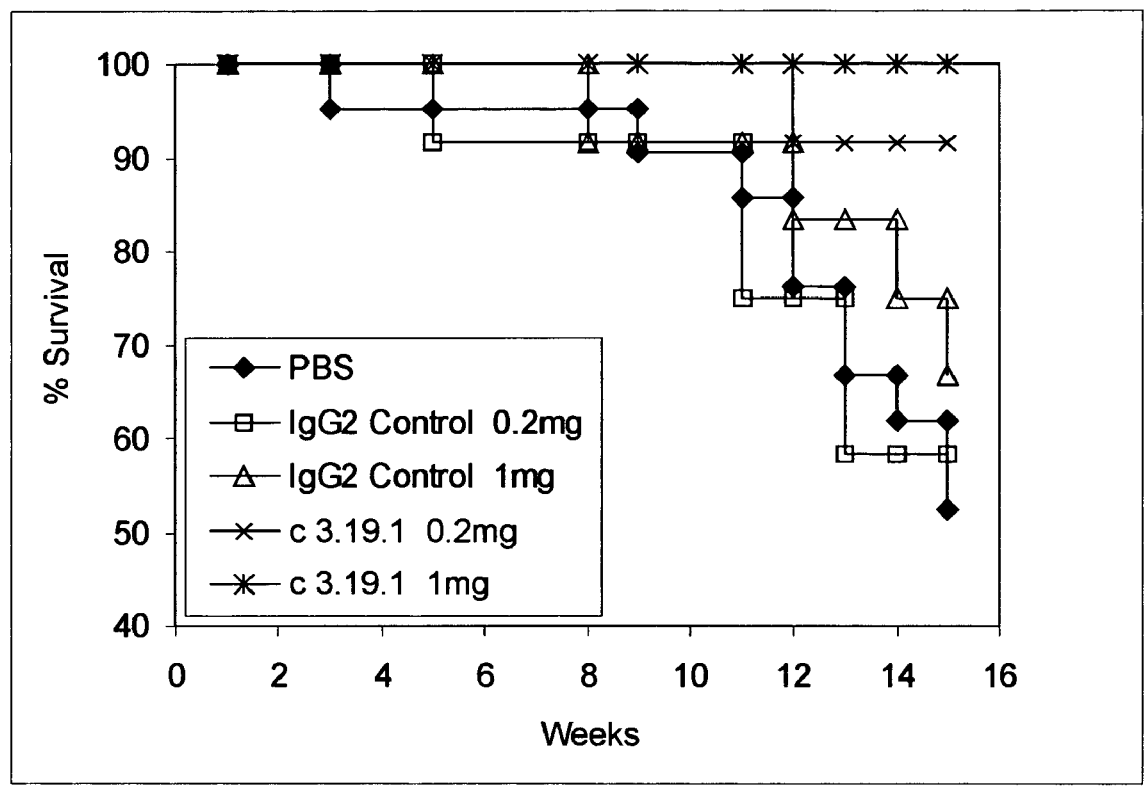
FIG. 5 demonstrates that treatment with anti-MUC18 antibody, c3.19.1, prolongs the survival of WM-2664 mice bearing metastatic melanoma tumors.

FIG. 5 demonstrated that treatment with anti-MUC18 antibody (c3.19.1) can prolong the survival of mice bearing metastatic melanoma tumors. A dose dependent increase in survival was observed and to date no animals in the group receiving the high dose of anti-MUC18 antibody have died due to tumor burden.

4. Effect of Anti-MUC18 Antibody on Melanoma Cell Invasion in Vitro

Melanoma metastasis is closely associated with MUC18 expression. One of the phenotypic changes often associated with metastasis is the ability of cells to migrate and invade through the extracellular matrix. Accordingly, anti-MUC18 antibodies were tested for their ability to influence the ability of MUC18 expressing cells to invade and migrate through Matrigel coated membranes. $5 \times 10^3$ cells were seeded into six well plates and allowed to attach for 24 hours. At this time the medium was removed and replaced with fresh growth medium containing either a nonspecific IgG, anti-MUC18 antibody or no addition. After five days the cells were detached from the plates using Trypsin-EDTA and counted. $5 \times 10^4$ cells were placed in the upper chamber of the Matrigel coated membrane in serum-free medium containing either 100 μg/mL anti-MUC18 antibody (c3.19.1), non-specific IgG or serum-free media alone. Following incubation at 37° C. for 22 hours, the cells remaining in the upper chamber were removed by scraping and the bottom filter stained with Diff-Quik according to manufacturers directions. The matrices were mounted on slides and the cells that had migrated across the membrane were counted.

The data presented in Table 6 demonstrates that exposure of metastatic melanoma cells to anti-MUC18 antibody (c3.19.1) inhibited their ability to digest the extracellular matrix and migrate toward the chemoattractant placed on the opposite side.

TABLE 6

C3.19.1 Inhibits Invasion of Melanoma Cells
through Matrigel- Coated Membrane

| Cell Line | Treatment | Average No. Migrating Cells ± SD |
|---|---|---|
| A375SM | None | 2574 ± 94 ($P < 0.01$) |
| A375SM | Control human IgG | 2068 ± 129 ($P < 0.01$) |
| A375SM | C3.19.1 | 57 ± 8 |
| WM-2664 | None | 1857 ± 57 ($P < 0.01$) |
| WM-2664 | Control human IgG | 1866 ± 131 ($P < 0.01$) |
| WM-2664 | C3.19.1 | 56 ± 7 |

The role of MUC18 in melanoma tumor progression and the mechanism of anti-MUC18 antibody (c3.19.1) action on this target is not completely understood. Although anti-MUC18 antibody does not inhibit the growth of melanoma tumor cells in cell culture, it does inhibit the growth of subcutaneous and metastatic tumor cells in vivo. The cumulative evidence indicates that MUC18 plays a role in one or more steps in the metastatic process possibly by affecting MMP-2 activation or cell migration. When considered together these data provide evidence that anti-MUC18 antibody is a promising therapeutic antibody for inhibiting the growth and metastasis of human melanoma cells in patients with this disease.

EXAMPLE 3

Antibody Conjugates

Antibodies specific to antigens such as anti-MUC18 are useful in targeting of tumor cells expressing such antigens for elimination.

A. Linkage of Anti-MUC18 Antibody to Ricin

Ricin, a cellular toxin, is finding unique applications, especially in the fight against tumors and cancer. Implications are being discovered as to the use of ricin in the treatment of tumors. Ricin has been suggested to have a greater affinity for cancerous cells than normal cells (Montfort et al. 1987) and has been often termed as a "magic bullet" for targeting malignant tumors. Toxins such as ricin remain active even if the B chain which is responsible for because of toxin nonspecific lectin activity leads to toxic side effects is removed. Accordingly, if the solitary A chain is coupled to a tumor-specific antibody, the toxin has a specific affinity for cancerous cells over normal cells (Taylorson 1996). For example, ricin immunotoxin has been developed to target the CD5 T-cell antigen often found in T-cell and B-cell malignancies (Kreitman et al. 1998).

A novel method of coupling whole intact ricin to monoclonal antibody is described in Pietersz et al. (*Cancer Res* 48(16):4469–76 (1998)) and includes blocking of nonspecific binding of the ricin B-chain. Coupling of ricin to the anti-MUC18 antibodies of the present invention may be done by using the bifunctional reagents S-acetylmercaptosuccinic anhydride for antibody and succinimidyl 3-(2-pyridyldithio)propionate for ricin. The coupling should result in the loss of B-chain binding activity, while impairing neither the toxic potential of the A-chain nor the activity of the antibody. Whole ricin-antibody conjugates produced in this way should not bind nonspecifically to target cells, the most important implication being that such immunotoxins should be more potent that ricin A-chain conjugates and capable of being used in vivo.

B. Linkage to Radioisotope

The linking of such anti-MUC18 antibodies to radioisotopes provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. With this "magic bullet," the patient can be treated with much smaller quantities of radioisotopes than other forms of treatment available today. Preferred radioisotopes include yttrium$^{90}$ (90Y), indium$^{111}$ (111In), $^{131}$I, $^{99}$mTc, radiosilver-111, radiosilver-199, and Bismuth$^{213}$.

Linkage of radioisotopes to antibodies may be performed with conventional bifunction chelates. Since silver is monovalent, for radiosilver-111 and radiosilver-199 linkage, sulfur-based linkers may be used (Hazra et al., *Cell Biophys,* 24–25:1–7 (1994)). Linkage of silver radioisotopes may involved reducing the immunoglobulin with ascorbic acid. In another aspect, tiuxetan is an MX-DTPA linker chelator attached to ibritumomab to form ibritumomab tiuxetan (Zevalin) (Witzig, T. E, *Cancer Chemother Pharmacol,* 48 Suppl 1:S91–5 (2001). Ibritumomab tiuxetan can react with radioisotypes such as indium$^{111}$ (111In) or 90Y to form 111In-ibritumomab tiuxetan and 90Y-ibritumomab tiuxetan, respectively.

C. Linkage of Anti-MUC18 Antibody to Toxic Chemotherapeutic Agents

Most commonly antibodies to treat cancer are being conjugated with toxic chemotherapeutic drugs such as maytansine, geldanamycin or calichaemycin. Different linkers that release the drugs under acidic or reducing conditions or upon exposure to specific proteases are employed with this technology.

EXAMPLE 4

Uses of Anti-MUC18 Antibodies and Antibody Conjugate

A. Treatment of Humans with Anti-MUC18 Antibodies

To determine the in vivo effects of anti-MUC18 antibody treatment in human patients with tumors, such human patients are injected over a certain amount of time with an effective amount of anti-MUC18 antibody. At periodic times during the treatment, the human patients are monitored to determine whether their tumors progress, in particular, whether the tumors grow and metastasize.

A tumor patient treated with anti-MUC18 antibodies have a lower level of tumor growth and metastasis compared to the level of tumor growth and metastasis of tumors in tumor patients treated with control antibodies. Control antibodies that may be used include antibodies of the same isotype as the anti-MUC18 antibodies tested and further, may not have the ability to bind to MUC18 tumor antigen.

B. Treatment with Anti-MUC18 Antibody Conjugates

To determine the in vivo effects of anti-MUC18 antibody conjugates, human patients or animals exhibiting tumors are injected over a certain amount of time with an effective amount of anti-MUC18 antibody conjugate. In one embodiment, the anti-MUC18 antibody conjugate administered is maytansine-anti-MUC18 antibody conjugate or radioisotope-anti-MUC18 antibody conjugate. At periodic times during the treatment, the human patients or animals are monitored to determine whether their tumors progress, in particular, whether the tumors grow and metastasize.

A human patient or animal exhibiting tumors and undergoing treatment with either maytansine-anti-MUC18 antibody or radioisotope-anti-MUC18 antibody conjugates have a lower level of tumor growth and metastasis when compared to a control patient or animal exhibiting tumors and undergoing treatment with control antibody conjugates, such as control maytansine-antibody or control radioisotope-antibody. Control maytansine-antibodies that may be used include conjugates comprising maytansine linked to antibodies of the same isotype of the anti-MUC18 antibodies, but more specifically, not having the ability to bind to MUC18 tumor antigen. Control radioisotope-antibodies that may be used include conjugates comprising radioisotope linked to antibodies of the same isotype of the anti-MUC18 antibodies, but more specifically, not having the ability to bind to MUC18 tumor antigen.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents.

SEQUENCE LISTING

<160> NUMBER OF SEQ ID NOS: 40

<210> SEQ ID NO 1
<211> LENGTH: 121
<212> TYPE: PRT
<213> ORGANISM: Homo Sapiens

<400> SEQUENCE: 1

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Thr Trp Thr Ser Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Gln Gly Gln Trp Leu Leu Pro Asp Ala Phe Asp Ile Trp Gly
            100                 105                 110

Gln Gly Thr Met Val Thr Val Ser Ser
        115                 120

<210> SEQ ID NO 2
<211> LENGTH: 112
<212> TYPE: PRT
<213> ORGANISM: Homo Sapiens

<400> SEQUENCE: 2

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Gln Ser Pro Ile Thr Phe Gly Gln Gly Thr Arg Leu Glu Ile Lys
            100                 105                 110

<210> SEQ ID NO 3
<211> LENGTH: 364
<212> TYPE: DNA
<213> ORGANISM: Homo Sapiens

<400> SEQUENCE: 3
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattggctat atctattaca cttggacctc caactacaac     180

-continued

```
ccctccctca agagtcgcgt caccatatca gtggacacgt ccaaaaacca gttctccctg      240
aggctgagtt ctgtgaccgc tgcggacacg gccgtttatt actgtgcgag agatcagggg      300
cagtggttac tacccgatgc ttttgatatc tggggccaag ggacaatggt caccgtctct      360
tcag                                                                  364
```

<210> SEQ ID NO 4
<211> LENGTH: 337
<212> TYPE: DNA
<213> ORGANISM: Homo Sapiens

<400> SEQUENCE: 4

```
gatattgtga tgactcagtc tccactctcc ctgcccgtca cccctggaga gccggcctcc       60
atctcctgca ggtctagtca gagcctcctg cgtagtaatg gatacaacta tttggattgg      120
tacctgcaga agccaggaca gtctccacat ctcctgatct atttgggttc taatcgggcc      180
tccggggtcc ctgacaggtt cagtggcagt ggatcaggca cagattttac actgaaaatc      240
agcagagtgg aggctgagga tgttggggtt tattactgca tgcaagctca acaaagtccg      300
atcaccttcg gccaagggac acgactggag attaaac                               337
```

<210> SEQ ID NO 5
<211> LENGTH: 117
<212> TYPE: PRT
<213> ORGANISM: Homo Sapiens

<400> SEQUENCE: 5

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Thr Tyr His Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Gly Asp Gly Tyr Lys Tyr Trp Gly Gln Gly Thr Leu
            100                 105                 110

Val Thr Val Ser Ser
        115
```

<210> SEQ ID NO 6
<211> LENGTH: 107
<212> TYPE: PRT
<213> ORGANISM: Homo Sapiens

<400> SEQUENCE: 6

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Asn Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60
```

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105

<210> SEQ ID NO 7
<211> LENGTH: 352
<212> TYPE: DNA
<213> ORGANISM: Homo Sapiens

<400> SEQUENCE: 7
caggtgcagc tgcaggagtc gggcccagga ctggtgaagc cttcacagac cctgtccctc      60
acctgcactg tctctggtgg ctccatcagc agtggtactt accactggag ctggatccgc     120
cagcacccag gaagggcct ggagtggatt gggtacatct attacagtgg gagcacctac      180
tacaacccgt ccctcaagag tcgagttacc atatcagtag acacgtctaa gaaccagttc     240
tccctgaagc tgagctctgt gactgccgcg gacacggccg tgtattactg tgcgagaggg     300
ggagatggct acaagtactg gggccaggga accctggtca ccgtctcctc ag             352

<210> SEQ ID NO 8
<211> LENGTH: 322
<212> TYPE: DNA
<213> ORGANISM: Homo Sapiens

<400> SEQUENCE: 8
gaaatagtga tgacgcagtc tccagccacc ctgtctgtgt ctccagggga aagagccacc      60
ctctcctgca gggccagtca gagtgttagc aacaacttag cctggtatca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctcggac gttcggccaa     300
gggaccaagg tggaaatcaa ac                                              322

<210> SEQ ID NO 9
<211> LENGTH: 121
<212> TYPE: PRT
<213> ORGANISM: Homo Sapiens

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Thr Trp Thr Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Leu Tyr Tyr Cys Ala
                85                  90                  95

Arg Asp Gln Gly Gln Trp Leu Leu Pro Asp Ala Phe Asp Ile Trp Gly
            100                 105                 110

Gln Gly Thr Met Val Thr Val Ser Ser
        115                 120

<210> SEQ ID NO 10
<211> LENGTH: 109
<212> TYPE: PRT
<213> ORGANISM: Homo Sapiens

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Arg Gln Ser Tyr Ser Thr Pro Pro
                85                  90                  95

Glu Cys Ser Phe Gly Gln Gly Thr Lys Leu Glu Ile Lys
            100                 105

<210> SEQ ID NO 11
<211> LENGTH: 364
<212> TYPE: DNA
<213> ORGANISM: Homo Sapiens

<400> SEQUENCE: 11
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattggctat atctattaca cttggaccac caactacaac     180
ccctccctca gagtcgcgt caccatatca gtggacacgt ccaagaacca gttctccctg      240
aggctgagct ctgtgaccgc tgcggacacg gccctttatt actgtgcgag agatcagggg     300
cagtggttac tacccgatgc ttttgatatc tggggccaag ggacaatggt caccgtctct     360
tcag                                                                  364

<210> SEQ ID NO 12
<211> LENGTH: 328
<212> TYPE: DNA
<213> ORGANISM: Homo Sapiens

<400> SEQUENCE: 12
gacatccaga tgacccagtc tccatcctcc ctgtctgcat ctgtaggaga cagagtcacc      60
atcacttgcc gggcaagtca gagcattagc aactatttaa attggtatca gcagaaacca     120
ggaaaagccc ctaagctcct gatctatggt gcatccagtt tgcaaagtgg ggtcccatca     180
aggttcagtg gcagtggatc tgggacagat ttcactctca ccatcagcag tctgcaacct     240
gaagattttg caacctacta ctgtcgacag agttacagta cccctccgga gtgcagtttt     300
ggccagggga ccaagctgga gatcaaac                                        328

<210> SEQ ID NO 13
<211> LENGTH: 117
<212> TYPE: PRT
<213> ORGANISM: Homo Sapiens

<400> SEQUENCE: 13

Gln Val Gln Leu Gln Glu Ser Gly Pro Gly Leu Val Lys Pro Ser Gln
 1               5                  10                  15

Thr Leu Ser Leu Thr Cys Thr Val Ser Gly Ser Ile Ser Ser Gly
            20                  25                  30

Gly Tyr Tyr Trp Thr Trp Ile Arg Gln His Pro Gly Lys Gly Leu Glu
        35                  40                  45

Trp Ile Gly Phe Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Asp Gly Phe Asp Tyr Trp Gly Gln Gly Thr Leu
            100                 105                 110

Val Thr Val Ser Ser
            115

<210> SEQ ID NO 14
<211> LENGTH: 107
<212> TYPE: PRT
<213> ORGANISM: Homo Sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 15
<211> LENGTH: 352
<212> TYPE: DNA
<213> ORGANISM: Homo Sapiens

<400> SEQUENCE: 15
caggtgcagc tgcaggagtc gggcccagga ctggtgaagc cttcacagac cctgtccctc      60
acctgcactg tctctggtgg ctccatcagc agtggtggtt actactggac ttggatccgc     120
cagcacccag ggaagggcct ggagtggatt gggttcatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagag     300
ggagatggct ttgactactg gggccaggga accctggtca ccgtctcctc ag             352

<210> SEQ ID NO 16
<211> LENGTH: 322

<212> TYPE: DNA
<213> ORGANISM: Homo Sapiens

<400> SEQUENCE: 16

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagg tggagatcaa ac                                              322
```

<210> SEQ ID NO 17
<211> LENGTH: 121
<212> TYPE: PRT
<213> ORGANISM: Homo Sapiens

<400> SEQUENCE: 17

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Thr Trp Thr Ser Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Gln Gly Gln Trp Leu Leu Pro Asp Ala Phe Asp Ile Trp Gly
            100                 105                 110

Gln Gly Thr Met Val Thr Val Ser Ser
        115                 120
```

<210> SEQ ID NO 18
<211> LENGTH: 107
<212> TYPE: PRT
<213> ORGANISM: Homo Sapiens

<400> SEQUENCE: 18

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

-continued

<210> SEQ ID NO 19
<211> LENGTH: 364
<212> TYPE: DNA
<213> ORGANISM: Homo Sapiens

<400> SEQUENCE: 19
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattggctat atctattaca cttggaccct caactacaac     180
ccctccctca gagtcgcgt caccatatca gtggacacgt ccaagaacca gttctccctg     240
aggctgagtt ctgtgaccgc tgcggacacg gccgtttact actgtgcgag agatcagggg     300
cagtggttac tacccgatgc ttttgatatc tggggccaag gacaatggt caccgtctct     360 tcag                                                                  364

<210> SEQ ID NO 20
<211> LENGTH: 322
<212> TYPE: DNA
<213> ORGANISM: Homo Sapiens

<400> SEQUENCE: 20
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagag ttcactctca caatcagcag cctgcagcct     240
gaagattttg caacttatta ctgtctacag cataatagtt acccgtggac gttcggccaa     300
gggaccaagg tggaaatcaa ac                                              322

<210> SEQ ID NO 21
<211> LENGTH: 123
<212> TYPE: PRT
<213> ORGANISM: Homo Sapiens

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Phe Ser Tyr
            20                  25                  30

Gly Phe Ser Trp Val Arg Gln Ala Pro Gly Gln Gly Leu Glu Trp Leu
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Thr Lys Val Arg Gly Val His Tyr Tyr Gly Met Asp Val
            100                 105                 110

Trp Gly Gln Gly Thr Thr Val Thr Val Ser Ser
        115                 120

<210> SEQ ID NO 22
<211> LENGTH: 113
<212> TYPE: PRT
<213> ORGANISM: Homo Sapiens

```
<400> SEQUENCE: 22

Asp Ile Val Met Thr Gln Ser Pro Asp Ser Leu Ala Val Ser Leu Gly
  1               5                  10                  15

Glu Arg Ala Thr Ile Ile Cys Lys Ser Ser Gln Ser Ile Leu Tyr Ser
             20                  25                  30

Ser Asn Lys Asn Tyr Leu Gly Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Ala Arg Phe Ser Gly Ser Gly Ser Gly Thr Asp Phe Thr Leu Thr
 65                  70                  75                  80

Ile Asn Ser Leu Gln Ala Glu Asp Val Ala Val Tyr Tyr Cys Gln Gln
                 85                  90                  95

Tyr Tyr Ser Thr Pro Arg Ser Phe Gly Gln Gly Thr Met Val Glu Ile
            100                 105                 110

Lys

<210> SEQ ID NO 23
<211> LENGTH: 370
<212> TYPE: DNA
<213> ORGANISM: Homo Sapiens

<400> SEQUENCE: 23
caggttcagc tggtgcagtc gggagctgag gtgaagaagc ctggggcctc agtgaaggtc      60
tcctgcaagg cttctggtta cacctttttt agctatggtt tcagctgggt gcgacaggcc    120
cctggacaag gcttgagtg gctgggatgg atcagcgctt acaatggtaa cacaaactat     180
gcacagaagc tccagggcag agtcaccatg accacagaca cttccacgag cacagcctac    240
atggagctga ggagcctgag atctgacgac acggccgtgt attactgtgc gagagaaact    300
aaggttcggg gagtccacta ctacggtatg gacgtctggg gccaagggac cacggtcacc    360
gtctcctcag                                                           370

<210> SEQ ID NO 24
<211> LENGTH: 340
<212> TYPE: DNA
<213> ORGANISM: Homo Sapiens

<400> SEQUENCE: 24
gacatcgtga tgacccagtc tccagactcc ctggctgtgt ctctgggcga gagggccacc      60
atcatctgca gtccagcca gagtatttta tacagctcca acaataagaa ctacttaggt     120
tggtaccagc agaaaccagg acagcctcct aagctgctca tttactgggc atctacccgg    180
gaatccgggg tccctgcccg attcagtggc agcgggtctg gacagatttt cactctcacc    240
atcaacagcc tgcaggctga agatgtggca gtttattact gtcagcaata ttatagtact    300
cctcggtcgt tcggccaagg gaccatggtg gaaatcaaac                          340

<210> SEQ ID NO 25
<211> LENGTH: 119
<212> TYPE: PRT
<213> ORGANISM: Homo Sapiens

<400> SEQUENCE: 25

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Asn Ser Gly
```

```
            20                  25                  30
Gly Cys Tyr Trp Ser Trp Ile Arg Gln His Pro Gly Lys Gly Leu Glu
         35                  40                  45

Trp Ile Gly Tyr Ile Tyr Ser Ser Gly Ser Thr Tyr Tyr Asn Pro Ser
 50                  55                  60

Leu Lys Ser Arg Ile Thr Leu Ser Val Asp Thr Ser Lys Asn Gln Phe
 65                  70                  75                  80

Ser Leu Lys Leu Asn Ser Met Thr Ala Ala Asp Thr Ala Val Tyr Tyr
                 85                  90                  95

Cys Ala Arg Asp Arg Glu Thr Ala Gly Phe Asp Tyr Trp Gly Gln Gly
            100                 105                 110

Thr Leu Val Thr Val Ser Ser
        115

<210> SEQ ID NO 26
<211> LENGTH: 107
<212> TYPE: PRT
<213> ORGANISM: Homo Sapiens

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Gly Leu Gln Pro
 65                  70                  75                  80

Glu Asp Ile Ala Thr Tyr Tyr Cys Gln Gln Tyr Asp Thr Leu Pro Leu
                 85                  90                  95

Thr Phe Gly Gly Gly Thr Lys Val Glu Ile Lys
            100                 105

<210> SEQ ID NO 27
<211> LENGTH: 358
<212> TYPE: DNA
<213> ORGANISM: Homo Sapiens

<400> SEQUENCE: 27
caggtgcagc tgcaggagtc gggcccagga ctggtgaagc cttcacagac cctgtccctc      60
acctgcactg tctctggtgg ctccatcaac agtggtggtt gctactggag ctggatccgc     120
cagcacccag ggaagggcct ggagtggatt ggtacatct attccagtgg gagcacctac      180
tacaacccgt ccctcaagag tcgaattacc ttatcagtag acacgtctaa gaaccagttc     240
tccctgaagc tgaactctat gactgccgcg gacacggccg tgtattactg cgcgagagat     300
cgggaaacag ctggttttga ctactggggc cagggaaccc tggtcaccgt ctcctcag      358

<210> SEQ ID NO 28
<211> LENGTH: 322
<212> TYPE: DNA
<213> ORGANISM: Homo Sapiens

<400> SEQUENCE: 28
gacatccaga tgacccagtc tccatcctcc ctgtctgcat ctgtaggaga cagagtcacc      60
```

```
atcacttgcc aggcgagtca ggacattaac aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcgg cctgcagcct    240
gaggatattg caacatatta ctgtcaacag tatgatactc tccctctcac tttcggcggc    300
gggaccaagg tggagatcaa ac                                             322
```

<210> SEQ ID NO 29
<211> LENGTH: 120
<212> TYPE: PRT
<213> ORGANISM: Homo Sapiens

<400> SEQUENCE: 29

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Phe Gly Val Val Ile Asp Tyr Gly Met Asp Val Trp
            100                 105                 110

Gly Gln Gly Thr Thr Val Thr Val
        115                 120
```

<210> SEQ ID NO 30
<211> LENGTH: 107
<212> TYPE: PRT
<213> ORGANISM: Homo Sapiens

<400> SEQUENCE: 30

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Asn Pro Gly Lys Val Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Phe Ser Ser Pro Pro Phe
                85                  90                  95

Thr Phe Gly Pro Gly Thr Lys Val Asp Ile Ser
            100                 105
```

<210> SEQ ID NO 31
<211> LENGTH: 367
<212> TYPE: DNA
<213> ORGANISM: Homo Sapiens

<400> SEQUENCE: 31

```
caggtgcagc tggtggagtc ggggggaggc gtggtccagc ctgggaggtc cctgagactc      60
tcctgtgcag cctctggatt caccttcagt agctatgcca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gagatcgatt     300
tttggagtgg ttatcgacta cggtatggac gtctggggcc aagggaccac ggtcaccgtc     360
tcctcag                                                               367

<210> SEQ ID NO 32
<211> LENGTH: 322
<212> TYPE: DNA
<213> ORGANISM: Homo Sapiens

<400> SEQUENCE: 32
gacatccaga tgacccagtc tccatcctcc ctgtctgcat ctgtaggaga cagagtcacc      60
atcacttgcc gggcgagtca gggcattaga aattatttag cctggtatca gcagaatcca     120
gggaaagttc ctaagctcct gatctatggt gcatccactt tgcaatcagg ggtcccatct     180
cggttcagtg gcagtggatc tgggacagat ttcactctca ccatcagcag cctgcagcct     240
gaagatgttg caacttatta ctgtcaaaag tttagcagtc ccccattcac tttcggccct     300
gggaccaaag tggatatcag tc                                              322

<210> SEQ ID NO 33
<211> LENGTH: 117
<212> TYPE: PRT
<213> ORGANISM: Homo Sapiens

<400> SEQUENCE: 33
```

Gln Val Gln Leu Glu Gln Ser Gly Pro Gly Leu Val Lys Pro Ser Glu
 1               5                  10                  15

Thr Leu Ser Leu Thr Cys Thr Val Ser Gly Gly Ser Ile Ser Ser Gly
            20                  25                  30

Thr Tyr His Trp Ser Trp Ile Arg Gln His Pro Gly Arg Gly Leu Glu
        35                  40                  45

Trp Ile Gly Tyr Ile Tyr Tyr Ser Gly Ser Thr Tyr His Asn Pro Ser
    50                  55                  60

Leu Lys Ser Arg Ile Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Asp Gly Tyr Arg Tyr Trp Gly Gln Gly Thr Leu
            100                 105                 110

Val Thr Val Ser Ser
        115

```
<210> SEQ ID NO 34
<211> LENGTH: 107
<212> TYPE: PRT
<213> ORGANISM: Homo Sapiens

<400> SEQUENCE: 34
```

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Asn Asn
            20                  25                  30

Phe Ala Trp Tyr Gln Gln Lys Pro Gly Gln Ala Pro Arg Leu Leu Ile
            35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
                100                 105

<210> SEQ ID NO 35
<211> LENGTH: 352
<212> TYPE: DNA
<213> ORGANISM: Homo Sapiens

<400> SEQUENCE: 35
caggtgcagc tggagcagtc ggggccagga ctggtgaagc cttcagagac cctgtccctc      60
acctgcactg tctctggtgg ctccatcagc agtggtactt accactggag ctggatccgc     120
cagcacccag ggaggggcct ggagtggatt ggatacatct attacagtgg gagcacctac     180
cacaacccgt ccctcaagag tcgaattacc atatcagtag acacgtctaa gaaccagttc     240
tccctgaagc tgagctctgt gacggccgcg gacacggccg tgtattactg cgagaggg      300 ggagatggct acagatactg gggccaggga accctggtca ccgtctcctc ag             352

<210> SEQ ID NO 36
<211> LENGTH: 322
<212> TYPE: DNA
<213> ORGANISM: Homo Sapiens

<400> SEQUENCE: 36
gaaatagtga tgacgcagtc tccagccacc ctgtctgtgt ctccagggga aagagccacc      60
ctctcctgca gggccagtca gagtattagc aacaacttcg cctggtacca gcagaaacct     120
ggccaggctc ccaggctcct catctttggt gcatccacca gggccactgg tatcccagcc     180
aggttcagtg gcagtgggtc tgggacagaa ttcactctca ccatcagcag cctacagtct     240
gaagattttg cagtttatta ctgtcagcag tataataact ggcctcggac gttcggccaa     300
gggaccaagg tggaaatcaa ac                                              322

<210> SEQ ID NO 37
<211> LENGTH: 121
<212> TYPE: PRT
<213> ORGANISM: Homo Sapiens

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Thr Gly Asn Thr Tyr Tyr Asn Pro Ser Leu Lys
    50                  55                  60

Ser Arg Val Thr Val Ser Val Asp Thr Ser Lys Asn Gln Phe Ser Leu
65                  70                  75                  80

```
Lys Leu Asn Ser Val Thr Ala Ala Asp Thr Ala Val Tyr Tyr Cys Ala
                85                  90                  95

Arg Asp Pro Gly Gln Trp Leu Val Pro Asp Ala Phe Asp Ile Trp Gly
            100                 105                 110

Gln Gly Thr Met Val Ser Val Ser Ser
        115                 120

<210> SEQ ID NO 38
<211> LENGTH: 112
<212> TYPE: PRT
<213> ORGANISM: Homo Sapiens

<400> SEQUENCE: 38

Asp Ile Val Met Thr Gln Ser Pro Leu Ser Leu Pro Val Ile Pro Gly
 1               5                  10                  15

Glu Pro Ala Ser Ile Ser Cys Arg Ser Ser Gln Ser Leu Leu Gln Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Met Gln Ala
                85                  90                  95

Leu Gln Ile Pro Leu Thr Phe Gly Gly Gly Thr Lys Val Glu Ile Lys
            100                 105                 110

<210> SEQ ID NO 39
<211> LENGTH: 364
<212> TYPE: DNA
<213> ORGANISM: Homo Sapiens

<400> SEQUENCE: 39
caggtgcagc tgcaggagtc gggcccagga ctggtgaagc cctcggagac cctgtccctc      60
acctgcactg tctctggtgg ctccatcagt acttactact ggagttggat ccggcagccc     120
ccagggaagg gactggagtg gattggatac atctattaca ctgggaacac ctactacaac     180
ccctccctca agagtcgagt caccgtttca gttgacacgt ccaagaacca gttctccctg     240
aagctgaact ctgtgaccgc tgcggacacg gccgtgtatt actgtgcgag agatccaggc     300
cagtggctgg tccctgatgc ttttgatatc tggggccaag gacaatggt ctccgtctct     360 tcag                                                                  364

<210> SEQ ID NO 40
<211> LENGTH: 337
<212> TYPE: DNA
<213> ORGANISM: Homo Sapiens

<400> SEQUENCE: 40
gatattgtga tgactcagtc tccactctcc ctgcccgtca ttcctggaga gccggcctcc      60
atctcctgca ggtctagtca gagcctcctg cagagtaatg gaaacaacta tttggattgg     120
tacctgcaga agccagggca gtctccacag ctcctgatct atttgggttc taatcgggcc     180
```

-continued

```
tccggggtcc ctgacaggtt cagtggcagt ggatcaggca cagattttac actgaaaatc      240
agcagagtgg aggctgacga tgttgggatt tattactgca tgcaagctct ccaaattcct      300
ctcactttcg gcggagggac caaggtggag atcaaac                                337
```

What is claimed:

1. A method of inhibiting tumor growth associated with the expression of the MUC18 tumor antigen in an animal, comprising:
   selecting an animal in need of treatment for a tumor, wherein the tumor comprises cells expressing MUC18;
   providing a monoclonal antibody comprising a heavy chain amino acid sequence, wherein said heavy chain amino acid sequence is selected from the group consisting of SEQ ID NOs: 1, 5, 9, 13, 17, 21, 25, 29, 33 and 37, and wherein said monoclonal antibody binds MUC18; and
   contacting said tumor with an effective amount of said antibody, wherein said contacting results in inhibited growth of said tumor.

2. The method of claim 1, wherein said antibody is a fully human antibody.

3. The method of claim 1, wherein said antibody further comprises a light chain amino acid sequence selected from the group consisting of SEQ ID NOs: 2, 6, 10, 14, 18, 22, 26, 30, 34 and 38.

4. The method of claim 1, wherein said antibody is conjugated to a therapeutic or cytotoxic agent.

5. The method of claim 4, wherein the cytotoxic agent is ricin.

6. The method of claim 4, wherein the therapeutic agent is a radioisotope.

7. The method of claim 1, wherein said tumor is melanoma.

8. The method of claim 1, wherein said tumor is a lung tumor.

9. The method of claim 1, wherein said tumor growth is tumor metastasis.

10. A method of inhibiting cell invasion associated with melanoma, comprising:
    selecting an animal in need of treatment for melanoma;
    providing a monoclonal antibody comprising a heavy chain amino acid sequence, wherein said heavy chain amino acid sequence is selected from the group consisting of SEQ ID NOs: 1, 5, 9, 13, 17, 21, 25, 29, 33 and 37, and wherein said monoclonal antibody binds MUC18; and
    contacting said melanoma with an effective amount of said antibody, wherein said contacting results in inhibited cell invasion.

11. The method of claim 10, wherein said antibody is a fully human antibody.

12. The method of claim 10, wherein said antibody is conjugated to a therapeutic or cytotoxic agent.

13. The method of claim 12, wherein the cytotoxic agent is ricin.

14. The method of claim 12, wherein the therapeutic agent is a radioisotope.

15. A method of increasing survival of an animal having a metastatic tumor that expresses MUC18, comprising:
    selecting an animal in need of treatment for a metastatic tumor, wherein the tumor comprises cells expressing MUC18;
    providing a monoclonal antibody comprising a heavy chain amino acid sequence, wherein said heavy chain amino acid sequence is selected from the group consisting of SEQ ID NOs: 1, 5, 9,13, 17, 21, 25, 29, 33 and 37, and wherein said monoclonal antibody binds MUC18; and
    contacting said animal with an effective amount of said antibody, wherein said contacting results in inhibited metastasis of said tumor resulting in increased survival of said animal.

16. The method of claim 15, wherein said antibody is a fully human antibody.

17. The method of claim 15, wherein said antibody is conjugated to a therapeutic or cytotoxic agent.

18. The method of claim 17, wherein the cytotoxic agent is ricin.

19. The method of claim 17, wherein the therapeutic agent is a radioisotope.

20. The method of claim 1, wherein the heavy chain amino acid sequence is SEQ ID NO: 1.

21. The method of claim 3, wherein heavy chain amino acid sequence is SEQ ID NO: 1 and the light chain amino acid sequence is SEQ ID NO: 2.

22. The method of claim 10, wherein the heavy chain amino acid sequence is SEQ ID NO: 1.

23. The method of claim 10, wherein said antibody further comprises a light chain amino acid sequence selected from the group consisting of SEQ ID NOs: 2, 6, 10, 14, 18, 22, 26, 30, 34 and 38.

24. The method of claim 23, wherein heavy chain amino acid sequence is SEQ ID NO: 1 and the light chain amino acid sequence is SEQ ID NO: 2.

25. The method of claim 15, wherein the heavy chain amino acid sequence is SEQ ID NO: 1.

26. The method of claim 15, wherein said antibody further comprises a light chain amino acid sequence selected from the group consisting of SEQ ID NOs: 2, 6, 10, 14, 18, 22, 26, 30, 34 and 38.

27. The method of claim 26, wherein heavy chain amino acid sequence is SEQ ID NO: 1 and the light chain amino acid sequence is SEQ ID NO: 2.

* * * * *

UNITED STATES PATENT AND TRADEMARK OFFICE
CERTIFICATE OF CORRECTION

PATENT NO.         : 7,090,844 B2
APPLICATION NO. : 10/660357
DATED                 : August 15, 2006
INVENTOR(S)       : Bar-Eli et al.

It is certified that error appears in the above-identified patent and that said Letters Patent is hereby corrected as shown below:

On the Title page, Col. 1 Item [73] (Assignee), line 1, please delete "Fremont, CA (US)" and insert --6701 Kaiser Drive, Fremont, CA (US) 94555--, therefor.

On the Title page, Col. 1 Item [56] (Other Publications), line 2, please delete "Long" and insert --Longo,--, therefor.

On the Title page, Col. 2 Item [56] (Other Publications), line 5, please delete "Onocology," and insert --Oncology,--, therefor.

On the Title page, Col. 2 Item [56] (Other Publications), line 8, please delete "Bio," and insert --Bio.--, therefor.

On the Title page, Col. 2 Item [56] (Other Publications), line 17, after "Receptor-Targeted" please insert --Therapy--.

On Page 2, Col. 1 Item [56] (Other Publications), line 27, please delete "of" and insert --on--, therefor.

On Page 2, Col. 1 Item [56] (Other Publications), line 31, please delete "ovearian" and insert --ovarian--, therefor.

On Page 2, Col. 1 Item [56] (Other Publications), line 38, please delete "T-Lymphocytes,"" and insert --T Lymphocytes,"--, therefor.

On Page 2, Col. 1 Item [56] (Other Publications), line 55, please delete "Spread$^1$"" and insert --Spread$^1$,--, therefor.

On Page 2, Col. 1 Item [56] (Other Publications), line 58, please delete "62:5108" and insert --62:5106--, therefor.

On Page 2, Col. 1 Item [56] (Other Publications), line 62, please delete "Breat" and insert --Breast--, therefor.

On Page 2, Col. 1 Item [56] (Other Publications), line 64, please delete "Trough" and insert --Through--, therefor.

On Page 2, Col. 2 Item [56] (Other Publications), line 18, please delete "tratment" and insert --treatment--, therefor.

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

On Page 2, Col. 2 Item [56] (Other Publications), line 32, please delete "tranplant" and insert --transplant--, therefor.

In Col. 1, line 39, please delete "Devel," and insert --Devel.,--, therefor.

In Col. 2, line 57, please delete "MUC-18" and insert --MUC18--, therefor.

In Col. 3, line 39, please delete "MUC 18;" and insert --MUC18;--, therefor.

In Col. 7, line 40, please delete "85)." and insert --85),--, therefor.

In Col. 7, line 52, please delete "microbiology" and insert --Microbiology--, therefor.

In Col. 8, line 14, please delete "MUC 18;" and insert --MUC18;--, therefor.

In Col. 8, line 51, please delete "lymphomma," and insert --lymphoma,--, therefor.

In Col. 8, line 67, please delete "glycoproteeins" and insert --glycoproteins--, therefor.

In Col. 9, line 24, please delete "Biol" and insert --Biol.--, therefor.

In Col. 9, line 25, please delete "et al." and insert --et al.,--, therefor.

In Col. 9, line 44, please delete "$\epsilon$" and insert --$\varepsilon$,--, therefor.

In Col. 9, line 45, please delete "subuniit" and insert --subunit--, therefor.

In Col. 10, line 16, please delete "pertinacious" and insert --proteinaceous--, therefor.

In Col. 12, line 33, please delete "Carryying" and insert --Carrying--, therefor.

In Col. 13, line 22, please delete "MC11" and insert --MC.-11--, therefor.

In Col. 13, lines 53-54, please delete "hydroxylapatiite" and insert --hydroxylapatite--, therefor.

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

In Col. 14, line 39, please delete "oncoproteiin" and insert --oncoprotein--, therefor.

In Col. 15, line 32 (approx.), please delete "et al," and insert --et al.,--, therefor.

In Col. 21, lines 39-42 (approx.), please delete
"Forward primer: 5'-ATATTACGAATTCACT-TGCGTCTCGCCCTCCGG-3'(SEQ ID NO :83) Reverse primer: 5'-CAGCTTAGAGCTAGCCGGCTCTCCG-GCTCCGGCA-3'(SEQ ID NO:-14 84)"

In Col. 23, line 24, please delete "c6.12," and insert --c6.12.--, therefor.

In Col. 23, line 36, please delete "(c6.11)," and insert --(c6.11).--, therefor.

In Col. 24, line 13 (approx.), please delete "400µI" and insert --400 µl--, therefor.

In Col. 24, line 27, please delete "nonrmetastatic" and insert --nonmetastatic--, therefor.

In Col. 26, line 59 (approx.), please delete "pnase," and insert --phase,--, therefor.

In Col. 27, line 59, please delete "anti-MUC 18" and insert --anti-MUC18--, therefor.

In Col. 28, line 44 (approx.), please delete "Matrigel- Coated" and insert --Matrigel-Coated--, therefor.

In Col. 57, line 6, please insert:

```
--<210> 41
<211> 97
<212> PRT
<213> Homo sapiens

<400> 41
Gln Val Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser Ser Tyr
                20                  25                  30
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
        Tyr Trp Ser Trp Ile Arg Gln Pro Pro Gly Lys Gly Leu Glu Trp Ile
                    35                  40                  45
        Gly Tyr Ile Tyr Tyr Ser Gly Ser Thr Asn Tyr Asn Pro Ser Leu Lys
                    50                  55                  60
        Ser Arg Val Thr Ile Ser Val Asp Thr Ser Lys Asn Gln Phe Ser Leu
        65                  70                  75                  80
        Lys Leu Ser Ser Val Thr Ala Ala Asp Thr Ala Val Tyr Tyr Cys Ala
                            85                  90                  95
        Arg

<210> 42
        <211> 96
        <212> PRT
        <213> Homo sapiens

<400> 42
        Gln Val Gln Leu Gln Glu Ser Gly Pro Gly Leu Val Lys Pro Ser Glu
        1               5                   10                  15
        Thr Leu Ser Leu Thr Cys Thr Val Ser Gly Gly Ser Ile Ser Ser Tyr
                            20                  25                  30
        Tyr Trp Ser Trp Ile Arg Gln Pro Pro Gly Lys Gly Leu Glu Trp Ile
                    35                  40                  45
        Gly Tyr Ile Tyr Tyr Ser Ser Thr Asn Tyr Asn Pro Ser Leu Lys Ser
                    50                  55                  60
        Arg Val Thr Ile Ser Val Asp Thr Ser Lys Asn Gln Phe Ser Leu Lys
        65                  70                  75                  80
        Leu Ser Ser Val Thr Ala Ala Asp Thr Ala Leu Tyr Tyr Cys Ala Arg
                            85                  90                  95

<210> 43
        <211> 95
        <212> PRT
        <213> Homo sapiens

<400> 43
        Asp Ile Gln Met Thr Gln Ser Pro Ser Ser Leu Ser Ala Ser Val Gly
        1               5                   10                  15
        Asp Arg Val Thr Ile Thr Cys Arg Ala Ser Gln Ser Ile Ser Ser Tyr
                            20                  25                  30
        Leu Asn Trp Tyr Gln Gln Lys Pro Gly Lys Ala Pro Lys Leu Leu Ile
                    35                  40                  45
        Tyr Ala Ala Ser Ser Leu Gln Ser Gly Val Pro Ser Arg Phe Ser Gly
                    50                  55                  60
        Ser Gly Ser Gly Thr Asp Phe Thr Leu Thr Ile Ser Ser Leu Gln Pro
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
                65                    70                    75                    80
        Glu Asp Phe Ala Thr Tyr Tyr Cys Gln Gln Ser Tyr Ser Thr Pro
                            85                    90                    95

<210> 44
        <211> 93
        <212> PRT
        <213> Homo sapiens

<400> 44
        Asp Ile Gln Met Thr Gln Ser Pro Ser Ser Leu Ser Ala Ser Val Gly
        1                   5                   10                  15
        Asp Arg Val Thr Ile Thr Cys Arg Ala Ser Gln Ser Ile Ser Tyr Leu
                            20                  25                  30
        Asn Trp Tyr Gln Gln Lys Pro Gly Lys Ala Pro Lys Leu Leu Ile Tyr
                        35                  40                  45
        Ala Ala Ser Ser Leu Gln Ser Gly Val Pro Ser Arg Phe Ser Gly Ser
                    50                  55                  60
        Gly Ser Gly Thr Asp Phe Thr Leu Thr Ile Ser Ser Leu Gln Pro Glu
        65                      70                  75                      80
        Asp Phe Ala Thr Tyr Tyr Cys Gln Ser Tyr Ser Thr Pro
                            85                  90

<210> 45
        <211> 99
        <212> PRT
        <213> Homo sapiens

<400> 45
        Gln Val Gln Leu Gln Glu Ser Gly Pro Gly Leu Val Lys Pro Ser Gln
        1                   5                   10                  15
        Thr Leu Ser Leu Thr Cys Thr Val Ser Gly Gly Ser Ile Ser Ser Gly
                            20                  25                  30
        Gly Tyr Tyr Trp Ser Trp Ile Arg Gln His Pro Gly Lys Gly Leu Glu
```

UNITED STATES PATENT AND TRADEMARK OFFICE
CERTIFICATE OF CORRECTION

PATENT NO. : 7,090,844 B2  
APPLICATION NO. : 10/660357  
DATED : August 15, 2006  
INVENTOR(S) : Bar-Eli et al.

It is certified that error appears in the above-identified patent and that said Letters Patent is hereby corrected as shown below:

```
              35                   40                   45
    Trp Ile Gly Tyr Ile Tyr Tyr Ser Gly Ser Thr Tyr Tyr Asn Pro Ser
        50                   55                   60
    Leu Lys Ser Arg Val Thr Ile Ser Val Asp Thr Ser Lys Asn Gln Phe
    65                   70                   75                   80
    Ser Leu Lys Leu Ser Ser Val Thr Ala Ala Asp Thr Ala Val Tyr Tyr
                        85                   90                   95
    Cys Ala Arg

<210> 46
    <211> 99
    <212> PRT
    <213> Homo sapiens

<400> 46
    Gln Val Gln Leu Gln Glu Ser Gly Pro Gly Leu Val Lys Pro Ser Gln
    1                    5                   10                   15
    Thr Leu Ser Leu Thr Cys Thr Val Ser Gly Gly Ser Ile Ser Ser Gly
                        20                   25                   30
    Gly Tyr Tyr Trp Ser Trp Ile Arg Gln His Pro Gly Lys Gly Leu Glu
                35                   40                   45
    Trp Ile Gly Phe Ile Tyr Tyr Ser Gly Ser Thr Tyr Tyr Asn Pro Ser
        50                   55                   60
    Leu Lys Ser Arg Val Thr Ile Ser Val Asp Thr Ser Lys Asn Gln Phe
    65                   70                   75                   80
    Ser Leu Lys Leu Ser Ser Val Thr Ala Ala Asp Thr Ala Val Tyr Tyr
                        85                   90                   95
    Cys Ala Arg

<210> 47
    <211> 95
    <212> PRT
    <213> Homo sapiens
```

UNITED STATES PATENT AND TRADEMARK OFFICE
CERTIFICATE OF CORRECTION

PATENT NO.       : 7,090,844 B2
APPLICATION NO.  : 10/660357
DATED            : August 15, 2006
INVENTOR(S)      : Bar-Eli et al.

It is certified that error appears in the above-identified patent and that said Letters Patent is hereby corrected as shown below:

```
<400> 47
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
             20                  25                  30
Leu Gly Trp Tyr Gln Gln Lys Pro Gly Lys Ala Pro Lys Arg Leu Ile
             35                  40                  45
Tyr Ala Ala Ser Ser Leu Gln Ser Gly Val Pro Ser Arg Phe Ser Gly
             50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro
                     85                  90                  95

<210> 48
<211> 95
<212> PRT
<213> Homo sapiens

<400> 48
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
             20                  25                  30
Leu Gly Trp Tyr Gln Gln Lys Pro Gly Lys Ala Pro Lys Arg Leu Ile
             35                  40                  45
Tyr Ala Ala Ser Ser Leu Gln Ser Gly Val Pro Ser Arg Phe Ser Gly
             50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro
                     85                  90                  95
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
<210> 49
<211> 97
<212> PRT
<213> Homo sapiens

<400> 49
Gln Val Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg

<210> 50
<211> 96
<212> PRT
<213> Homo sapiens

<400> 50
Gln Val Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Ser Ser Asn Tyr Asn Pro Ser Leu Lys Ser
    50                  55                  60
Arg Val Thr Ile Ser Val Asp Thr Ser Lys Asn Gln Phe Ser Leu Lys
65                  70                  75                  80
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
        Leu Ser Ser Val Thr Ala Ala Asp Thr Ala Val Tyr Tyr Cys Ala Arg
                        85              90                  95

<210> 51
        <211> 95
        <212> PRT
        <213> Homo sapiens

<400> 51
        Asp Ile Gln Met Thr Gln Ser Pro Ser Ser Leu Ser Ala Ser Val Gly
        1               5                   10                  15
        Asp Arg Val Thr Ile Thr Cys Arg Ala Ser Gln Gly Ile Arg Asn Asp
                        20                  25                  30
        Leu Gly Trp Tyr Gln Gln Lys Pro Gly Lys Ala Pro Lys Arg Leu Ile
                        35                  40                  45
        Tyr Ala Ala Ser Ser Leu Gln Ser Gly Val Pro Ser Arg Phe Ser Gly
                        50                  55                  60
        Ser Gly Ser Gly Thr Glu Phe Thr Leu Thr Ile Ser Ser Leu Gln Pro
        65                  70                  75                  80
        Glu Asp Phe Ala Thr Tyr Tyr Cys Leu Gln His Asn Ser Tyr Pro
                        85                  90                  95

<210> 52
        <211> 95
        <212> PRT
        <213> Homo sapiens

<400> 52
        Asp Ile Gln Met Thr Gln Ser Pro Ser Ser Leu Ser Ala Ser Val Gly
        1               5                   10                  15
        Asp Arg Val Thr Ile Thr Cys Arg Ala Ser Gln Gly Ile Arg Asn Asp
                        20                  25                  30
        Leu Gly Trp Tyr Gln Gln Lys Pro Gly Lys Ala Pro Lys Arg Leu Ile
                        35                  40                  45
        Tyr Ala Ala Ser Ser Leu Gln Ser Gly Val Pro Ser Arg Phe Ser Gly
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
                 50                  55                  60
    Ser Gly Ser Gly Thr Glu Phe Thr Leu Thr Ile Ser Ser Leu Gln Pro
    65                  70                  75                  80
    Glu Asp Phe Ala Thr Tyr Tyr Cys Leu Gln His Asn Ser Tyr Pro
                            85                  90                  95

<210> 53
    <211> 98
    <212> PRT
    <213> Homo sapiens

<400> 53
    Gln Val Gln Leu Val Gln Ser Gly Ala Glu Val Lys Lys Pro Gly Ala
    1               5                   10                  15
    Ser Val Lys Val Ser Cys Lys Ala Ser Gly Tyr Thr Phe Thr Ser Tyr
                    20                  25                  30
    Gly Ile Ser Trp Val Arg Gln Ala Pro Gly Gln Gly Leu Glu Trp Met
                35                  40                  45
    Gly Trp Ile Ser Ala Tyr Asn Gly Asn Thr Asn Tyr Ala Gln Lys Leu
            50                  55                  60
    Gln Gly Arg Val Thr Met Thr Thr Asp Thr Ser Thr Ser Thr Ala Tyr
    65                  70                  75                  80
    Met Glu Leu Arg Ser Leu Arg Ser Asp Asp Thr Ala Val Tyr Tyr Cys
                            85                  90                  95
    Ala Arg

<210> 54
    <211> 96
    <212> PRT
    <213> Homo sapiens

<400> 54
    Gln Val Gln Leu Val Gln Ser Gly Ala Glu Val Lys Lys Pro Gly Ala
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
        1               5              10              15
    Ser Val Lys Val Ser Cys Lys Ala Ser Gly Tyr Thr Phe Ser Tyr Gly
                20              25              30
    Ser Trp Val Arg Gln Ala Pro Gly Gln Gly Leu Glu Trp Leu Gly Trp
                35              40              45
    Ile Ser Ala Tyr Asn Gly Asn Thr Asn Tyr Ala Gln Lys Leu Gln Gly
                50              55              60
    Arg Val Thr Met Thr Thr Asp Thr Ser Thr Ser Thr Ala Tyr Met Glu
    65              70              75                              80
    Leu Arg Ser Leu Arg Ser Asp Asp Thr Ala Val Tyr Tyr Cys Ala Arg
                    85              90              95

<210> 55
    <211> 101
    <212> PRT
    <213> Homo sapiens

<400> 55
    Asp Ile Val Met Thr Gln Ser Pro Asp Ser Leu Ala Val Ser Leu Gly
    1               5               10              15
    Glu Arg Ala Thr Ile Asn Cys Lys Ser Ser Gln Ser Val Leu Tyr Ser
                20              25              30
    Ser Asn Asn Lys Asn Tyr Leu Ala Trp Tyr Gln Gln Lys Pro Gly Gln
                35              40              45
    Pro Pro Lys Leu Leu Ile Tyr Trp Ala Ser Thr Arg Glu Ser Gly Val
                50              55              60
    Pro Asp Arg Phe Ser Gly Ser Gly Ser Gly Thr Asp Phe Thr Leu Thr
    65              70              75                              80
    Ile Ser Ser Leu Gln Ala Glu Asp Val Ala Val Tyr Tyr Cys Gln Gln
                    85              90              95
    Tyr Tyr Ser Thr Pro
                    100

<210> 56
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
<211> 98
<212> PRT
<213> Homo sapiens

<400> 56
Asp Ile Val Met Thr Gln Ser Pro Asp Ser Leu Ala Val Ser Leu Gly
1               5                   10                  15
Glu Arg Ala Thr Ile Cys Lys Ser Ser Gln Ser Ile Leu Tyr Ser Ser
                20                  25                  30
Asn Asn Lys Asn Tyr Leu Ala Trp Tyr Gln Gln Lys Pro Gly Gln Pro
            35                  40                  45
Pro Lys Leu Leu Ile Tyr Trp Ala Ser Thr Arg Glu Ser Gly Val Pro
        50                  55                  60
Arg Phe Ser Gly Ser Gly Ser Gly Thr Asp Phe Thr Leu Thr Ile Ser
65                  70                  75                  80
Leu Gln Ala Glu Asp Val Ala Val Tyr Tyr Cys Gln Gln Tyr Tyr Ser
                85                  90                  95
Thr Pro

<210> 57
<211> 99
<212> PRT
<213> Homo sapiens

<400> 57
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
                20                  25                  30
Gly Tyr Tyr Trp Ser Trp Ile Arg Gln His Pro Gly Lys Gly Leu Glu
            35                  40                  45
Trp Ile Gly Tyr Ile Tyr Tyr Ser Gly Ser Thr Tyr Tyr Asn Pro Ser
        50                  55                  60
Leu Lys Ser Arg Val Thr Ile Ser Val Asp Thr Ser Lys Asn Gln Phe
65                  70                  75                  80
```

UNITED STATES PATENT AND TRADEMARK OFFICE
CERTIFICATE OF CORRECTION

PATENT NO. : 7,090,844 B2  
APPLICATION NO. : 10/660357  
DATED : August 15, 2006  
INVENTOR(S) : Bar-Eli et al.

Page 13 of 29

It is certified that error appears in the above-identified patent and that said Letters Patent is hereby corrected as shown below:

```
        Ser Leu Lys Leu Ser Ser Val Thr Ala Ala Asp Thr Ala Val Tyr Tyr
                        85              90                  95
        Cys Ala Arg

<210> 58
        <211> 95
        <212> PRT
        <213> Homo sapiens

<400> 58
        Gln Val Gln Leu Gln Glu Ser Gly Pro Gly Leu Val Lys Pro Ser Gln
        1               5                   10                  15
        Thr Leu Ser Leu Thr Cys Thr Val Ser Gly Gly Ser Ile Ser Gly Gly
                        20                  25                  30
        Tyr Trp Ser Trp Ile Arg Gln His Pro Gly Lys Gly Leu Glu Trp Ile
                        35                  40                  45
        Gly Tyr Ile Tyr Ser Gly Ser Thr Tyr Tyr Asn Pro Ser Leu Lys Ser
                    50              55                  60
        Arg Ile Thr Ile Ser Val Asp Thr Ser Lys Asn Gln Phe Ser Leu Lys
        65                  70                  75                  80
        Leu Ser Met Thr Ala Ala Asp Thr Ala Val Tyr Tyr Cys Ala Arg
                        85                  90                  95

<210> 59
        <211> 95
        <212> PRT
        <213> Homo sapiens

<400> 59
        Asp Ile Gln Met Thr Gln Ser Pro Ser Ser Leu Ser Ala Ser Val Gly
        1               5                   10                  15
        Asp Arg Val Thr Ile Thr Cys Gln Ala Ser Gln Asp Ile Ser Asn Tyr
                        20                  25                  30
        Leu Asn Trp Tyr Gln Gln Lys Pro Gly Lys Ala Pro Lys Leu Leu Ile
                        35                  40                  45
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
        Tyr Asp Ala Ser Asn Leu Glu Thr Gly Val Pro Ser Arg Phe Ser Gly
                50                  55                  60
        Ser Gly Ser Gly Thr Asp Phe Thr Phe Thr Ile Ser Ser Leu Gln Pro
        65                  70                  75                  80
        Glu Asp Ile Ala Thr Tyr Tyr Cys Gln Gln Tyr Asp Asn Leu Pro
                        85                  90                  95

<210> 60
        <211> 92
        <212> PRT
        <213> Homo sapiens

<400> 60
        Asp Ile Gln Met Thr Gln Ser Pro Ser Ser Leu Ser Ala Ser Val Gly
        1               5                   10                  15
        Asp Arg Val Thr Ile Thr Cys Gln Ala Ser Gln Asp Ile Asn Tyr Leu
                        20                  25                  30
        Asn Trp Tyr Gln Gln Lys Pro Gly Lys Ala Pro Lys Leu Leu Ile Tyr
                    35                  40                  45
        Asp Ala Ser Asn Leu Glu Thr Gly Val Pro Ser Arg Phe Ser Gly Ser
                50                  55                  60
        Gly Ser Gly Thr Asp Phe Thr Phe Thr Ile Ser Leu Gln Pro Glu Asp
        65                  70                  75                  80
        Ile Ala Thr Tyr Tyr Cys Gln Gln Tyr Asp Leu Pro
                        85                  90

<210> 61
        <211> 98
        <212> PRT
        <213> Homo sapiens

<400> 61
        Gln Val Gln Leu Val Glu Ser Gly Gly Gly Val Val Gln Pro Gly Arg
        1               5                   10                  15
        Ser Leu Arg Leu Ser Cys Ala Ala Ser Gly Phe Thr Phe Ser Ser Tyr
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
                    20                  25                  30
        Gly Met His Trp Val Arg Gln Ala Pro Gly Lys Gly Leu Glu Trp Val
                    35                  40                  45
        Ala Val Ile Ser Tyr Asp Gly Ser Asn Lys Tyr Tyr Ala Asp Ser Val
                    50                  55                  60
        Lys Gly Arg Phe Thr Ile Ser Arg Asp Asn Ser Lys Asn Thr Leu Tyr
        65                  70                  75                  80
        Leu Gln Met Asn Ser Leu Arg Ala Glu Asp Thr Ala Val Tyr Tyr Cys
                            85                  90                  95
        Ala Arg

<210> 62
        <211> 98
        <212> PRT
        <213> Homo sapiens

<400> 62
        Gln Val Gln Leu Val Glu Ser Gly Gly Gly Val Val Gln Pro Gly Arg
        1                   5                   10                  15
        Ser Leu Arg Leu Ser Cys Ala Ala Ser Gly Phe Thr Phe Ser Ser Tyr
                            20                  25                  30
        Ala Met His Trp Val Arg Gln Ala Pro Gly Lys Gly Leu Glu Trp Val
                    35                  40                  45
        Ala Val Ile Ser Tyr Asp Gly Ser Asn Lys Tyr Tyr Ala Asp Ser Val
                    50                  55                  60
        Lys Gly Arg Phe Thr Ile Ser Arg Asp Asn Ser Lys Asn Thr Leu Tyr
        65                  70                  75                  80
        Leu Gln Met Asn Ser Leu Arg Ala Glu Asp Thr Ala Val Tyr Tyr Cys
                            85                  90                  95
        Ala Arg

<210> 63
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
<211> 95
<212> PRT
<213> Homo sapiens

<400> 63
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Ser Asn Tyr
                20                  25                  30
Leu Ala Trp Tyr Gln Gln Lys Pro Gly Lys Val Pro Lys Leu Leu Ile
                35                  40                  45
Tyr Ala Ala Ser Thr Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Lys Tyr Asn Ser Ala Pro
                    85                  90                  95

<210> 64
<211> 91
<212> PRT
<213> Homo sapiens

<400> 64
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Asn Tyr Leu
                20                  25                  30
Ala Trp Tyr Gln Gln Pro Gly Lys Val Pro Lys Leu Leu Ile Tyr Ala
                35                  40                  45
Ala Ser Thr Leu Gln Ser Gly Val Pro Ser Arg Phe Ser Gly Ser Gly
 50                  55                  60
Ser Gly Thr Asp Phe Thr Leu Thr Ile Ser Ser Leu Gln Pro Glu Asp
 65                  70                  75                  80
Val Ala Thr Tyr Tyr Cys Gln Lys Phe Ser Pro
                    85                  90
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
<210> 65
<211> 99
<212> PRT
<213> Homo sapiens

<400> 65
Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
             20                  25                  30
Gly Tyr Tyr Trp Ser Trp Ile Arg Gln His Pro Gly Lys Gly Leu Glu
         35                  40                  45
Trp Ile Gly Tyr Ile Tyr Tyr Ser Gly Ser Thr Tyr Tyr Asn Pro Ser
     50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg

<210> 66
<211> 95
<212> PRT
<213> Homo sapiens

<400> 66
Gln Val Gln Leu Ser Gly Pro Gly Leu Val Lys Pro Ser Thr Leu Ser
 1               5                  10                  15
Leu Thr Cys Thr Val Ser Gly Gly Ser Ile Ser Ser Gly Tyr His Trp
             20                  25                  30
Ser Trp Ile Arg Gln His Pro Gly Lys Gly Leu Glu Trp Ile Gly Tyr
         35                  40                  45
Ile Tyr Tyr Ser Gly Ser Thr Tyr His Asn Pro Ser Leu Lys Ser Arg
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
                50                      55                      60
        Ile Thr Ile Ser Val Asp Thr Ser Lys Asn Gln Phe Ser Leu Lys Leu
        65                  70                  75                  80
        Ser Ser Val Thr Ala Ala Asp Thr Ala Val Tyr Tyr Cys Ala Arg
                        85                  90                  95

<210> 67
<211> 107
<212> PRT
<213> Homo sapiens

<400> 67
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Ile Ser Asn Asn
                20                  25                  30
Phe Ala Trp Tyr Gln Gln Lys Pro Gly Gln Ala Pro Arg Leu Leu Ile
            35                  40                  45
Phe Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Arg
                85                  90                  95
Thr Phe Gly Gln Gly Thr Lys Val Glu Ile Lys
                100                 105

<210> 68
<211> 93
<212> PRT
<213> Homo sapiens

<400> 68
Glu Ile Val Met Thr Gln Ser Pro Ala Thr Leu Ser Val Ser Pro Gly
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
            1               5                   10                  15
    Glu Arg Ala Thr Leu Ser Cys Arg Ala Ser Gln Ser Ile Ser Asn Ala
                    20                  25                  30
    Trp Tyr Gln Gln Lys Pro Gly Gln Ala Pro Arg Leu Leu Ile Phe Gly
                    35                  40                  45
    Ala Ser Thr Arg Ala Thr Gly Ile Pro Ala Arg Phe Ser Gly Ser Gly
                    50                  55                  60
    Ser Gly Thr Glu Phe Thr Leu Thr Ile Ser Ser Leu Gln Ser Glu Asp
    65                  70                  75                  80
    Phe Ala Val Tyr Tyr Cys Gln Gln Tyr Asn Asn Trp Pro
                    85                  90

<210> 69
    <211> 97
    <212> PRT
    <213> Homo sapiens

<400> 69
    Gln Val Gln Leu Gln Glu Ser Gly Pro Gly Leu Val Lys Pro Ser Glu
    1                   5                   10                  15
    Thr Leu Ser Leu Thr Cys Thr Val Ser Gly Gly Ser Ile Ser Ser Tyr
                    20                  25                  30
    Tyr Trp Ser Trp Ile Arg Gln Pro Pro Gly Lys Gly Leu Glu Trp Ile
                    35                  40                  45
    Gly Tyr Ile Tyr Tyr Ser Gly Ser Thr Asn Tyr Asn Pro Ser Leu Lys
                    50                  55                  60
    Ser Arg Val Thr Ile Ser Val Asp Thr Ser Lys Asn Gln Phe Ser Leu
    65                  70                  75                  80
    Lys Leu Ser Ser Val Thr Ala Ala Asp Thr Ala Val Tyr Tyr Cys Ala
                    85                  90                  95
    Arg

<210> 70
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
<211> 94
<212> PRT
<213> Homo sapiens

<400> 70
Gln Val Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Thr Tyr Asn Pro Ser Leu Lys Ser Arg
    50                  55                  60
Val Thr Ile Ser Val Asp Thr Ser Lys Asn Gln Phe Ser Leu Lys Leu
65                  70                  75                  80
Ser Val Thr Ala Ala Asp Thr Ala Val Tyr Tyr Cys Ala Arg
                    85                  90

<210> 71
<211> 100
<212> PRT
<213> Homo sapiens

<400> 71
Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                    85                  90                  95
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
Leu Gln Thr Pro
            100
<210> 72
<211> 96
<212> PRT
<213> Homo sapiens
<400> 72
Asp Ile Val Met Thr Gln Ser Pro Leu Ser Leu Pro Val Pro Gly Glu
1               5                   10                  15
Pro Ala Ser Ile Ser Cys Arg Ser Ser Gln Ser Leu Leu Ser Asn Gly
                20                  25                  30
Asn Tyr Leu Asp Trp Tyr Leu Gln Lys Pro Gly Gln Ser Pro Gln Leu
            35                  40                  45
Leu Ile Tyr Leu Gly Ser Asn Arg Ala Ser Gly Val Pro Asp Arg Phe
        50                  55                  60
Ser Gly Ser Gly Ser Gly Thr Asp Phe Thr Leu Lys Ile Ser Arg Val
65                  70                  75                  80
Glu Ala Asp Asp Val Gly Ile Tyr Tyr Cys Met Gln Ala Leu Gln Pro
                85                  90                  95

<210> 73
<211> 99
<212> PRT
<213> Homo sapiens

<400> 73
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
                20                  25                  30
Gly Tyr Tyr Trp Ser Trp Ile Arg Gln His Pro Gly Lys Gly Leu Glu
            35                  40                  45
Trp Ile Gly Tyr Ile Tyr Tyr Ser Gly Ser Thr Tyr Tyr Asn Pro Ser
        50                  55                  60
Leu Lys Ser Arg Val Thr Ile Ser Val Asp Thr Ser Lys Asn Gln Phe
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
            65                  70                  75                  80
    Ser Leu Lys Leu Ser Ser Val Thr Ala Ala Asp Thr Ala Val Tyr Tyr
                    85                  90                  95
    Cys Ala Arg

<210> 74
<211> 95
<212> PRT
<213> Homo sapiens

<400> 74
Gln Val Gln Leu Ser Gly Pro Gly Leu Val Lys Pro Ser Thr Leu Ser
1               5                   10                  15
Leu Thr Cys Thr Val Ser Gly Gly Ser Ile Ser Ser Gly Tyr His Trp
                20                  25                  30
Ser Trp Ile Arg Gln His Pro Gly Lys Gly Leu Glu Trp Ile Gly Tyr
                35                  40                  45
Ile Tyr Tyr Ser Gly Ser Thr Tyr His Asn Pro Ser Leu Lys Ser Arg
            50                  55                  60
Ile Thr Ile Ser Val Asp Thr Ser Lys Asn Gln Phe Ser Leu Lys Leu
65                  70                  75                  80
Ser Ser Val Thr Ala Ala Asp Thr Ala Val Tyr Tyr Cys Ala Arg
                85                  90                  95

<210> 75
<211> 95
<212> PRT
<213> Homo sapiens

<400> 75
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
                    20                  25                  30
    Leu Ala Trp Tyr Gln Gln Lys Pro Gly Gln Ala Pro Arg Leu Leu Ile
                35                  40                  45
    Tyr Gly Ala Ser Thr Arg Ala Thr Gly Ile Pro Ala Arg Phe Ser Gly
                50                  55                  60
    Ser Gly Ser Gly Thr Glu Phe Thr Leu Thr Ile Ser Ser Leu Gln Ser
     65                  70                  75                  80
    Glu Asp Phe Ala Val Tyr Tyr Cys Gln Gln Tyr Asn Asn Trp Pro
                        85                  90                  95

<210> 76
    <211> 93
    <212> PRT
    <213> Homo sapiens

<400> 76
    Glu Ile Val Met Thr Gln Ser Pro Ala Thr Leu Ser Val Ser Pro Gly
     1               5                  10                  15
    Glu Arg Ala Thr Leu Ser Cys Arg Ala Ser Gln Ser Ile Ser Asn Ala
                20                  25                  30
    Trp Tyr Gln Gln Lys Pro Gly Gln Ala Pro Arg Leu Leu Ile Phe Gly
                35                  40                  45
    Ala Ser Thr Arg Ala Thr Gly Ile Pro Ala Arg Phe Ser Gly Ser Gly
                50                  55                  60
    Ser Gly Thr Glu Phe Thr Leu Thr Ile Ser Ser Leu Gln Ser Glu Asp
     65                  70                  75                  80
    Phe Ala Val Tyr Tyr Cys Gln Gln Tyr Asn Asn Trp Pro
                        85                  90

<210> 77
    <211> 99
    <212> PRT
    <213> Homo sapiens
```

UNITED STATES PATENT AND TRADEMARK OFFICE
CERTIFICATE OF CORRECTION

PATENT NO.       : 7,090,844 B2
APPLICATION NO.  : 10/660357
DATED            : August 15, 2006
INVENTOR(S)      : Bar-Eli et al.

It is certified that error appears in the above-identified patent and that said Letters Patent is hereby corrected as shown below:

```
<400> 77
Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
            20                  25                  30
Gly Tyr Tyr Trp Ser Trp Ile Arg Gln His Pro Gly Lys Gly Leu Glu
        35                  40                  45
Trp Ile Gly Tyr Ile Tyr Tyr Ser Gly Ser Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg

<210> 78
<211> 98
<212> PRT
<213> Homo sapiens

<400> 78
Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
            20                  25                  30
Tyr His Trp Ser Trp Ile Arg Gln His Pro Gly Lys Gly Leu Glu Trp
        35                  40                  45
Ile Gly Tyr Ile Tyr Tyr Ser Gly Ser Thr Tyr Tyr Asn Pro Ser Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
Ala Arg

<210> 79
<211> 95
<212> PRT
<213> Homo sapiens

<400> 79
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
                20                  25                  30
Leu Ala Trp Tyr Gln Gln Lys Pro Gly Gln Ala Pro Arg Leu Leu Ile
            35                  40                  45
Tyr Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro
                85                  90                  95

<210> 80
<211> 105
<212> PRT
<213> Homo sapiens

<400> 80
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Asn Leu
                20                  25                  30
Ala Trp Tyr Gln Gln Lys Pro Gly Gln Ala Pro Arg Leu Leu Ile Tyr
            35                  40                  45
Gly Ala Ser Thr Arg Ala Thr Gly Ile Pro Ala Arg Phe Ser Gly Ser
        50                  55                  60
Gly Ser Gly Thr Glu Phe Thr Leu Thr Ile Ser Ser Leu Gln Ser Glu
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
              65                  70                  75                  80
    Asp Phe Ala Val Tyr Tyr Cys Gln Gln Tyr Asn Asn Trp Pro Trp Gly
                        85                  90                  95
    Gln Gly Thr Leu Val Thr Val Ser Ser
                        100                 105

<210> 81
<211> 106
<212> PRT
<213> Homo sapiens

<400> 81
Gln Val Gln Leu Glu Gln Ser Gly Pro Gly Leu Val Lys Pro Ser Glu
1               5                   10                  15
Thr Leu Ser Leu Thr Cys Thr Val Ser Gly Gly Ser Ile Ser Ser Gly
                20                  25                  30
Thr Tyr His Trp Ser Trp Ile Arg Gln His Pro Gly Arg Gly Leu Glu
                35                  40                  45
Trp Ile Gly Tyr Ile Tyr Tyr Ser Gly Ser Thr Tyr His Asn Pro Ser
            50                  55                  60
Leu Lys Ser Arg Ile Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Gly Gly Asp Gly Tyr Arg Tyr
                100                 105

<210> 82
<211> 95
<212> PRT
<213> Homo sapiens

<400> 82
Glu Ile Val Met Thr Gln Ser Pro Ala Thr Leu Ser Val Ser Pro Gly
```

Page 26 of 29

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
         1               5                    10                   15
         Gln Arg Ala Thr Leu Ser Cys Arg Ala Ser Gln Ser Val Ser Ser Asn
                         20                  25                  30
         Leu Ala Trp Tyr Gln Gln Lys Pro Gly Gln Ala Pro Arg Leu Leu Ile
                         35                  40                  45
         Tyr Gly Ala Ser Thr Arg Ala Thr Gly Ile Pro Ala Arg Phe Ser Gly
                         50                  55                  60
         Ser Gly Ser Gly Thr Glu Phe Thr Leu Thr Ile Ser Ser Leu Gln Ser
         65                  70                  75                  80
         Glu Asp Phe Ala Val Tyr Tyr Cys Gln Gln Tyr Asn Asn Trp Pro
                         85                  90                  95

<210> 83
<211> 33
<212> DNA
<213> Artificial Sequence

<220>
<223> Synthetic oligonucleotide primer sequence

<400> 83
atattacgaa ttcacttgcg tctcgccctc cgg                                    33

<210> 84
<211> 34
<212> DNA
<213> Artificial Sequence

<220>
<223> Synthetic oligonucleotide primer sequence

<400> 84
cagcttagag ctagccggct ctccggctcc ggca                                   34

<210> 85
```

UNITED STATES PATENT AND TRADEMARK OFFICE
CERTIFICATE OF CORRECTION

PATENT NO. : 7,090,844 B2  
APPLICATION NO. : 10/660357  
DATED : August 15, 2006  
INVENTOR(S) : Bar-Eli et al.

It is certified that error appears in the above-identified patent and that said Letters Patent is hereby corrected as shown below:

```
<211> 12
<212> DNA
<213> Homo sapiens

<400> 85
ggttcgggga gt                                                        12

<210> 86
<211> 18
<212> DNA
<213> Homo sapiens

<400> 86
cgatttttgg agtggtta                                                  18

<210> 87
<211> 11
<212> DNA
<213> Homo sapiens

<400> 87
cagtggctgg t                                                         11

<210> 88
<211> 11
<212> DNA
<213> Homo sapiens

<400> 88
gagatggcta c                                                         11

<210> 89
<211> 13
<212> DNA
<213> Homo sapiens

<400> 89
```

UNITED STATES PATENT AND TRADEMARK OFFICE
CERTIFICATE OF CORRECTION

PATENT NO. : 7,090,844 B2
APPLICATION NO. : 10/660357
DATED : August 15, 2006
INVENTOR(S) : Bar-Eli et al.

It is certified that error appears in the above-identified patent and that said Letters Patent is hereby corrected as shown below:

```
       gagatggcta caa                                              13

<210> 90
       <211> 11
       <212> DNA
       <213> Homo sapiens

<400> 90
       gagatggcta c                                                11--
```

In Col. 58, line 21, claim 15, please delete "9, 13," and insert --9, 13,--, therefor.

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,090,844 B2 |
| APPLICATION NO. | : 10/660357 |
| DATED | : August 15, 2006 |
| INVENTOR(S) | : Menashe Bar-Eli and Larry L. Green |

Page 1 of 1

It is certified that error appears in the above-identified patent and that said Letters Patent is hereby corrected as shown below:

In Col. 1, line 4 please insert:

-- STATEMENT REGARDING FEDERALLY SPONSORED R&D

This invention was made with government support under CA064137 awarded by The National Institutes of Health. The government has certain rights in the invention. --

Signed and Sealed this

Seventh Day of April, 2009

JOHN DOLL
*Acting Director of the United States Patent and Trademark Office*